US011175580B2

(12) United States Patent
Hatakeyama et al.

(10) Patent No.: US 11,175,580 B2
(45) Date of Patent: *Nov. 16, 2021

(54) RESIST COMPOSITION AND PATTERNING PROCESS

(71) Applicant: Shin-Etsu Chemical Co., Ltd., Tokyo (JP)

(72) Inventors: Jun Hatakeyama, Joetsu (JP); Masaki Ohashi, Joetsu (JP); Takayuki Fujiwara, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 169 days.

This patent is subject to a terminal disclaimer.

(21) Appl. No.: 16/565,776

(22) Filed: Sep. 10, 2019

(65) Prior Publication Data

US 2020/0089111 A1    Mar. 19, 2020

(30) Foreign Application Priority Data

Sep. 18, 2018 (JP) .............................. JP2018-173519

(51) Int. Cl.
*G03F 7/004* (2006.01)
*G03F 7/20* (2006.01)
*C07C 381/12* (2006.01)
*G03F 7/039* (2006.01)
*G03F 7/038* (2006.01)

(52) U.S. Cl.
CPC .......... *G03F 7/0045* (2013.01); *C07C 381/12* (2013.01); *G03F 7/0382* (2013.01); *G03F 7/0392* (2013.01); *G03F 7/2004* (2013.01); *G03F 7/2059* (2013.01)

(58) Field of Classification Search
CPC ...... G03F 7/0045; G03F 7/0046; G03F 7/038; G03F 7/0382; G03F 7/039; G03F 7/0392; G03F 7/0395; G03F 7/0397
See application file for complete search history.

(56) References Cited

U.S. PATENT DOCUMENTS

| 8,785,105 | B2 | 7/2014 | Ohsawa et al. |
| 9,766,541 | B2 | 9/2017 | Yamazaki et al. |
| 2017/0205709 | A1* | 7/2017 | Hatakeyama ........... G03F 7/322 |
| 2018/0095364 | A1* | 4/2018 | LaBeaume ............ G03F 7/0045 |

FOREIGN PATENT DOCUMENTS

| JP | 2012-107151 A | | 6/2012 |
| JP | 2017-15777 A | | 1/2017 |
| JP | 2018-118962 A | | 8/2018 |
| JP | 2018118962 A | * | 8/2018 |

OTHER PUBLICATIONS

English Machine Translation of Matsuyama (JP2018118962A) (Year: 2018).*

* cited by examiner

*Primary Examiner* — John A McPherson
*Assistant Examiner* — Nicholas E Brown
(74) *Attorney, Agent, or Firm* — Westerman, Hattori, Daniels & Adrian, LLP

(57) ABSTRACT

A resist composition comprising a base polymer and an acid generator containing a sulfonium salt having an iodized benzene ring offers a high sensitivity, minimal LWR and improved CDU independent of whether it is of positive or negative tone.

14 Claims, No Drawings

RESIST COMPOSITION AND PATTERNING PROCESS

CROSS-REFERENCE TO RELATED APPLICATION

This non-provisional application claims priority under 35 U.S.C. § 119(a) on Patent Application No. 2018-173519 filed in Japan on Sep. 18, 2018, the entire contents of which are hereby incorporated by reference.

TECHNICAL FIELD

This invention relates to a resist composition and a pattern forming process.

BACKGROUND ART

To meet the demand for higher integration density and operating speed of LSIs, the effort to reduce the pattern rule is in rapid progress. In particular, the enlargement of the logic memory market to comply with the wide-spread use of smart phones drives forward the miniaturization technology. As the advanced miniaturization technology, manufacturing of microelectronic devices at the 10-nm node by double patterning of the ArF immersion lithography has been implemented in a mass scale. Manufacturing of 7-nm node devices as the next generation by the double patterning technology is approaching to the verge of high-volume application. The candidate for 5-nm node devices as the next generation but one is EUV lithography.

The EUV resist material must meet high sensitivity, high resolution and low edge roughness (LWR) at the same time. As the acid diffusion distance is reduced, LWR is reduced, but sensitivity becomes lower. For example, as the PEB temperature is lowered, the outcome is a reduced LWR, but a lower sensitivity. As the amount of quencher added is increased, the outcome is a reduced LWR, but a lower sensitivity. It is necessary to overcome the tradeoff relation between sensitivity and LWR The wavelength (13.5 nm) of EUV is shorter than the wavelength (193 nm) of ArF excimer laser by at least one order, and the energy density of EUV is greater than that of ArF by one order. It is believed that since the number of photons available in a photoresist layer upon EUV exposure is as small as 1/14 of that of ArF exposure, a variation of size (LWR or CDU) is largely affected by a variation of photon number. There arises the phenomenon that a hole pattern is not opened at a one-in-several millions probability because of a variation of photon number. It is pointed out that the light absorption of a photoresist material must be increased in order to minimize the variation of photon number.

Patent Documents 1 to 3 disclose a sulfonium salt having a halogen-substituted benzene ring. Since fully EUV absorptive halogen atoms are introduced on the cation side, the decomposition of the cation upon EUV exposure is promoted, leading to an improvement in sensitivity.

CITATION LIST

Patent Document 1: JP-A 2012-107151 (U.S. Pat. No. 8,785,105)
Patent Document 2: JP-A 2017-015777 (U.S. Pat. No. 9,766,541)
Patent Document 3: JP-A 2018-118962

SUMMARY OF INVENTION

For the chemically amplified resist composition using an acid catalyst, it is desired to develop an acid generator capable of achieving a high sensitivity and reducing the LWR and CDU of a hole pattern.

An object of the invention is to provide a resist composition which achieves a high sensitivity, minimal LWR and improved CDU independent of whether it is of positive or negative tone, and a pattern forming process using the resist composition.

The inventors have found that a resist composition having a high sensitivity, minimal LWR, improved CDU, high contrast, high resolution and wide process margin is obtained using a sulfonium salt having an iodized benzene ring as an acid generator.

In one aspect, the invention provides a resist composition comprising an acid generator containing a sulfonium salt having the formula (1).

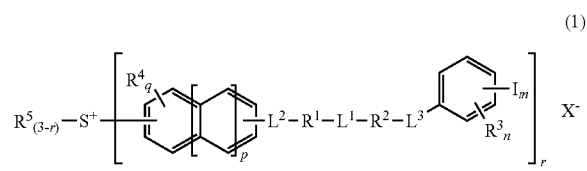

(1)

Herein $R^1$ and $R^2$ are each independently a single bond or a $C_1$-$C_{20}$ divalent aliphatic hydrocarbon group which may contain an ether bond, ester bond or hydroxyl; $L^1$ is an ester bond, ether bond or amide bond; $L^2$ and $L^3$ are each independently a single bond, ester bond, ether bond or amide bond; $R^3$ is hydroxyl, carboxyl, nitro, cyano, fluorine, chlorine, bromine, amino, or a $C_1$-$C_{20}$ alkyl, $C_1$-$C_{20}$ alkoxy, $C_2$-$C_{20}$ acyloxy, $C_2$-$C_{20}$ alkoxycarbonyl or $C_1$-$C_4$ alkylsulfonyloxy group, which may contain fluorine, chlorine, bromine, hydroxyl or amino, or —$NR^{3A}$—$C(=O)$—$R^{3B}$ or —$NR^{3A}$—$C(=O)$—$O$—$R^{3B}$, wherein $R^{3A}$ is hydrogen or a $C_1$-$C_6$ alkyl group which may contain halogen, hydroxyl, $C_1$-$C_{10}$ alkoxy, $C_2$-$C_{10}$ acyl or $C_2$-$C_{10}$ acyloxy, $R^{3B}$ is a $C_1$-$C_{16}$ alkyl, $C_2$-$C_{16}$ alkenyl or $C_6$-$C_{12}$ aryl group, which may contain halogen, hydroxyl, $C_1$-$C_{10}$ alkoxy, $C_2$-$C_{10}$ acyl or $C_2$-$C_{10}$ acyloxy; $R^4$ is hydroxyl, carboxyl, nitro, cyano, fluorine, chlorine, bromine, iodine, amino, or a $C_1$-$C_{20}$ alkyl, $C_1$-$C_{20}$ alkoxy, $C_2$-$C_{20}$ acyloxy, $C_2$-$C_{20}$ alkoxycarbonyl or $C_1$-$C_4$ alkylsulfonyloxy group, which may contain fluorine, chlorine, bromine, iodine, hydroxyl, amino or ether bond, $R^5$ is a $C_1$-$C_{20}$ monovalent hydrocarbon group which may contain a heteroatom, in case of r=1, two $R^5$ may be the same or different and may bond together to form a ring with the sulfur atom to which they are attached; $X^-$ is a non-nucleophilic counter ion; m is an integer of 1 to 5, n is an integer of 0 to 3, the sum of m+n is 1 to 5, p is 0 or 1, q is an integer of 0 to 4, and r is an integer of 1 to 3. Preferably, m is an integer of 2 to 5.

The non-nucleophilic counter ion is typically a fluorinated sulfonate, fluorinated imide or fluorinated methide ion.

The resist composition may further comprise an organic solvent.

The resist composition may further comprise a base polymer. Preferably, the base polymer comprises recurring units having the formula (a1) or recurring units having the formula (a2).

(a1)

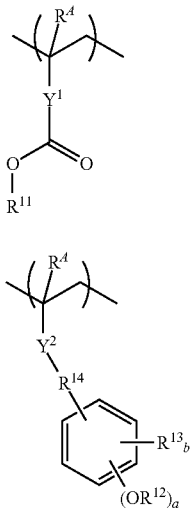

(a2)

Herein $R^A$ is each independently hydrogen or methyl, $Y^1$ is a single bond, phenylene group, naphthylene group, or $C_1$-$C_{12}$ linking group containing an ester bond or lactone ring, $Y^2$ is a single bond or ester bond, $R^{11}$ and $R^{12}$ each are an acid labile group, $R^{13}$ is fluorine, trifluoromethyl, cyano, $C_1$-$C_6$ alkyl, $C_1$-$C_6$ alkoxy, $C_2$-$C_7$ acyl, $C_2$-$C_7$ acyloxy, or $C_2$-$C_7$ alkoxyarbonyl group, $R^{14}$ is a single bond or a $C_1$-$C_6$ straight or branched alkanediyl group in which some carbon may be replaced by an ether bond or ester bond, a is 1 or 2, b is an integer of 0 to 4, the sum of a+b is 1 to 5.

In one embodiment, the resist composition is a chemically amplified positive resist composition.

In another embodiment, the base polymer is free of an acid labile group, and the resist composition is a chemically amplified negative resist composition.

In a preferred embodiment, the base polymer further comprises recurring units of at least one type selected from the formulae (f1) to (f3).

(f1)

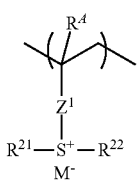

(f2)

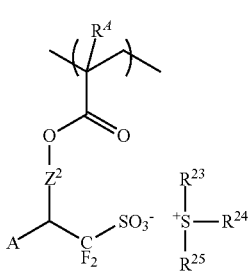

(f3)

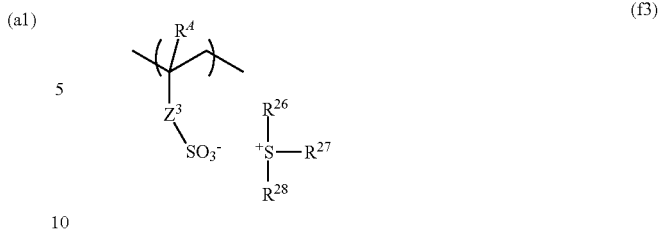

Herein $R^A$ is each independently hydrogen or methyl; $Z^1$ is a single bond, phenylene group, —O—$Z^{11}$—, —C(O)—O—$Z^{11}$— or —C(=O)—NH—$Z^{11}$—, $Z^{11}$ is a $C_1$-$C_6$ alkanediyl group, $C_2$-$C_6$ alkenediyl group, or phenylene group, which may contain carbonyl, ester bond, ether bond or hydroxyl; $Z^2$ is a single bond, —$Z^{21}$—C(=O)O—, —$Z^{21}$—O— or —$Z^{21}$—O—C(=O)—, $Z^{21}$ is a $C_1$-$C_{12}$ alkanediyl group which may contain carbonyl, ester bond or ether bond; $Z^3$ is a single bond, methylene, ethylene, phenylene, fluorinated phenylene, —O—$Z^{31}$—, —C(=O)—O—$Z^{31}$— or —C(=O)—NH—$Z^{31}$—, $Z^{31}$ is a $C_1$-$C_6$ alkanediyl group, $C_2$-$C_6$ alkenediyl group, phenylene group, fluorinated phenylene group, or trifluoromethyl-substituted phenylene group, which may contain carbonyl, ester bond, ether bond or hydroxyl; $R^{21}$ to $R^{28}$ are each independently a $C_1$-$C_{20}$ monovalent hydrocarbon group which may contain a heteroatom, any two of $R^{23}$, $R^{24}$ and $R^{25}$ or any two of $R^{26}$, $R^{27}$ and $R^{28}$ may bond together to form a ring with the sulfur atom to which they are attached; A is hydrogen or trifluoromethyl; and $M^-$ is a non-nucleophilic counter ion.

The resist composition may further comprise a surfactant.

In another aspect, the invention provides a process for forming a pattern comprising the steps of applying the resist composition defined above onto a substrate, baking to form a resist film, exposing the resist film to high-energy radiation, and developing the exposed resist film in a developer.

Preferably, the high-energy radiation is ArF excimer laser radiation of wavelength 193 nm, KrF excimer laser radiation of wavelength 248 nm, EB, or EUV of wavelength 3 to 15 nm.

ADVANTAGEOUS EFFECTS OF INVENTION

The sulfonium salt having an iodized benzene ring is highly effective for suppressing acid diffusion because of the large atomic weight of iodine. Since iodine is highly absorptive to EUV of wavelength 13.5 nm, iodine generates secondary electrons upon EUV exposure, leading to a high sensitivity. Thus a resist composition having a high sensitivity, minimal LWR and improved CDU is designed.

DESCRIPTION OF EMBODIMENTS

As used herein, the singular forms "a," "an" and "the" include plural referents unless the context clearly dictates otherwise. The notation ($C_n$-$C_m$) means a group containing from n to m carbon atoms per group. As used herein, the term "iodized" or "fluorinated" indicates that a compound contains iodine or fluorine.

The abbreviations and acronyms have the following meaning.
EB: electron beam
EUV: extreme ultraviolet
Mw: weight average molecular weight
Mn: number average molecular weight
Mw/Mn: molecular weight distribution or dispersity GPC: gel permeation chromatography
PEB: post-exposure bake
PAG: photoacid generator
LWR: line width roughness
CDU: critical dimension uniformity Resist Composition One embodiment of the invention is a resist composition comprising a sulfonium salt having an iodized benzene ring and optionally, a base polymer. The sulfonium salt is an acid generator in that an acid is generated from the anion moiety as a result of the cation moiety being decomposed upon light exposure. The sulfonium salt is an effective acid generator particularly when its anion moiety is a fluorinated sulfonic acid, fluorinated imidic acid or fluorinated methide acid.

The sulfonium salt type acid generator is highly absorptive to EUV and efficiently decomposable because the cation moiety contains an iodized benzene ring. JP-A 2018-005224 and 2018-025789 describe sulfonium and iodonium salts having an iodized benzene ring in the anion wherein a high sensitivity is achieved by increasing the light absorption of the anion. The sulfonium salt is based on the mechanism that the cation moiety is decomposed as a result of light absorption. It is rather effective for gaining a high sensitivity to increase the absorption of the cation moiety.

The sulfonium salt having iodine of large atomic weight introduced in the cation moiety is less diffusive and fully compatible with a polymer. Thus the sulfonium salt is well dispersible, leading to improvements in LWR and CDU.

The sulfonium salt type acid generator having an iodized benzene ring exerts a LWR or CDU improving effect, which may stand good either in positive and negative tone pattern formation by aqueous alkaline development or in negative tone pattern formation by organic solvent development.

The sulfonium salt having an iodized benzene ring may be used as a positive resist material in the following sense. When a resist film is formed by dissolving the sulfonium salt alone or in admixture with a base polymer in a solvent and coating the solution, the resist film is alkali soluble in the exposed region.

Sulfonium Salt Having Iodized Benzene Ring

The sulfonium salt in the resist composition has the formula (1).

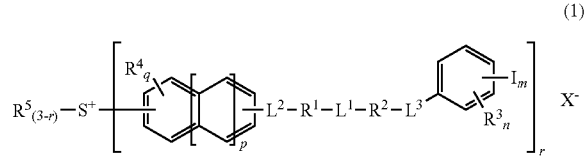

(1)

In formula (1), $R^1$ and $R^2$ are each independently a single bond or a $C_1$-$C_{20}$ divalent aliphatic hydrocarbon group which may contain an ether bond, ester bond or hydroxyl moiety.

The $C_1$-$C_{20}$ divalent aliphatic hydrocarbon group may be straight, branched or cyclic, and examples thereof include straight alkanediyl groups such as methylene, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl; branched alkanediyl groups such as ethane-1,1-diyl, propane-1,1-diyl, propane-1,2-diyl, propane-2,2-diyl, butane-1,3-diyl, butane-2,2-diyl, pentane-1,3-diyl, pentane-3,3-diyl, 2-methylpropane-1,1-diyl; cyclic alkanediyl groups such as cyclopropanediyl, cyclobutanediyl, cyclopentanediyl, cyclohexanediyl; and divalent unsaturated aliphatic hydrocarbon groups such as methylidene and propene-3,3-diyl. Of these, straight or branched alkanediyl groups are preferred.

In formula (1), $L^1$ is an ester bond, ether bond or amide bond. $L^2$ and $L^3$ are each independently a single bond, ester bond, ether bond or amide bond.

In formula (1), $R^3$ is hydroxyl, carboxyl, nitro, cyano, fluorine, chlorine, bromine, amino, or a $C_1$-$C_{20}$ alkyl, $C_1$-$C_{20}$ alkoxy, $C_2$-$C_{20}$ acyloxy, $C_2$-$C_{20}$ alkoxycarbonyl or $C_1$-$C_4$ alkylsulfonyloxy group, which may contain fluorine, chlorine, bromine, hydroxyl moiety or amino moiety, or —$NR^{3A}$—$C(=O)$—$R^{3B}$ or —$NR^{3A}$—$C(=O)$—$O$—$R^{3B}$, wherein $R^{3A}$ is hydrogen or a $C_1$-$C_6$ alkyl group which may contain halogen, hydroxyl, $C_1$-$C_{10}$ alkoxy, $C_2$-$C_{10}$ acyl or $C_2$-$C_{10}$ acyloxy moiety, $R^{3B}$ is a $C_1$-$C_{16}$ alkyl, $C_2$-$C_{16}$ alkenyl or $C_6$-$C_{12}$ aryl group, which may contain halogen, hydroxyl, $C_1$-$C_{10}$ alkoxy, $C_2$-$C_{10}$ acyl or $C_2$-$C_{10}$ acyloxy moiety.

In formula (1), $R^4$ is hydroxyl, carboxyl, nitro, cyano, fluorine, chlorine, bromine, iodine, amino, or a $C_1$-$C_{20}$ alkyl, $C_1$-$C_{20}$ alkoxy, $C_2$-$C_{20}$ acyloxy, $C_2$-$C_{20}$ alkoxycarbonyl or $C_1$-$C_4$ alkylsulfonyloxy group, which may contain fluorine, chlorine, bromine, iodine, hydroxyl, amino or ether bond.

The alkyl group may be straight, branched or cyclic, and examples thereof include methyl, ethyl, n-propyl, isopropyl, n-butyl, isobutyl, sec-butyl, tert-butyl, n-pentyl, neopentyl, cyclopentyl, n-hexyl, cyclohexyl, n-heptyl, n-octyl, 2-ethylhexyl, n-nonyl, n-decyl, n-undecyl, n-dodecyl, n-tridecyl, n-pentadecyl and n-hexadecyl.

The alkoxy group may be straight, branched or cyclic, and examples thereof include methoxy, ethoxy, n-propyloxy, isopropyloxy, n-butyloxy, isobutyloxy, sec-butyloxy, tert-butyloxy, n-pentyloxy, neopentyloxy, cyclopentyloxy, n-hexyloxy, cyclohexyloxy, n-heptyloxy, n-octyloxy, 2-ethylhexyloxy, n-nonyloxy, n-decyloxy, n-undecyloxy, n-dodecyloxy, n-tridecyloxy, n-pentadecyloxy, and n-hexadecyloxy.

Suitable acyl groups include acetyl, propionyl, butyryl, and isobutyryl.

Suitable acyloxy groups include acetyloxy, propionyloxy, butyryloxy, and isobutyryloxy.

Suitable alkoxycarbonyl groups include methoxycarbonyl, ethoxycarbonyl, n-propyloxycarbonyl, isopropyloxycarbonyl, n-butyloxycarbonyl, isobutyloxycarbonyl, sec-butyloxycarbonyl, tert-butyloxycarbonyl, n-pentyloxycarbonyl, neopentyloxycarbonyl, cyclopentyloxycarbonyl, n-hexyloxycarbonyl, cyclohexyloxycarbonyl, n-heptyloxycarbonyl, n-octyloxycarbonyl, 2-ethylhexyloxycarbonyl, n-nonyloxycarbonyl, n-decyloxycarbonyl, n-undecyloxycarbonyl, n-dodecyloxycarbonyl, n-tridecyloxycarbonyl, and n-pentadecyloxycarbonyl.

The alkenyl group may be straight, branched or cyclic, and examples thereof include vinyl, 1-propenyl, 2-propenyl, butenyl, hexenyl, and cyclohexenyl.

Suitable aryl groups include phenyl, tolyl, xylyl, 1-naphthyl, and 2-naphthyl.

In formula (1), $R^5$ is a $C_1$-$C_{20}$ monovalent hydrocarbon group which may contain a heteroatom. The monovalent hydrocarbon group may be straight, branched or cyclic, and examples thereof include $C_1$-$C_{20}$ alkyl groups, $C_2$-$C_{20}$ alkenyl groups, $C_2$-$C_{24}$ alkynyl groups, $C_6$-$C_{20}$ aryl groups, $C_7$-$C_{20}$ aralkyl groups, and combinations thereof. In these groups, some or all hydrogen may be substituted by hydroxyl moiety, carboxyl moiety, halogen, cyano moiety, amino moiety, nitro moiety, sultone ring-containing moiety, sulfone moiety or sulfonium salt-containing moiety, or an ether bond, ester bond, carbonyl moiety, sulfide bond, sulfonyl moiety or amide moiety may intervene in a carbon-carbon bond.

In case of r=1, two $R^5$ may be the same or different and may bond together to form a ring with the sulfur atom to which they are attached. Examples of the ring include the following structures.

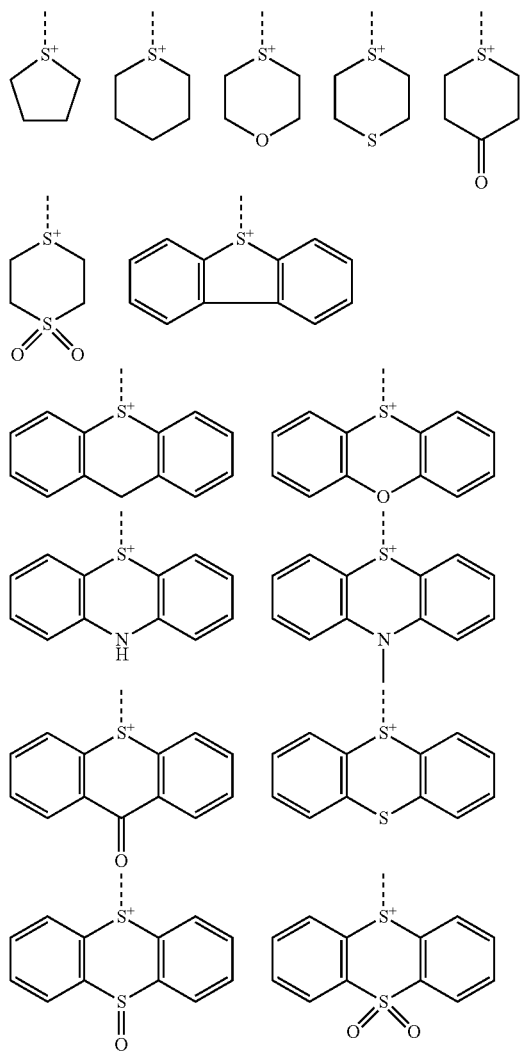

In these formulae, the broken line designates a valence bond to the aromatic ring to which the sulfur atom in formula (1) bonds.

In formula (1), $X^-$ is a non-nucleophilic counter ion, which is preferably a fluorinated sulfonate, fluorinated imide or fluorinated methide ion.

Examples include fluoroalkylsulfonate ions such as triflate, 2,2,2-trifluoroethauesulfonate, nonafluorobutanesulfonate, and arylsulfonate ions such as tosylate, benzenesulfonate, 4-fluorobenzenesulfonate, and 2,3,4,5,6-pentafluorobenzenesulfonate.

Other examples include α-fluorosulfonate anions as described in JP-A 2004-531749, 2007-145797, 2008-007410, 2018-101130, 2018-049177, and WO 2011/093139, β-fluorosulfonate anions as described in JP-A 2014-133725, α-fluorosulfonate anions, fluoroimide anions and fluoromethide anions as described in JP-A 2014-126767, and fluorosulfonimide anions as described in JP-A 2016-210761.

Also useful are fluorosulfonate anions having an iodized aromatic group as described in JP-A 2018-005224 and JP-A 2018-025789.

These anions are strong acids sufficient to induce deprotection reaction of acid labile groups in the positive resist material and crosslinking reaction or polarity switch reaction in the negative resist material.

In formula (1), m is an integer of 1 to 5, n is an integer of 0 to 3, the sum of m+n is 1 to 5, p is 0 or 1, q is an integer of 0 to 4, and r is an integer of 1 to 3.

Examples of the cation in the sulfonium salt having formula (1) are given below, but not limited thereto.

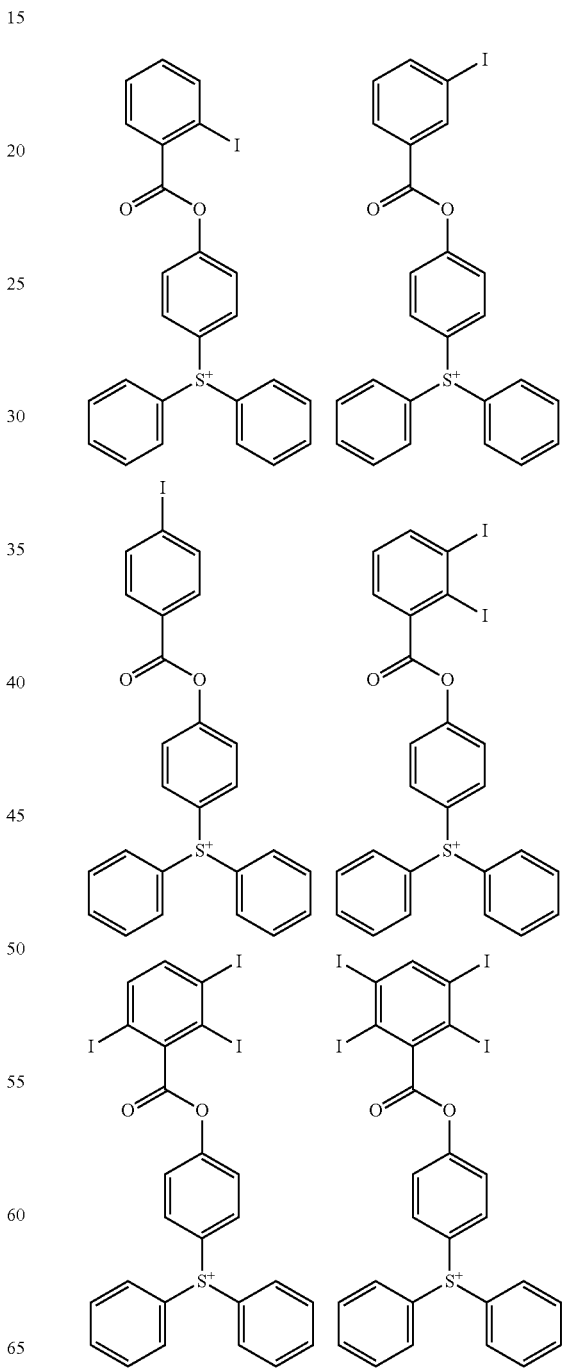

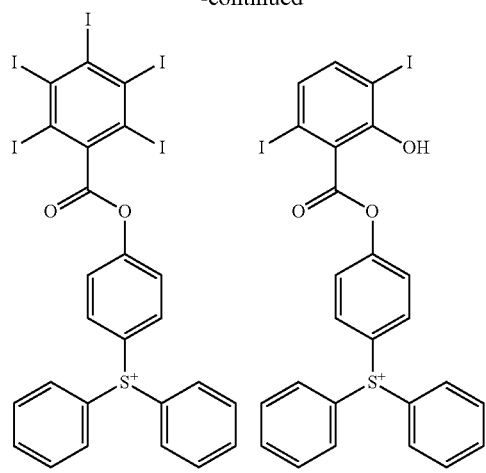
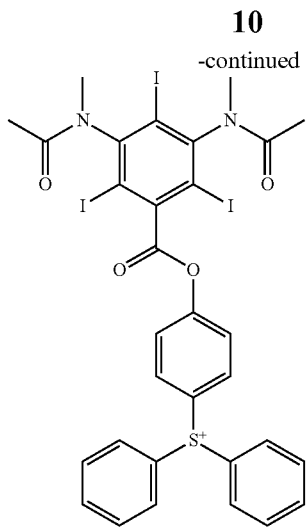
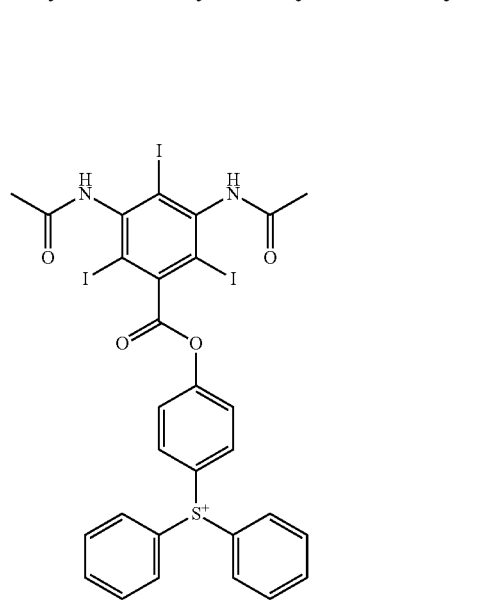
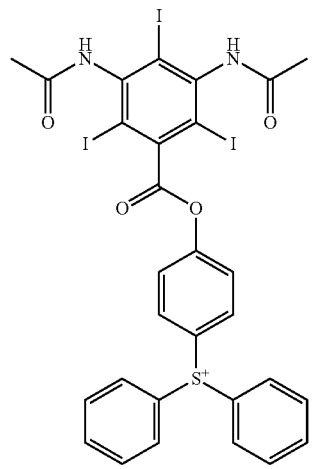
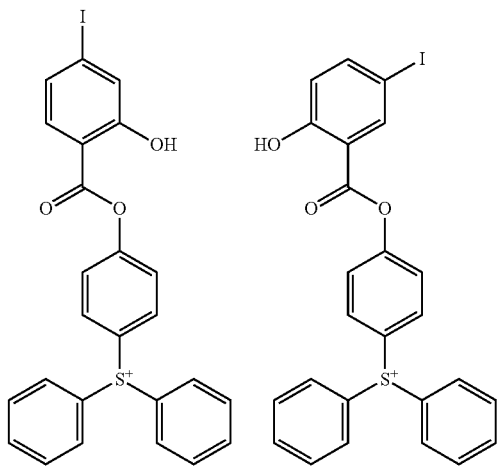
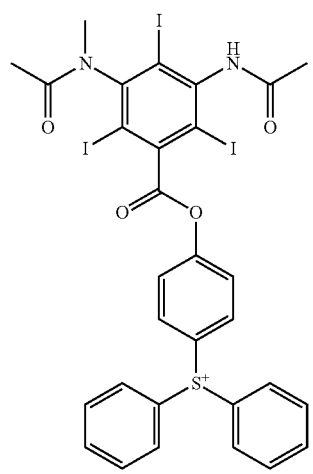
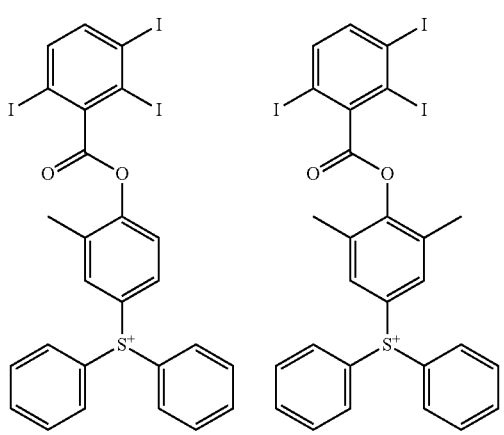

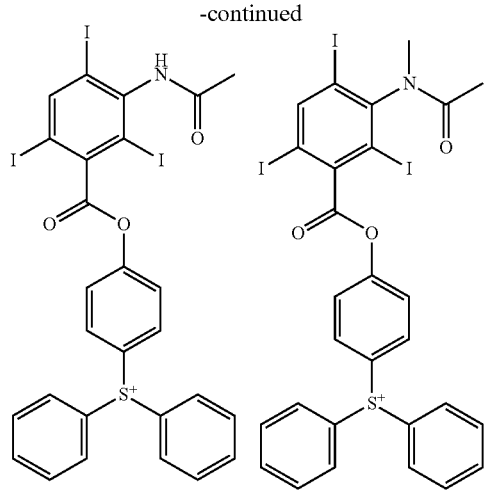
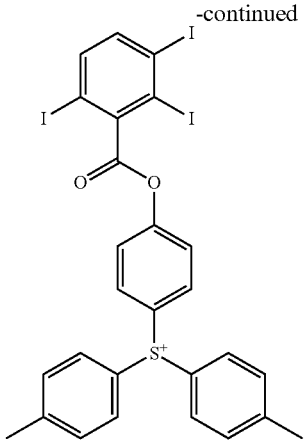
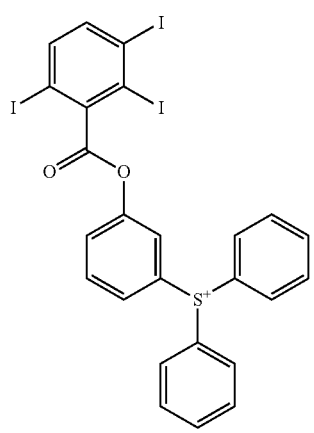
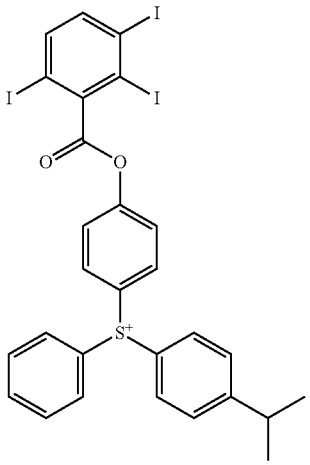
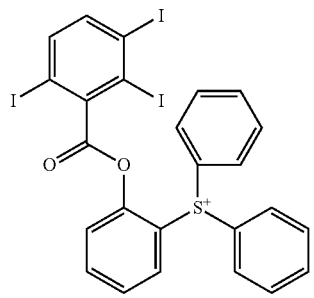 [SMILES: O=C(Oc1ccccc1[S+](c1ccccc1)c1ccccc1)c1c(I)ccc(I)c1I]
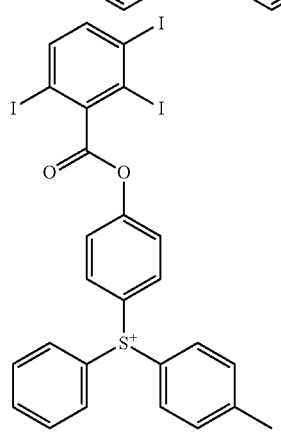
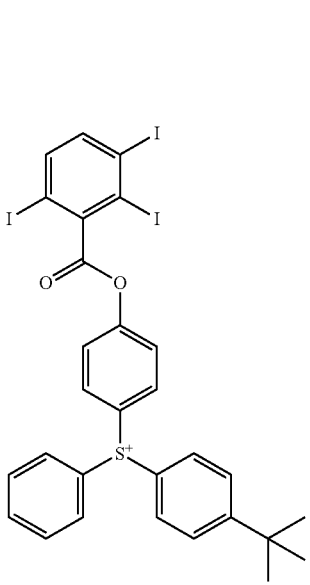

13
-continued
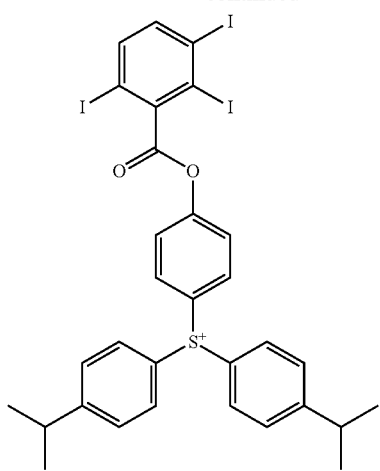
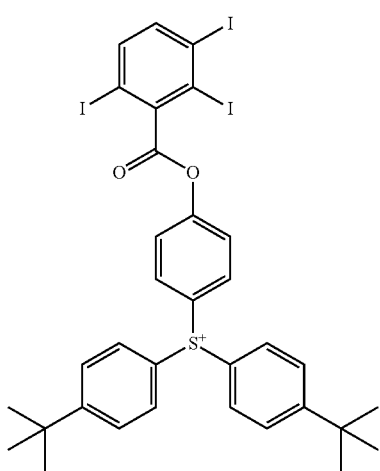
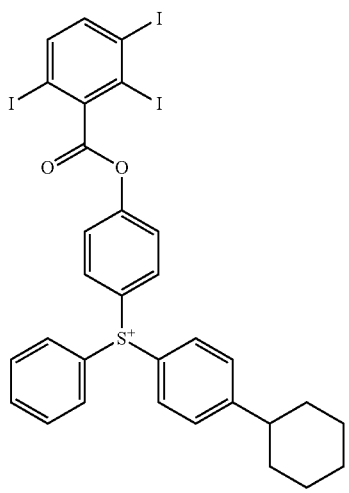
14
-continued
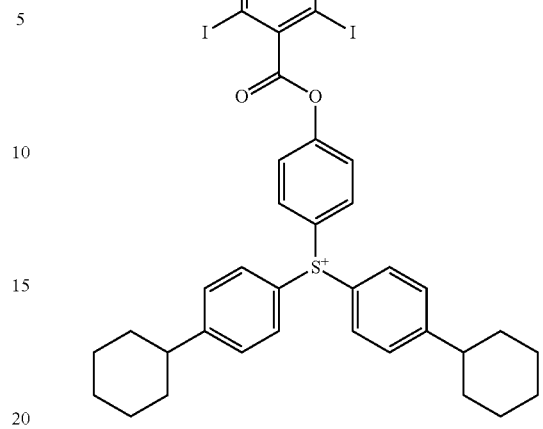
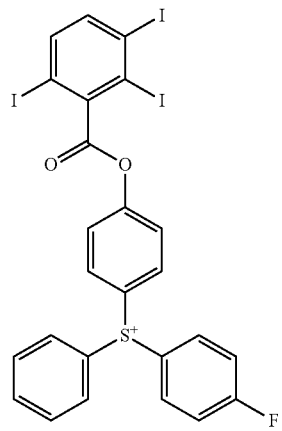
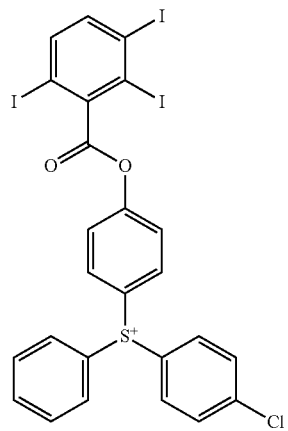

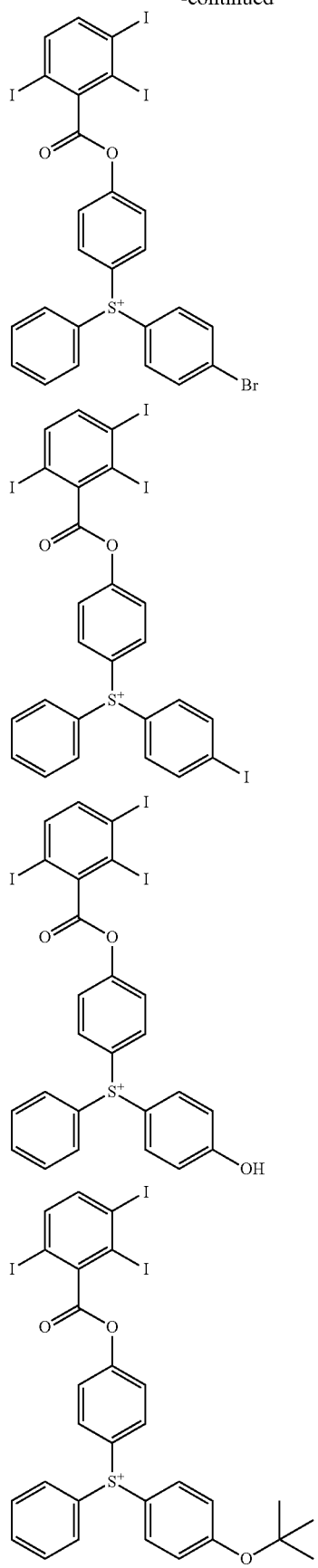
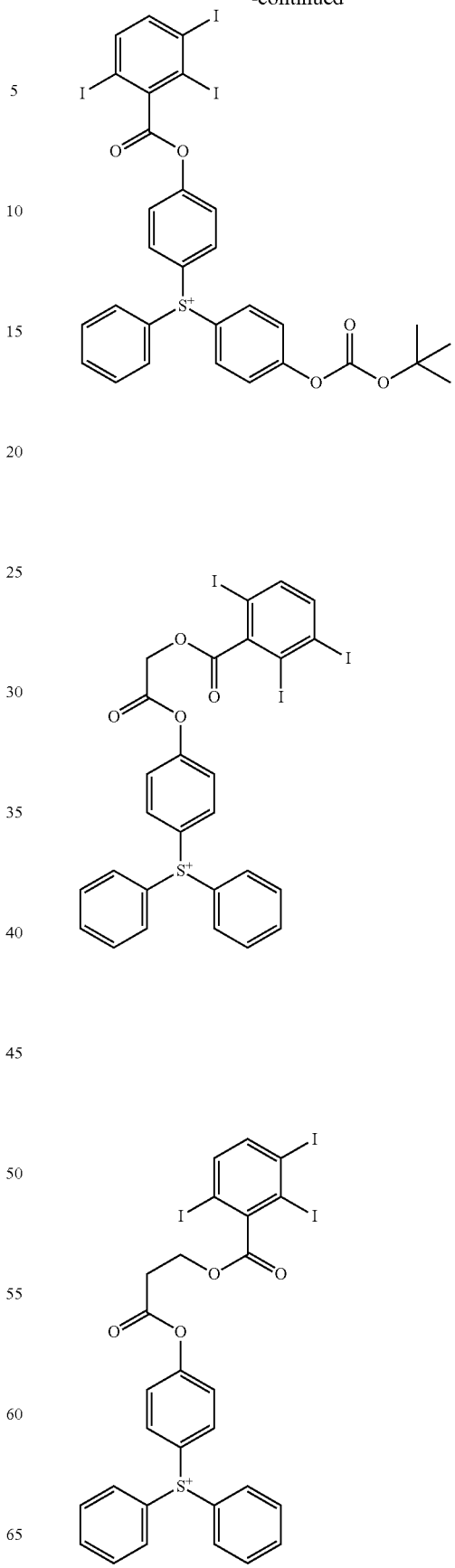

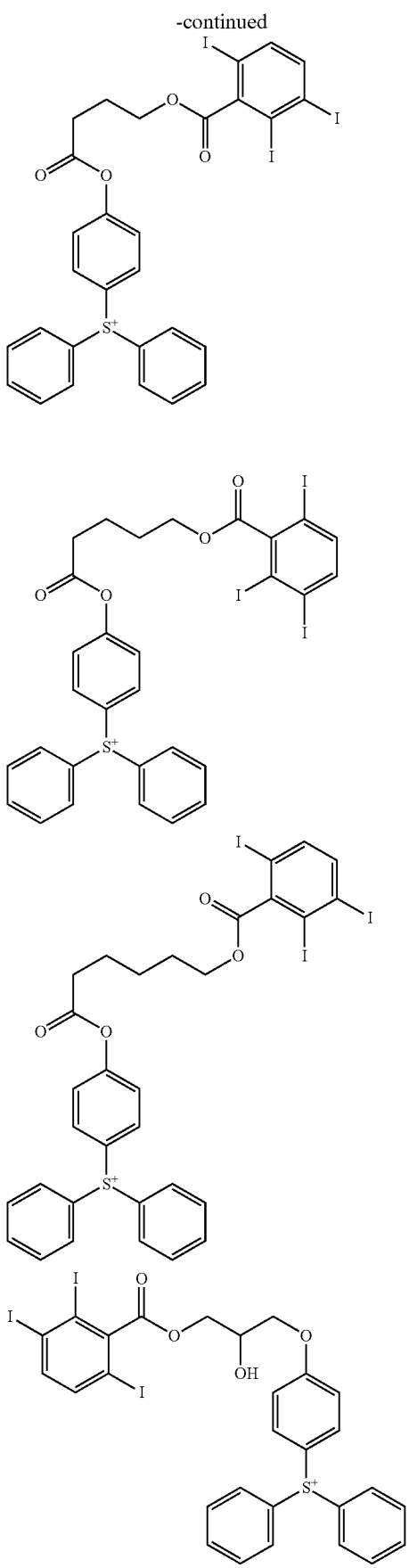
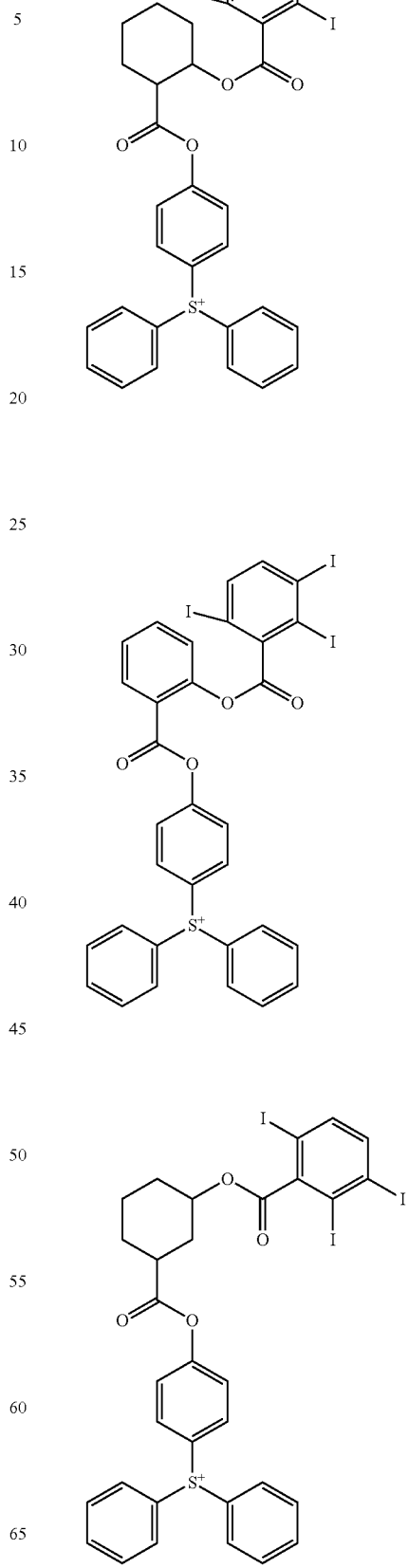

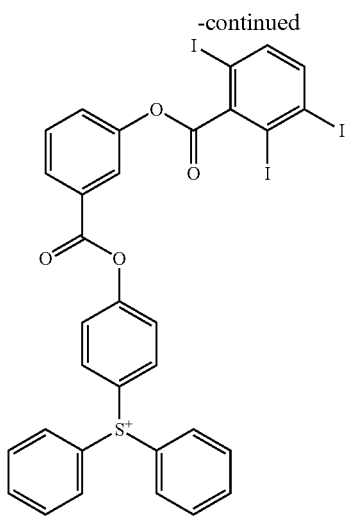
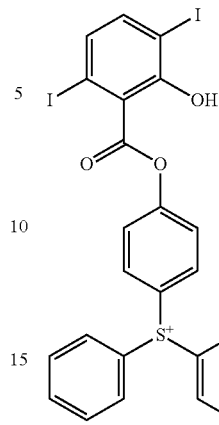
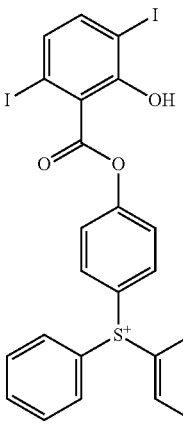
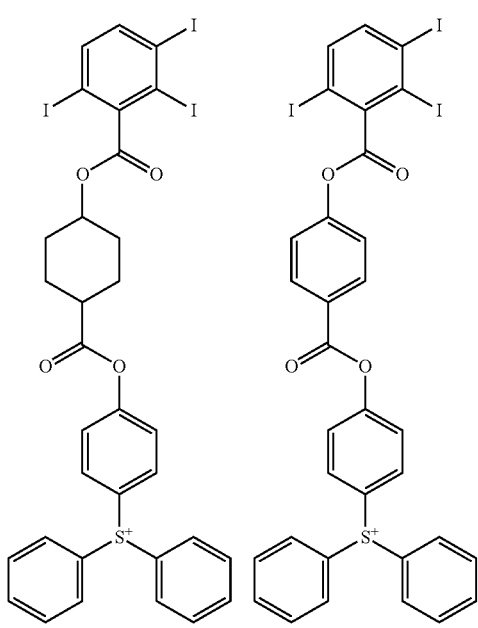
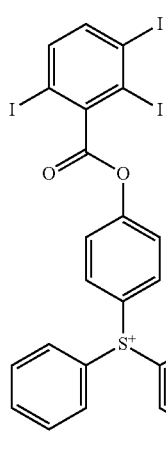
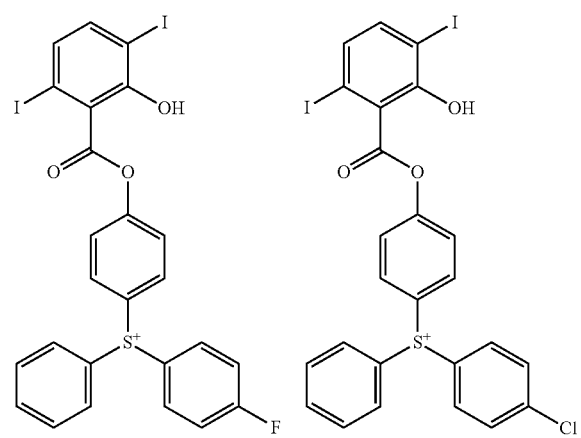
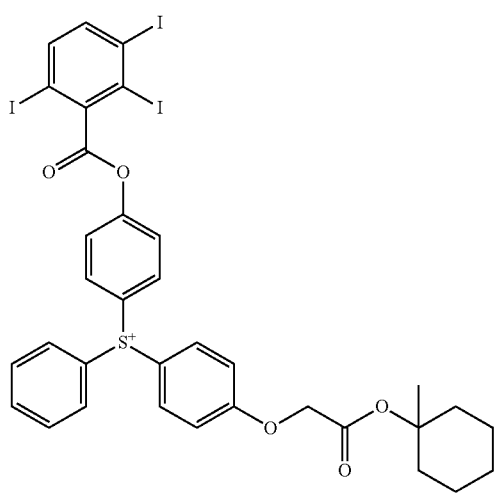

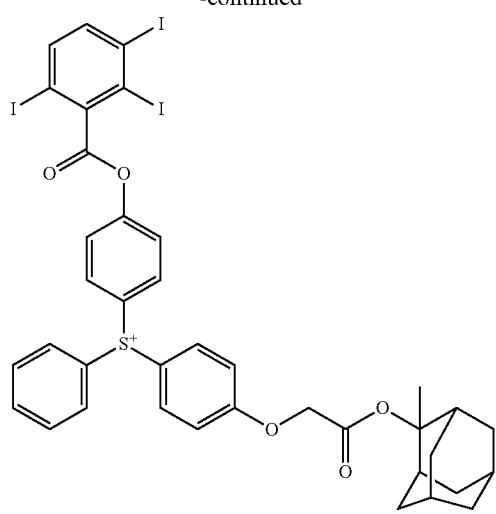
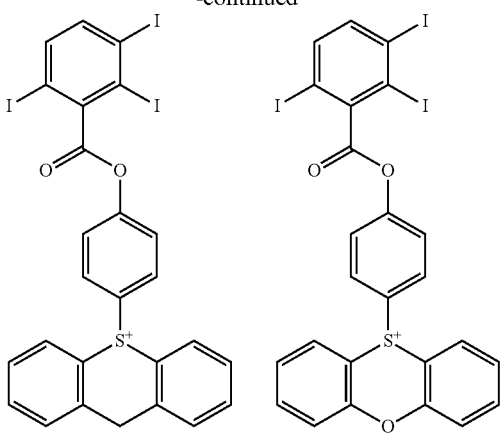
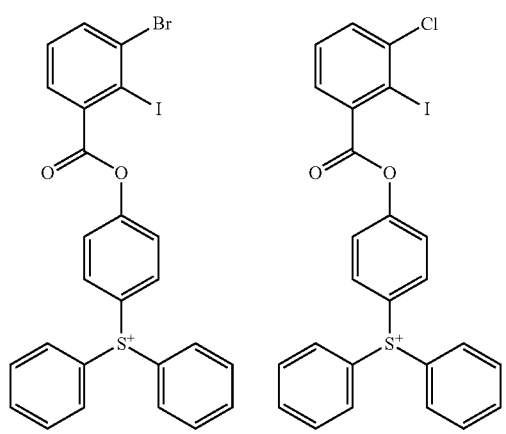
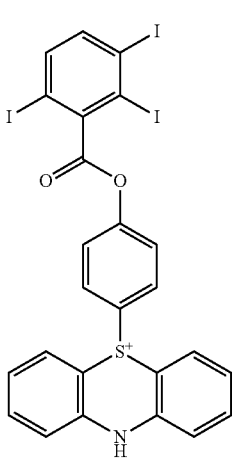
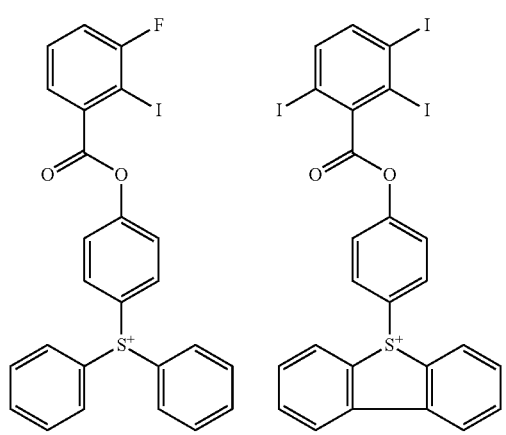
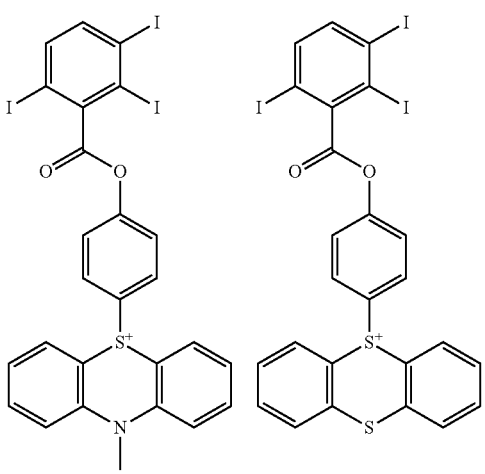

23
-continued
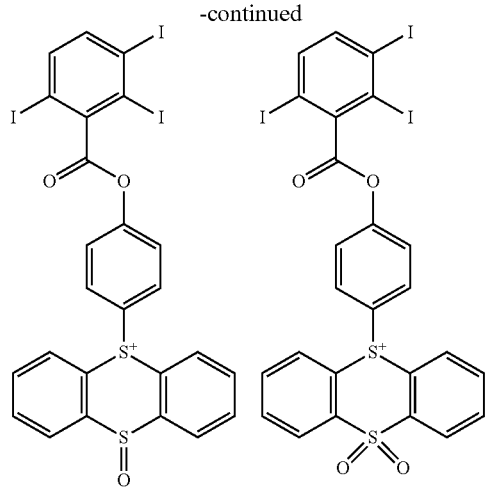
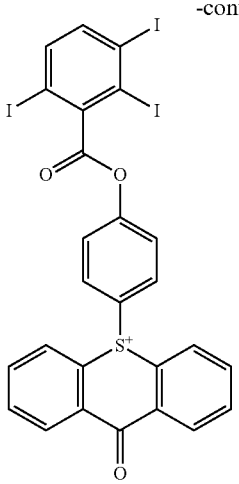
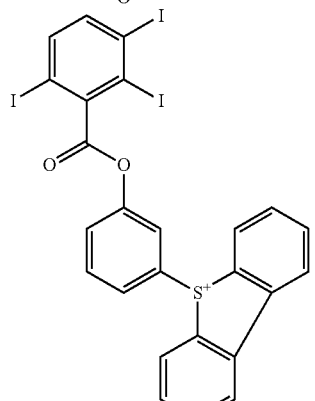
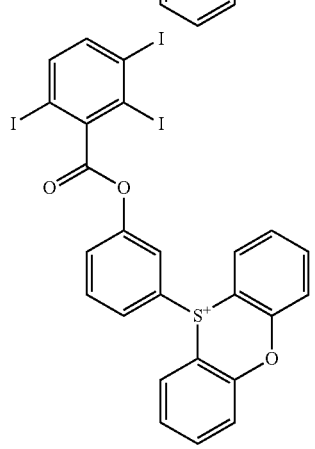
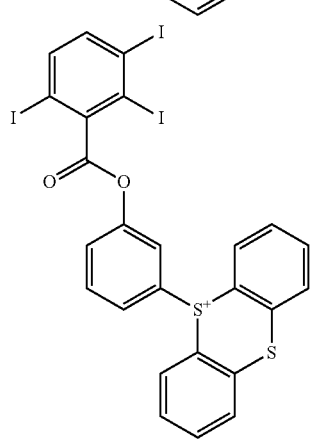
24
-continued
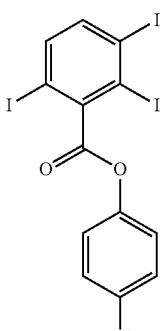
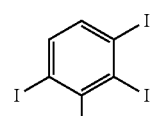
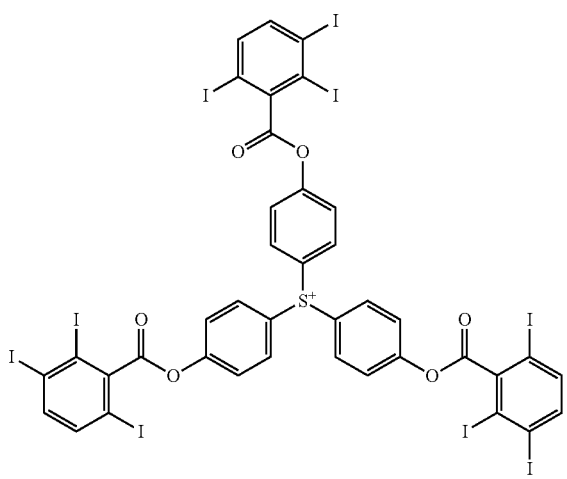

-continued
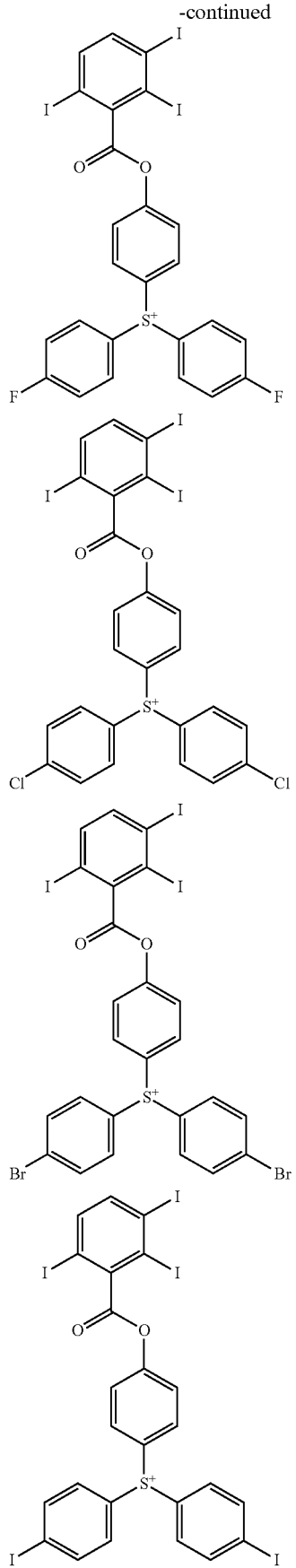
-continued
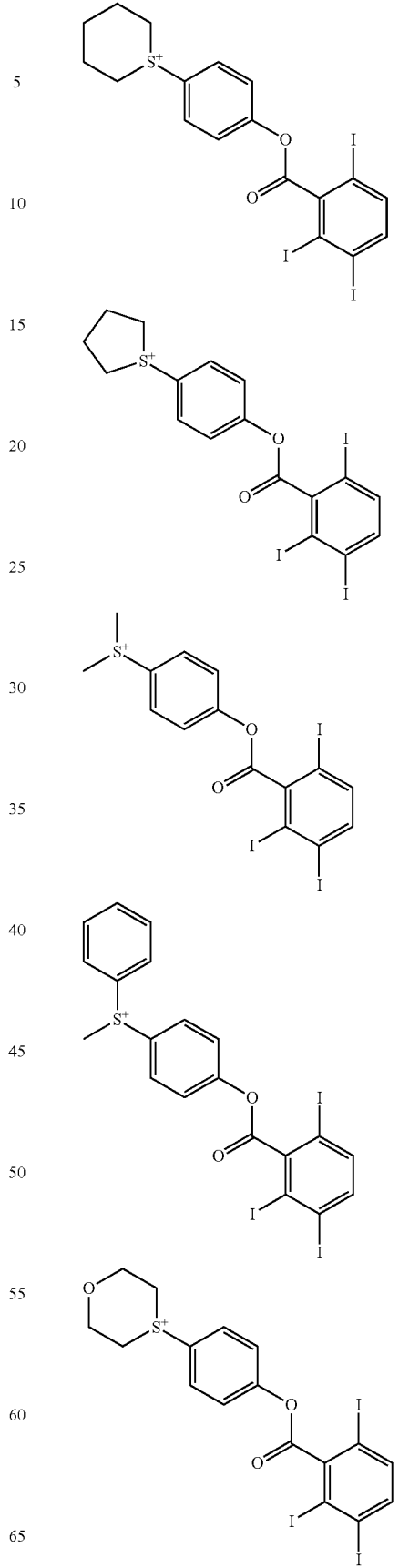

27
-continued
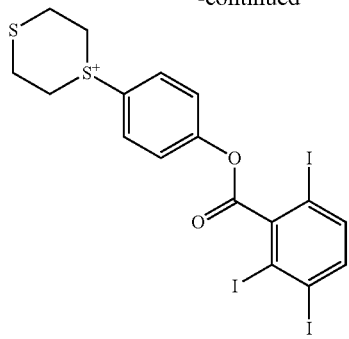
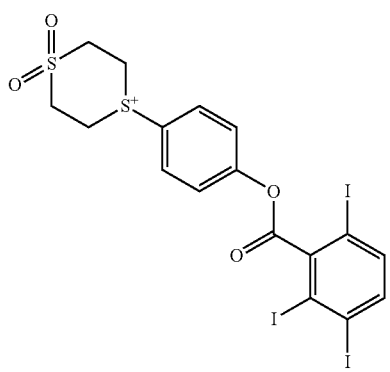
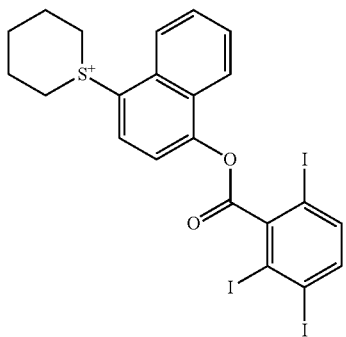
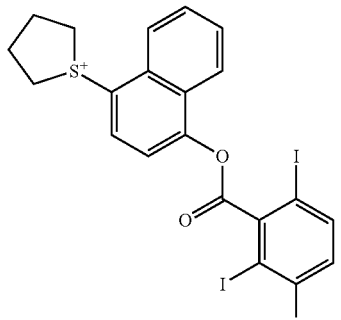
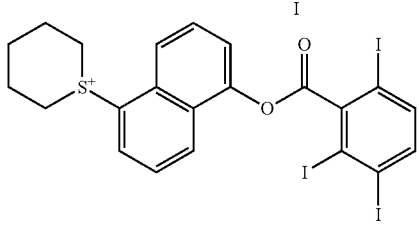
28
-continued
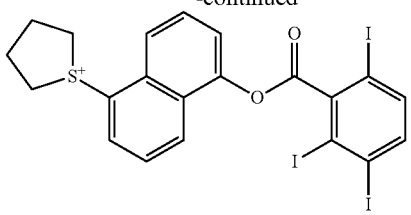
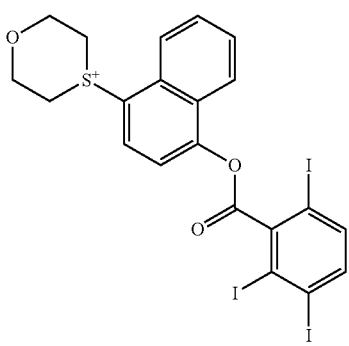
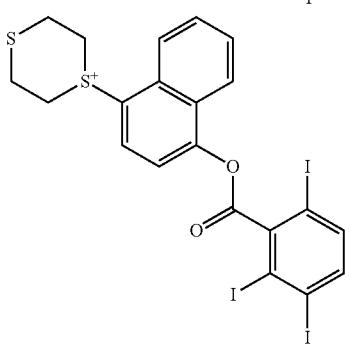
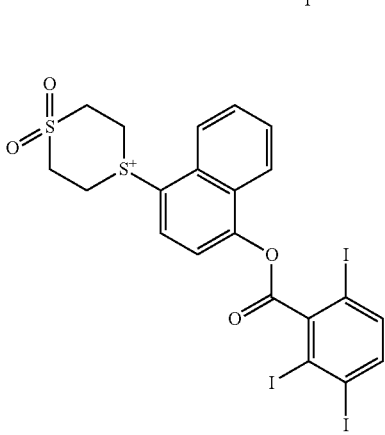
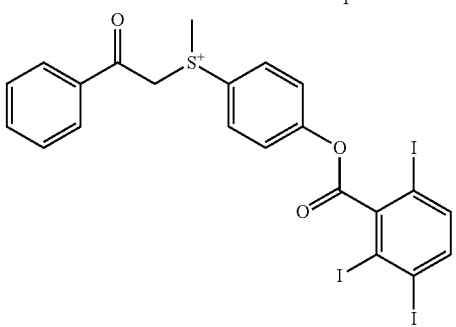

-continued
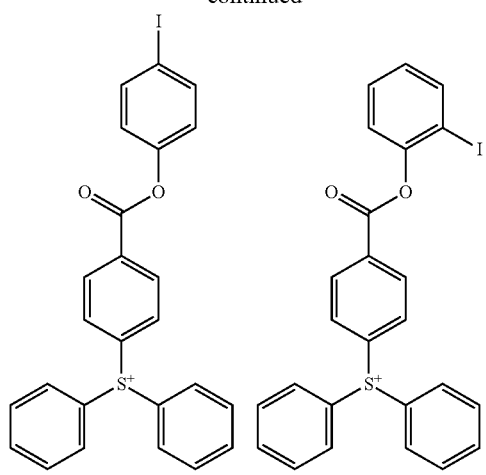 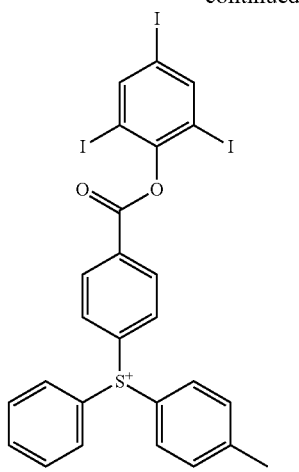
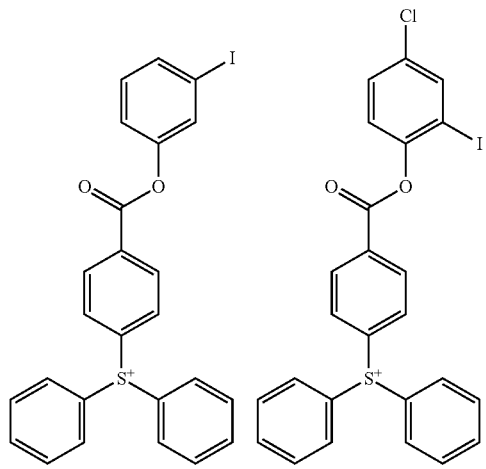 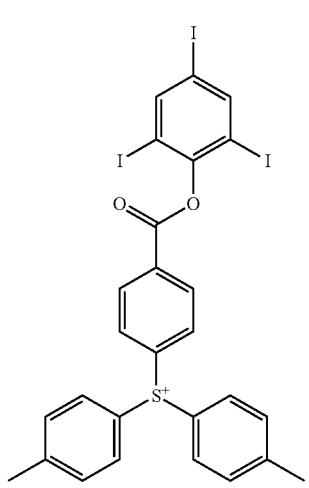
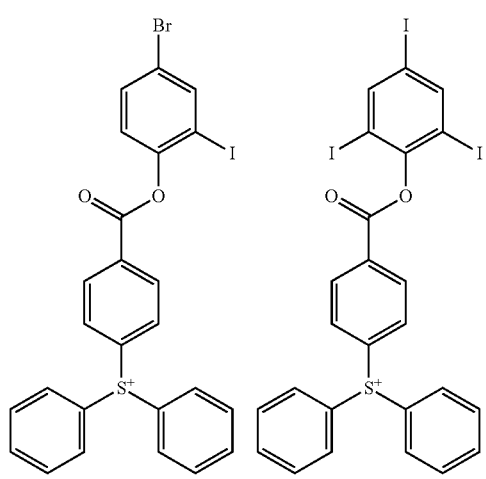 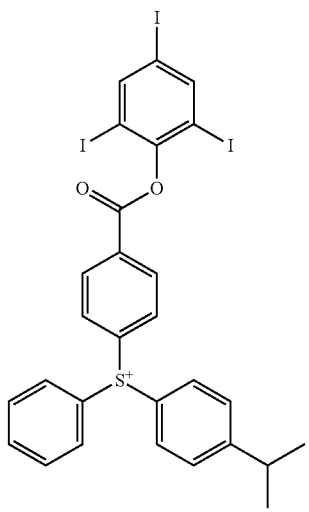

31
-continued
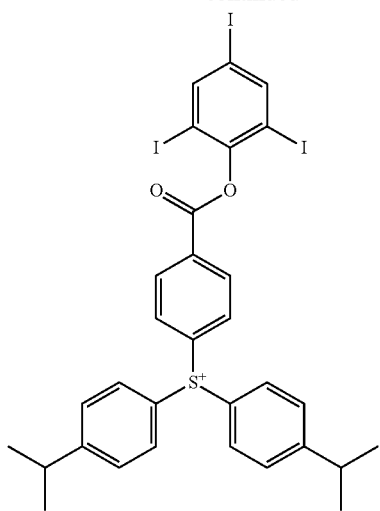
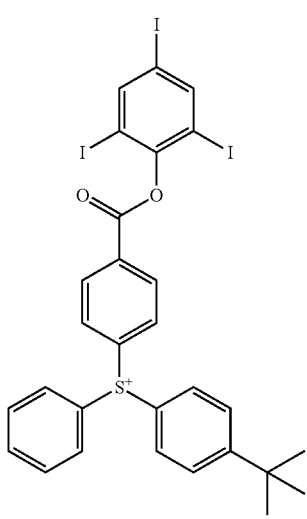
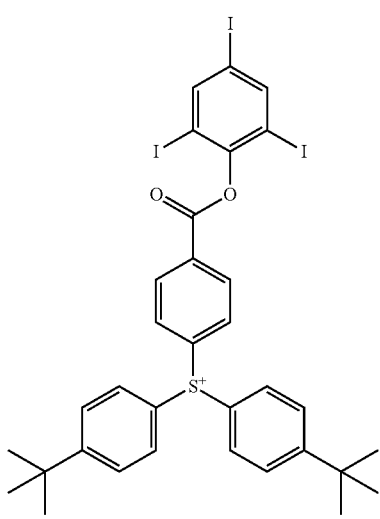
32
-continued
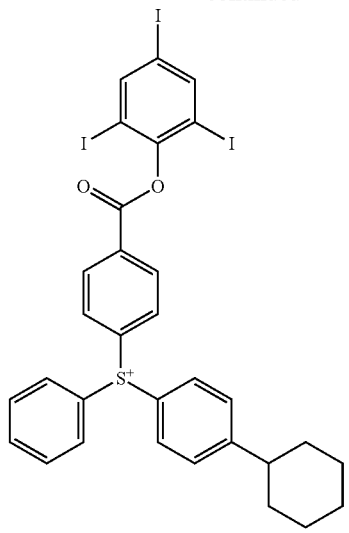
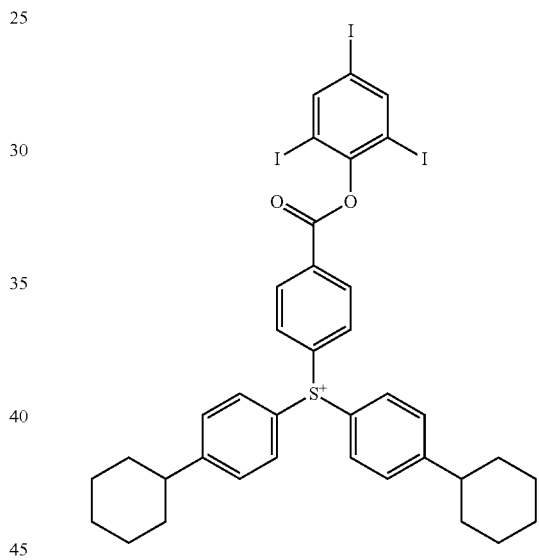
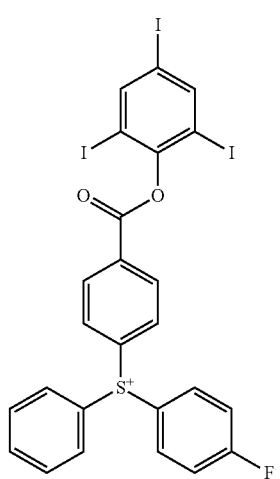

33
-continued
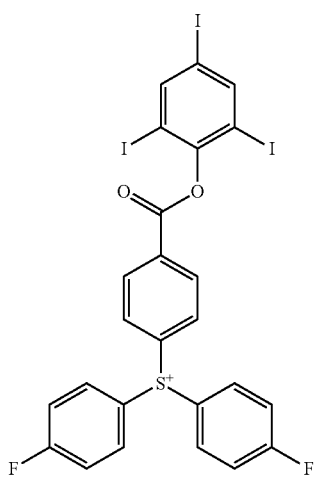
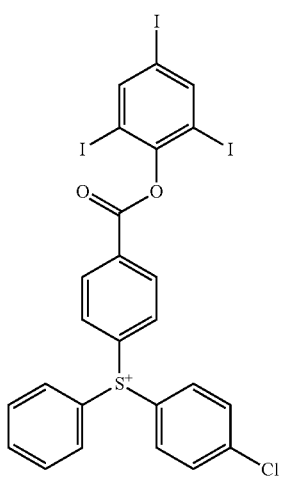
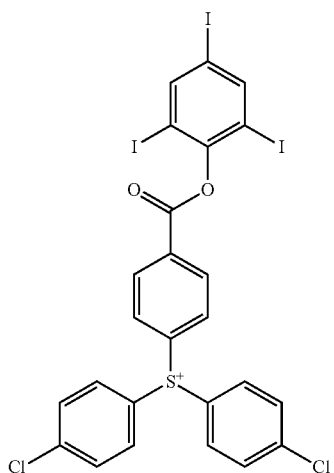
34
-continued
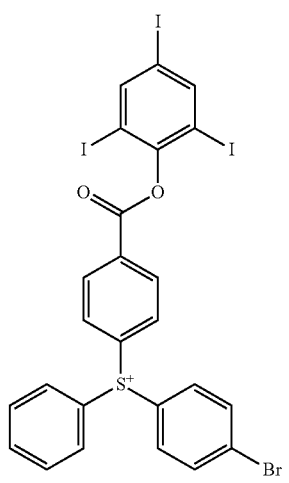
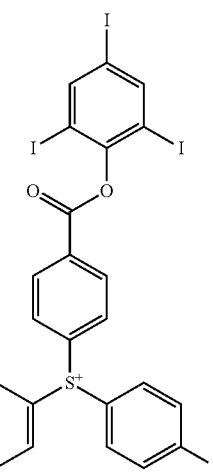
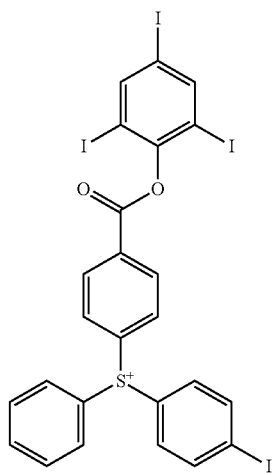

35
-continued
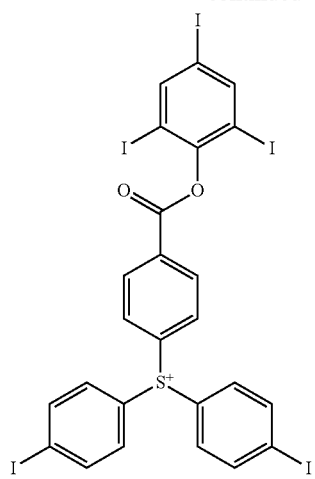
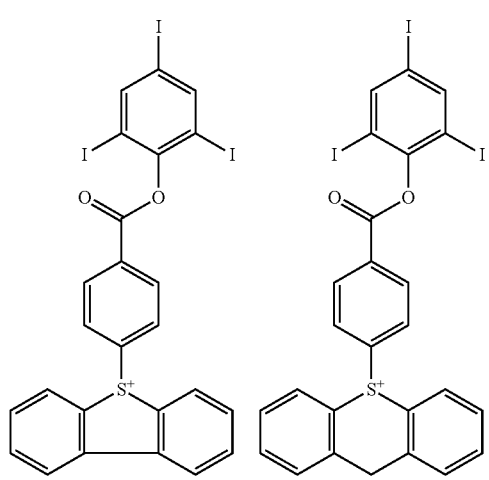
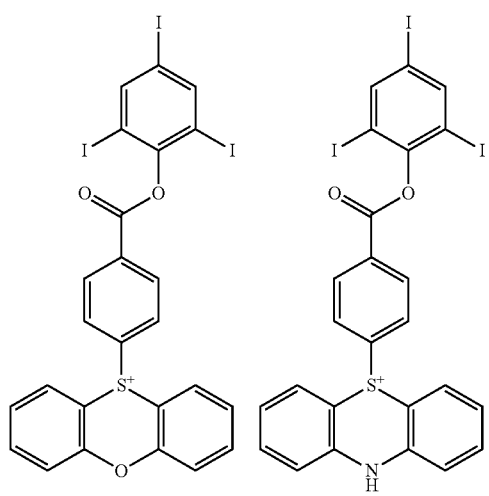
36
-continued
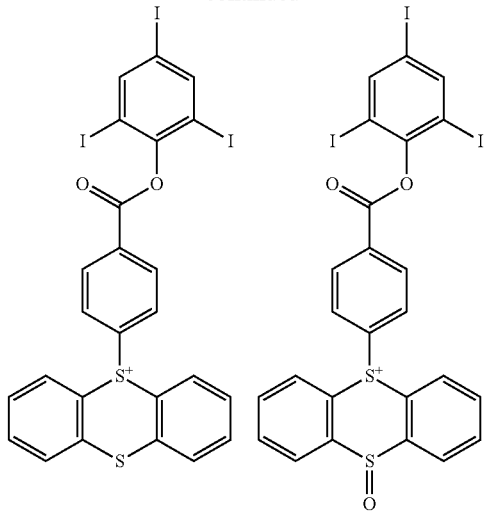
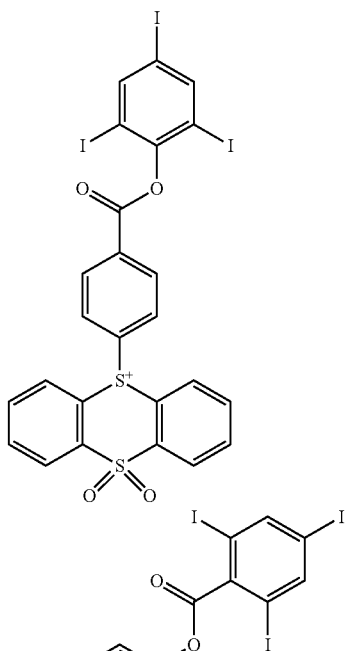
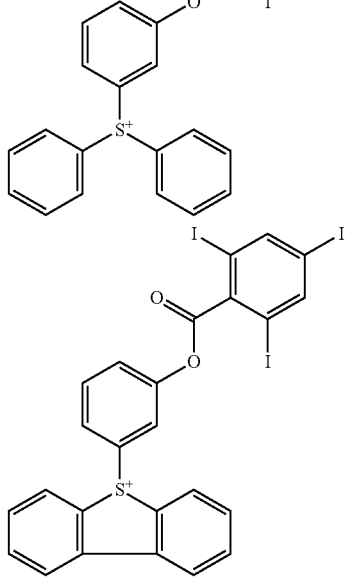

37
-continued
38
-continued
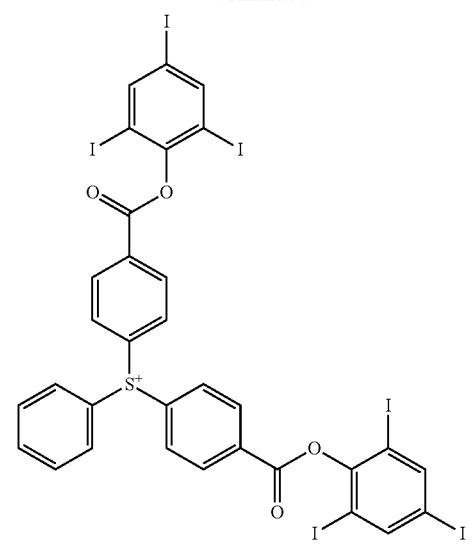
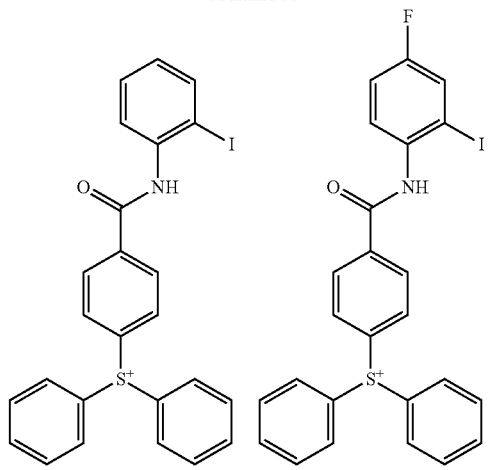
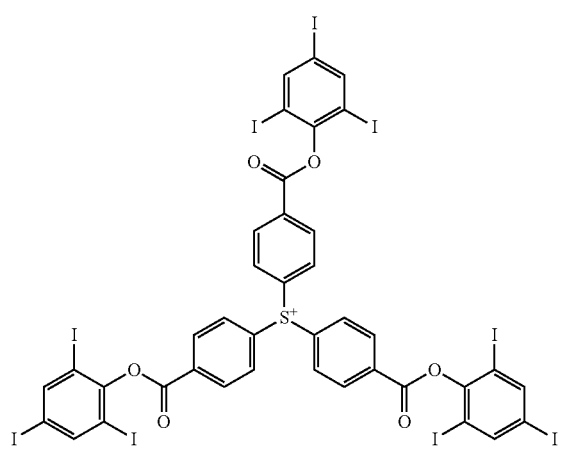
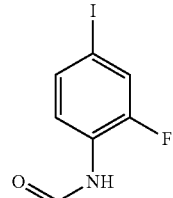
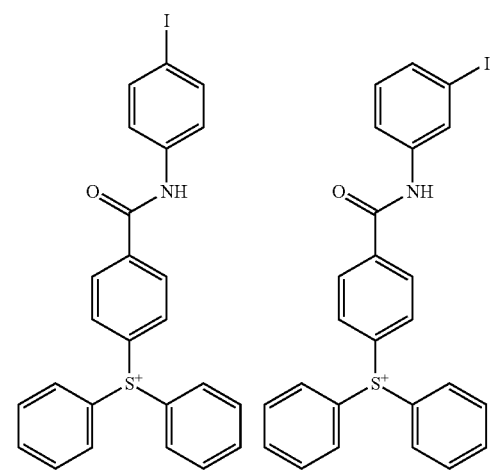
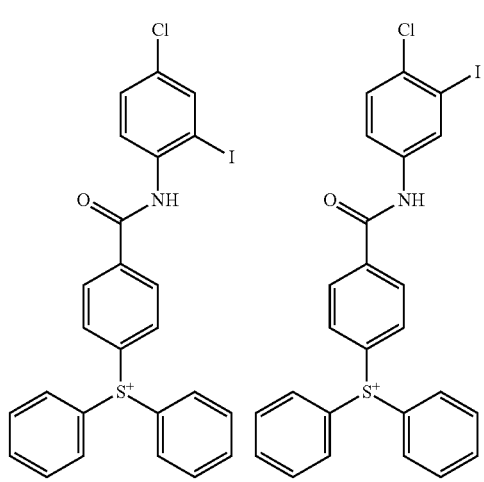

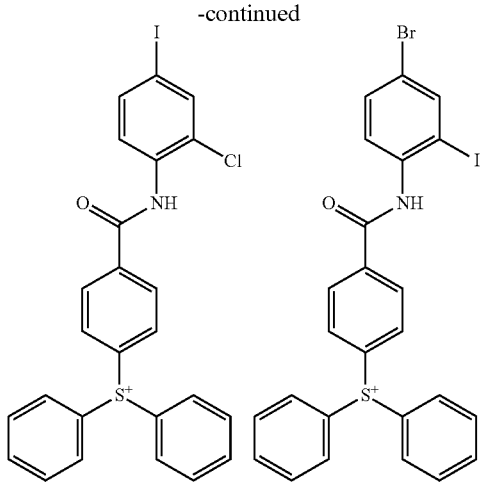
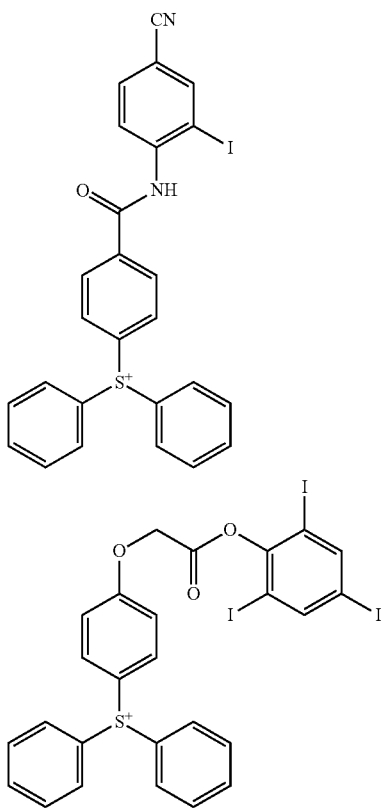
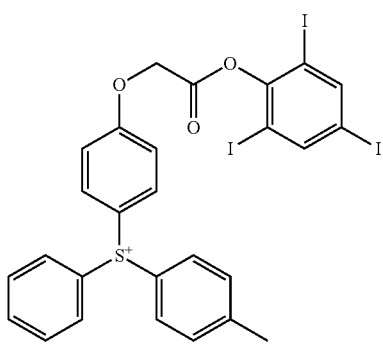
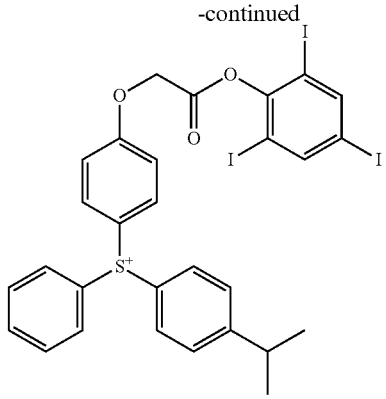
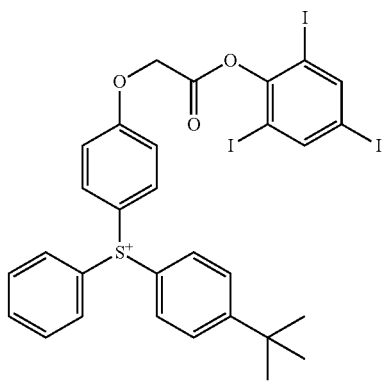
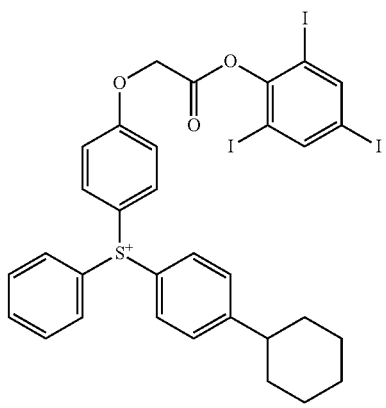
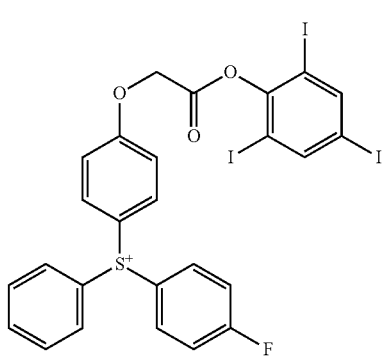

-continued
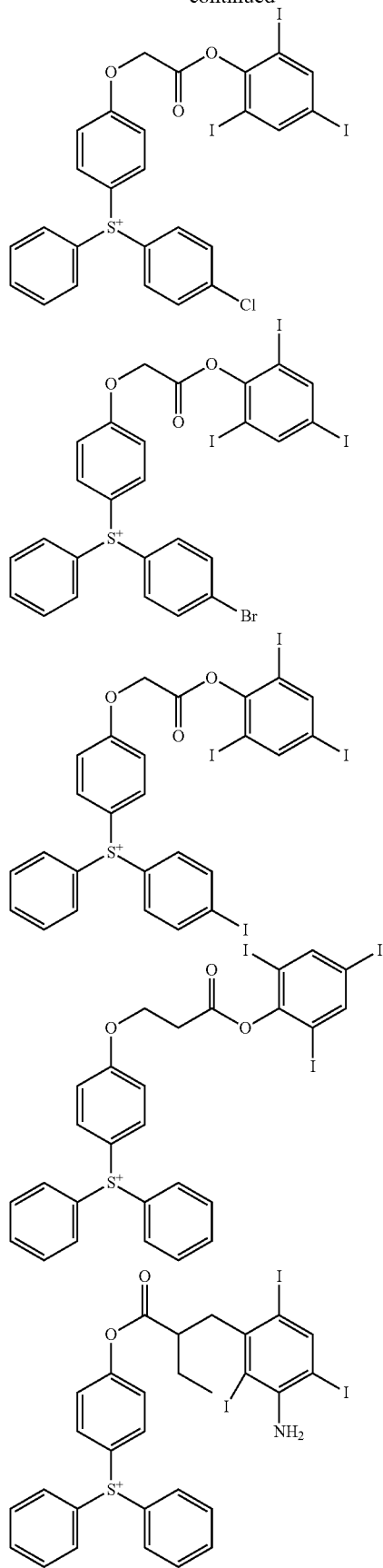
-continued
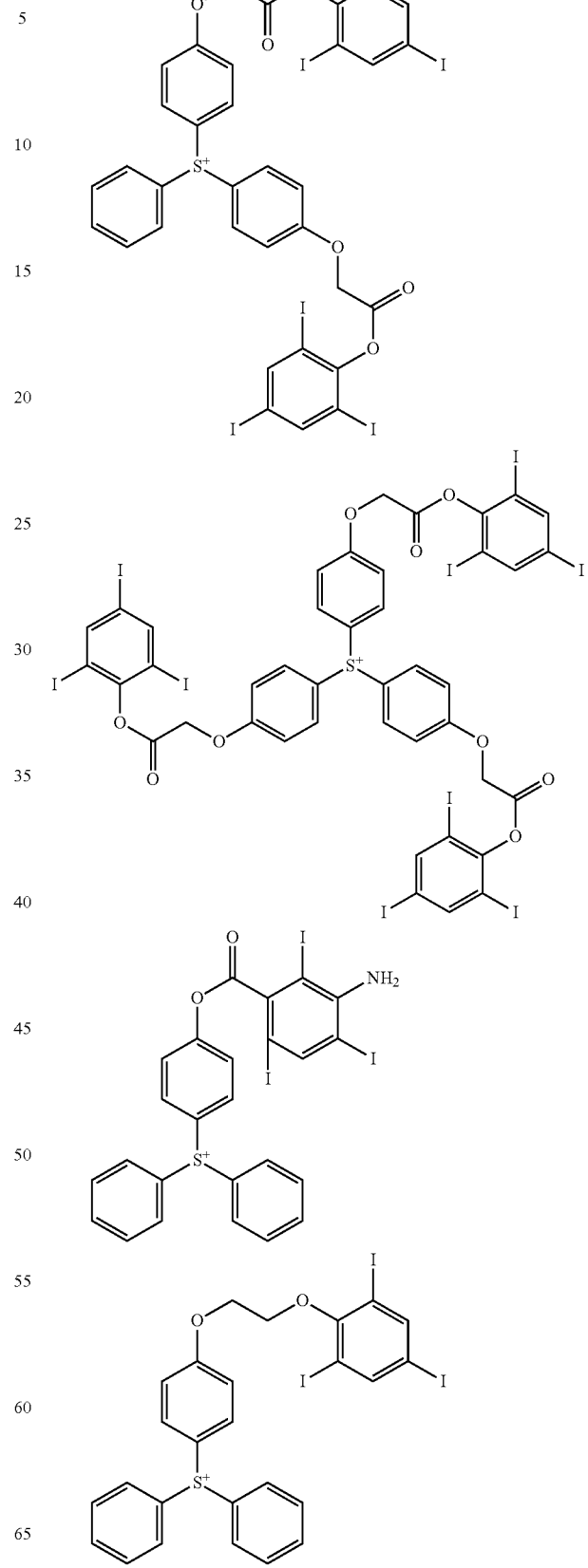

43
-continued
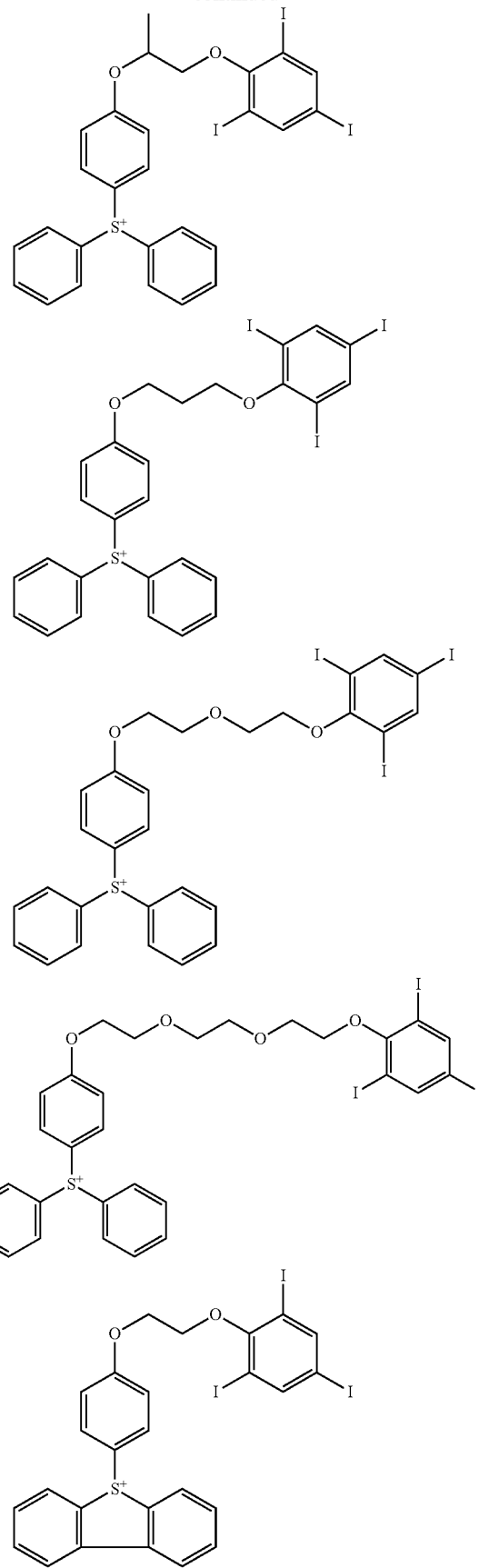
44
-continued
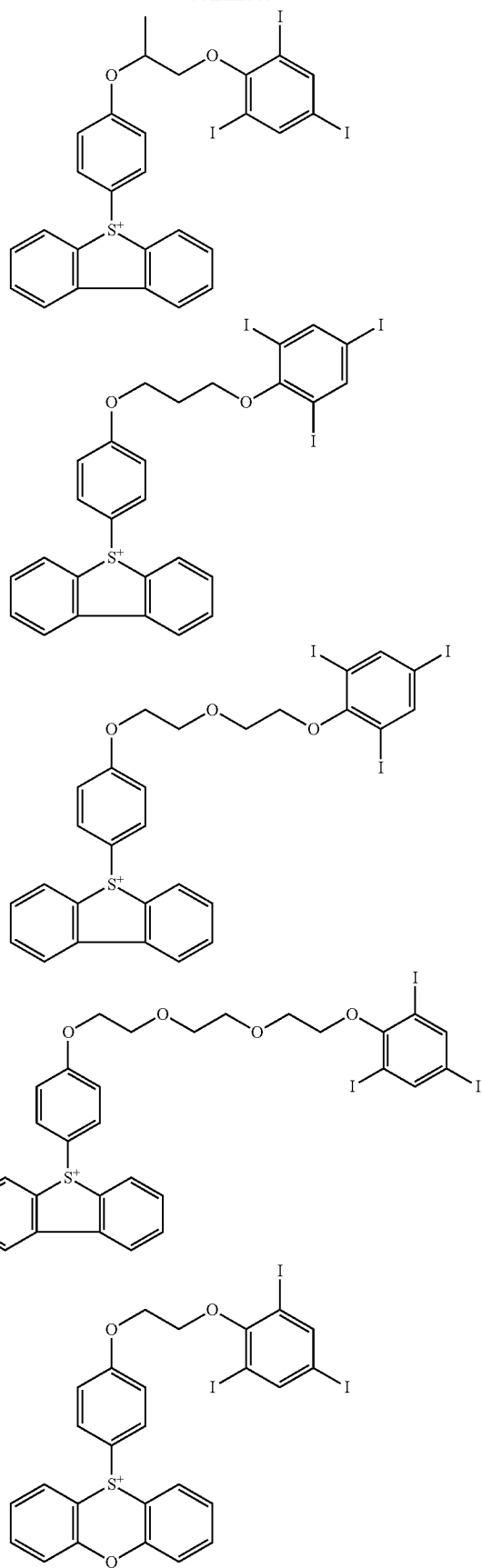

-continued
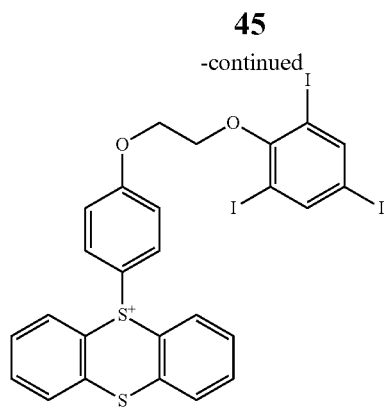
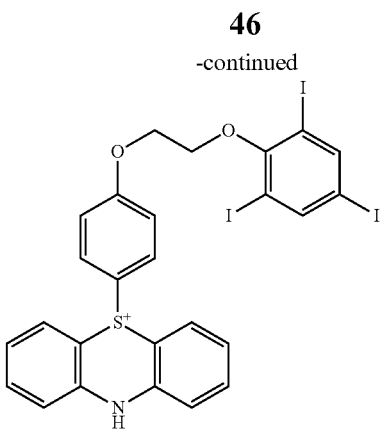
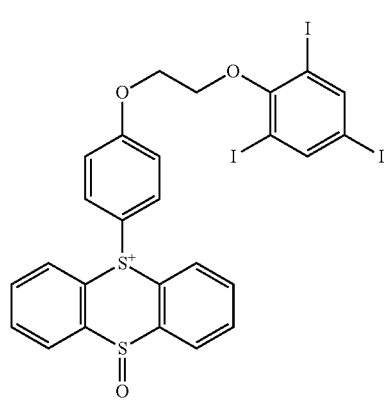
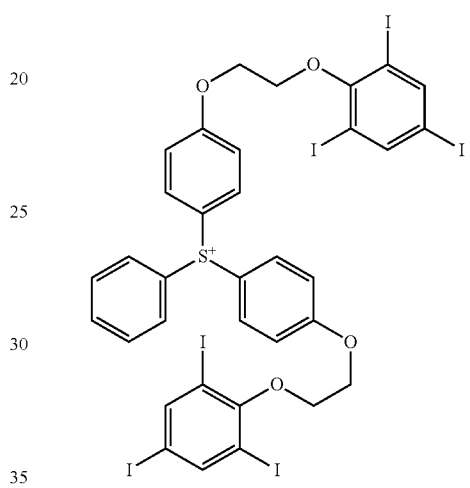
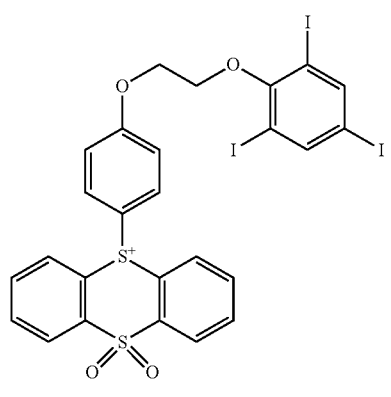
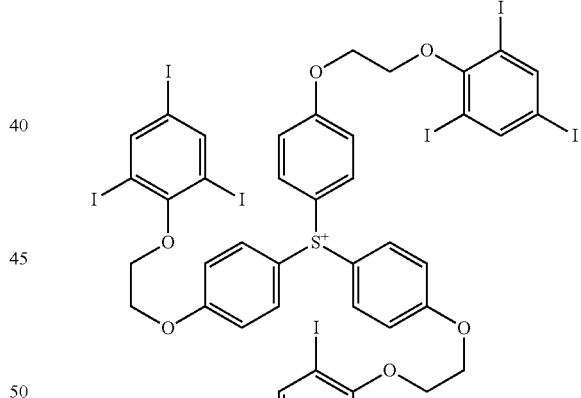
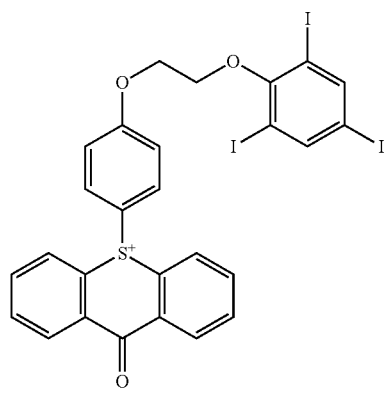
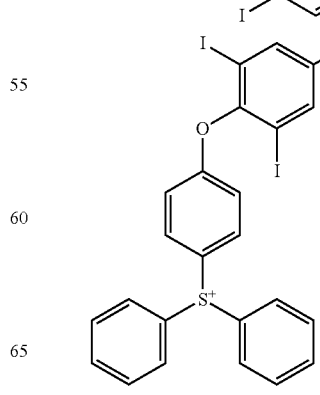

47
-continued
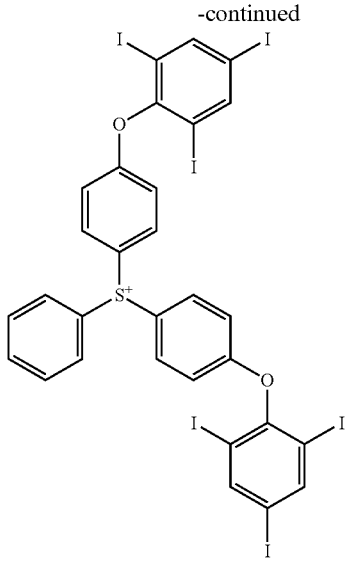
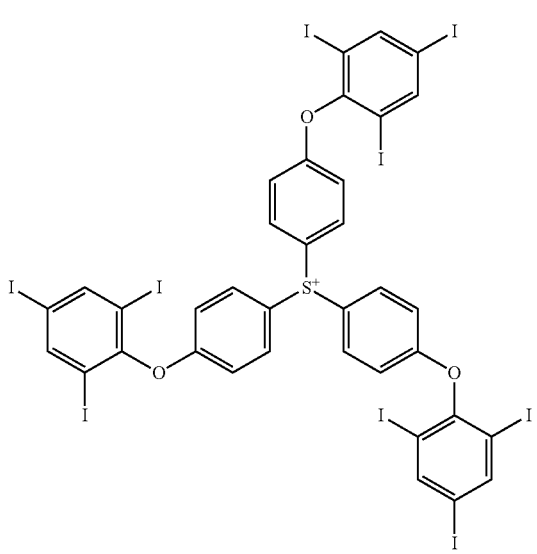
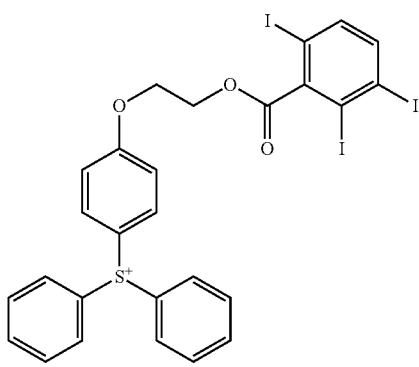
48
-continued
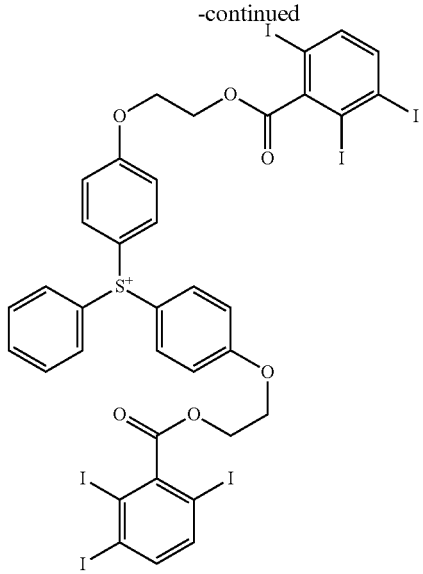
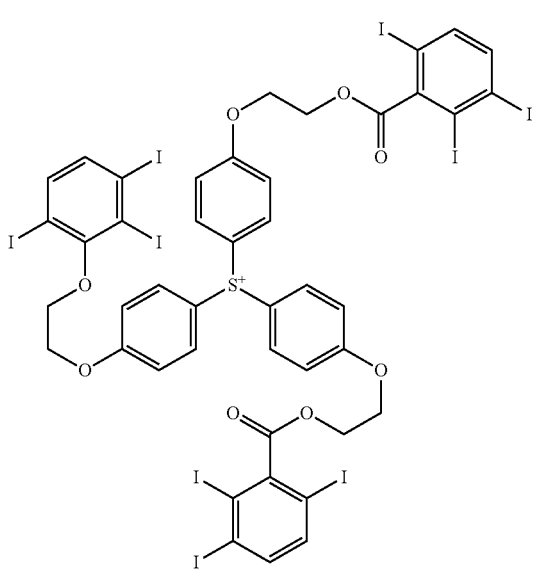
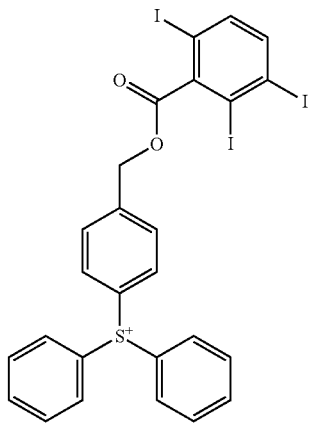

49
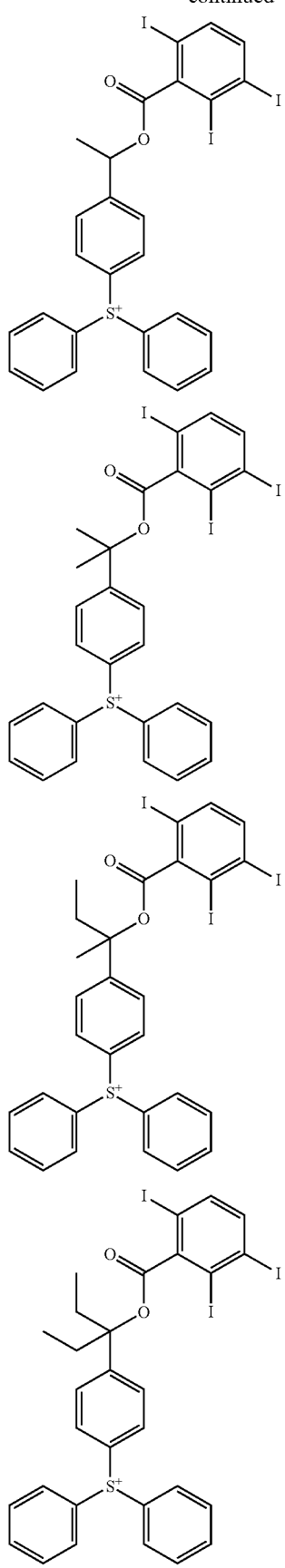
50
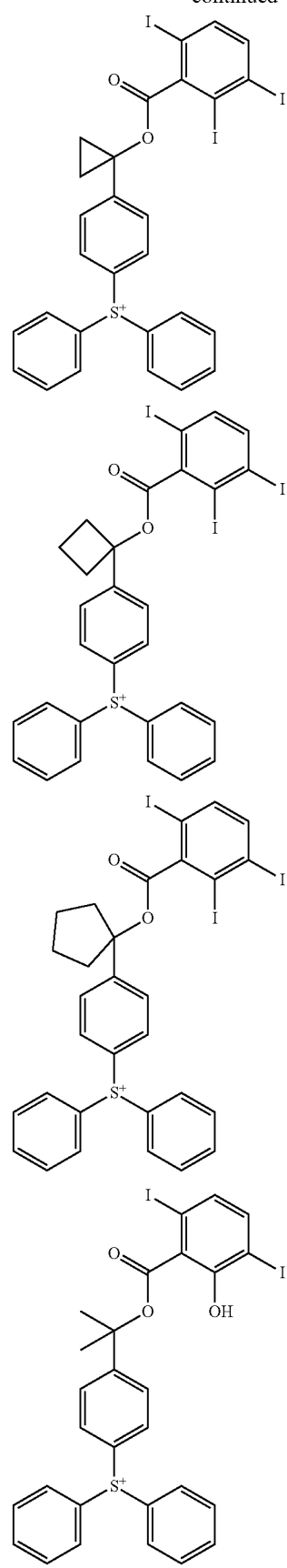

51
-continued
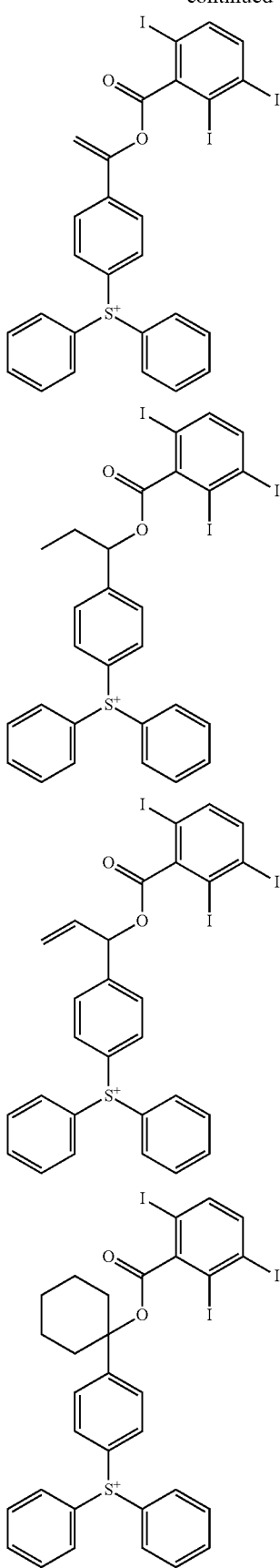
52
-continued
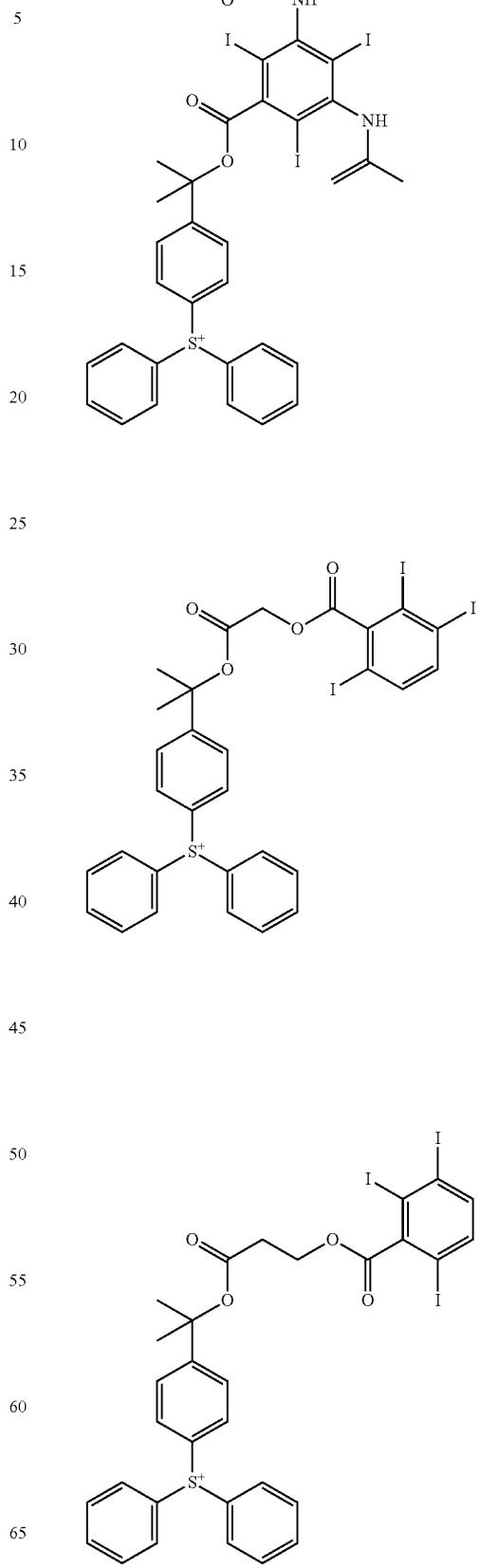

53
-continued
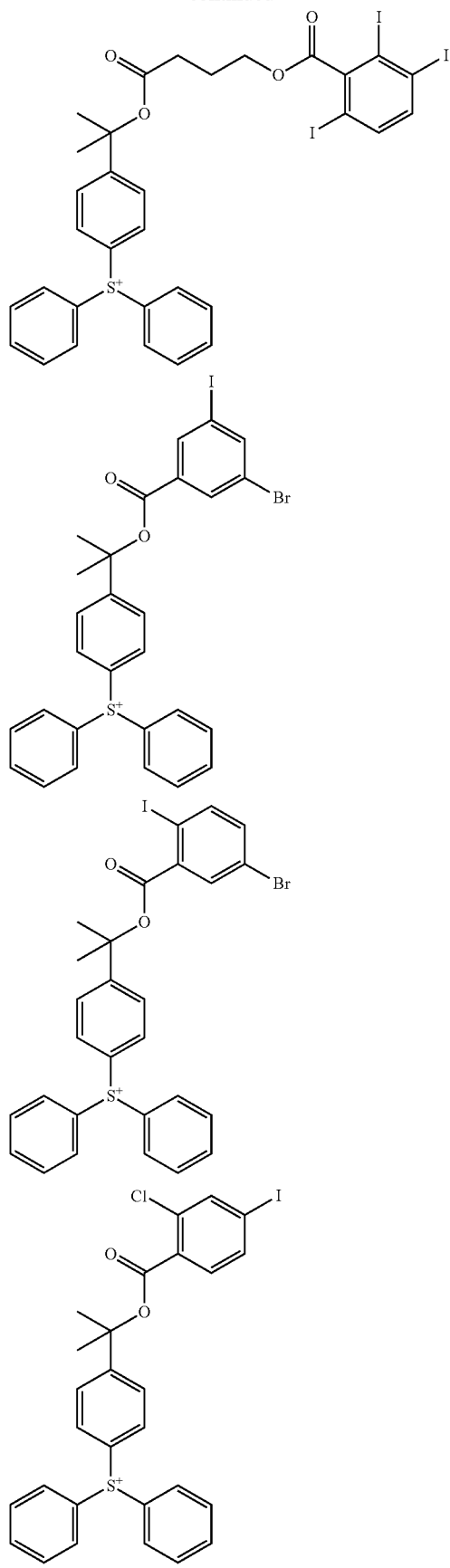
54
-continued
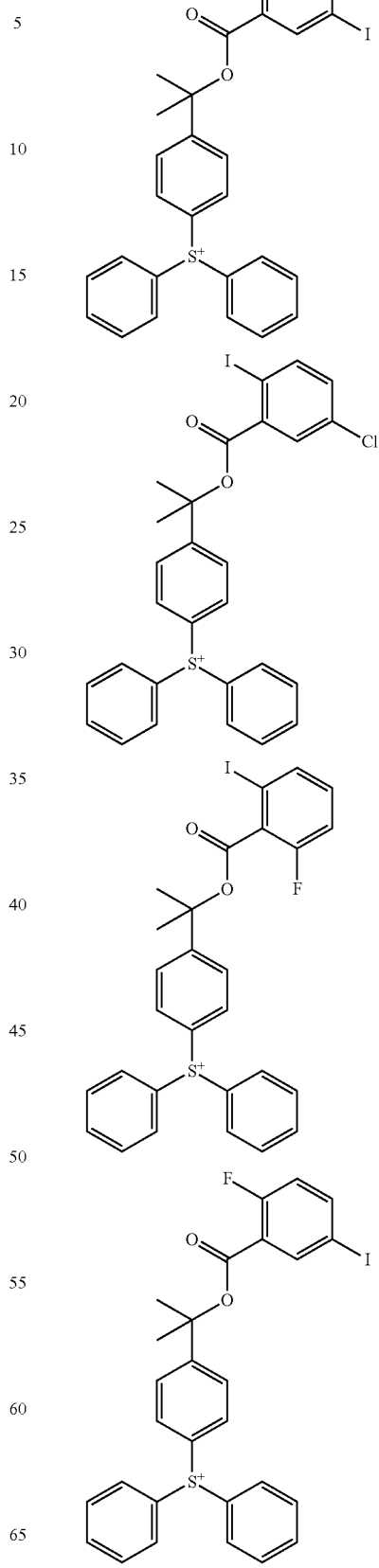

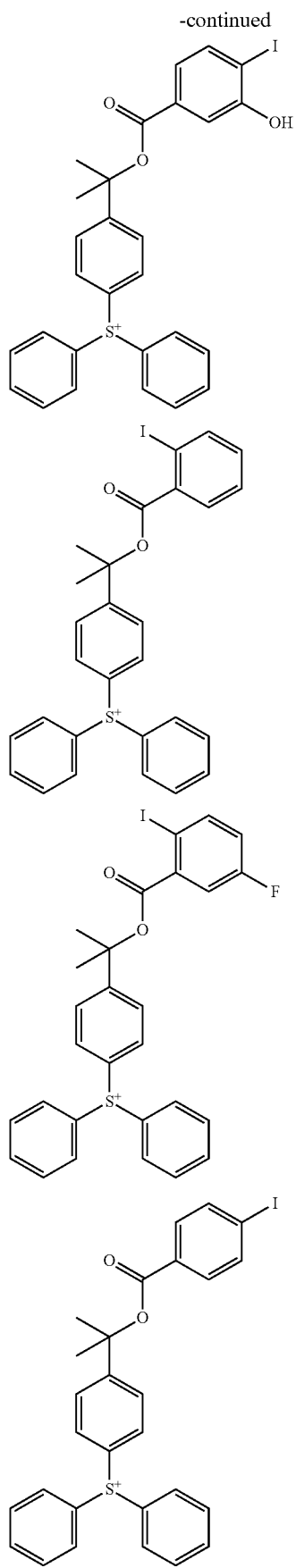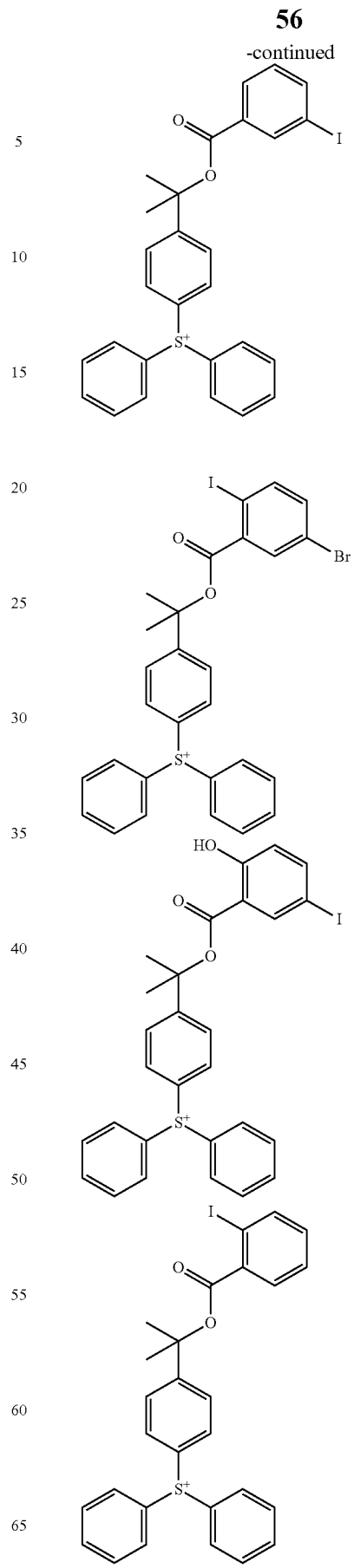

57
-continued
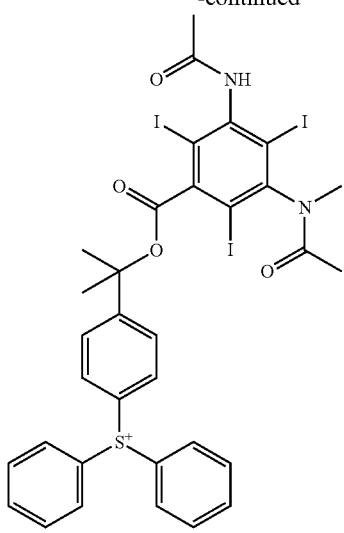
58
-continued
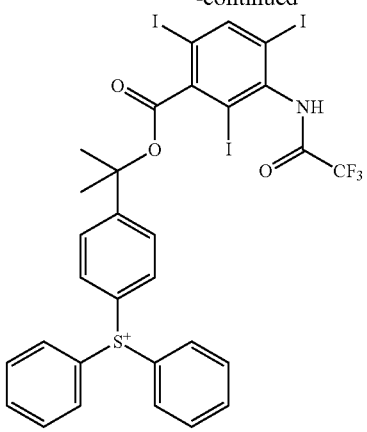
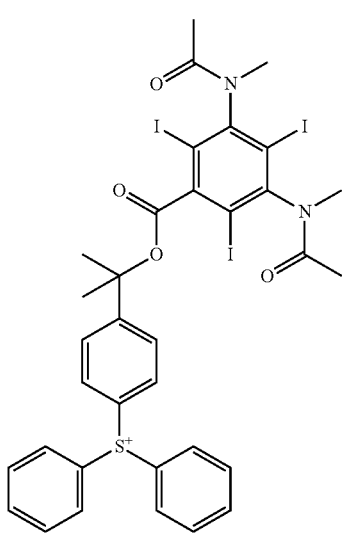
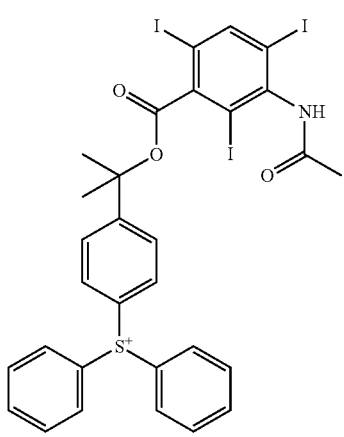
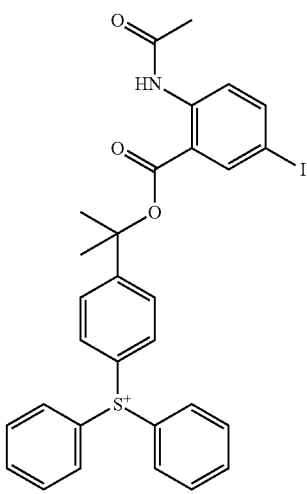

59
-continued
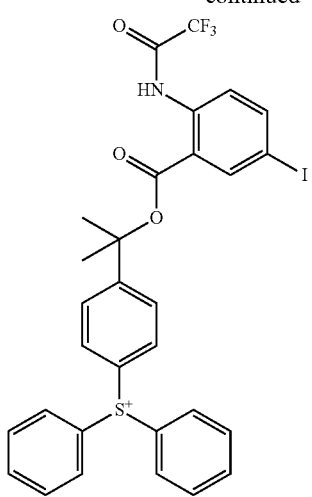
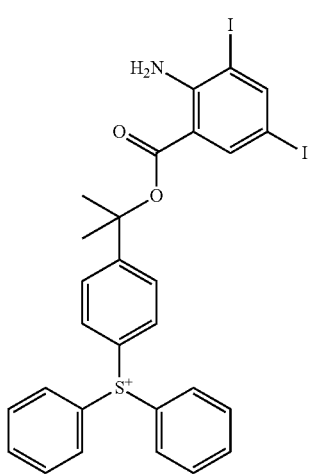
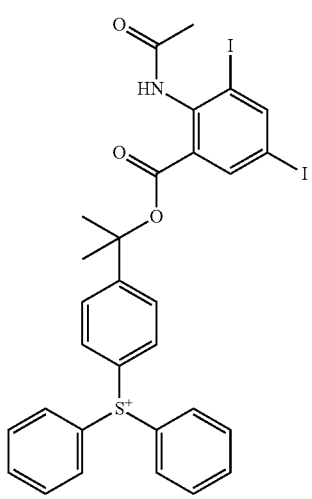
60
-continued
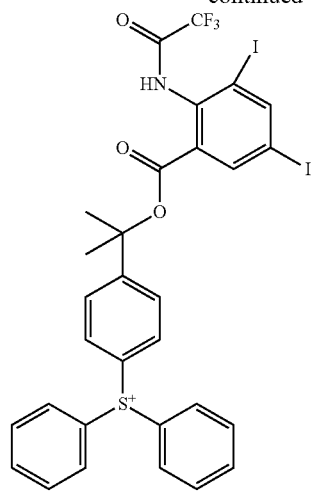
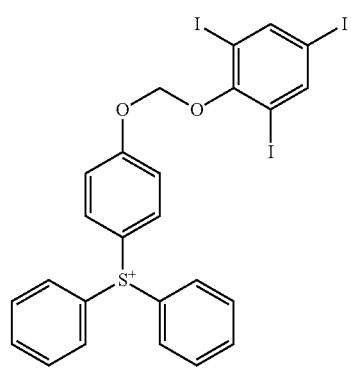
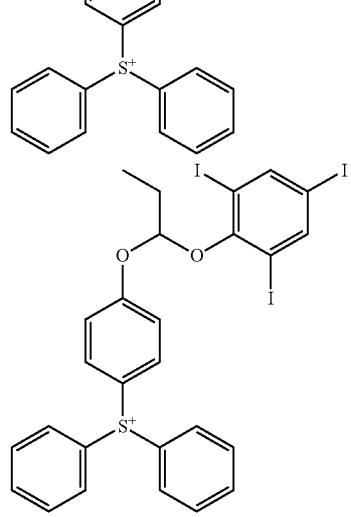

61
-continued
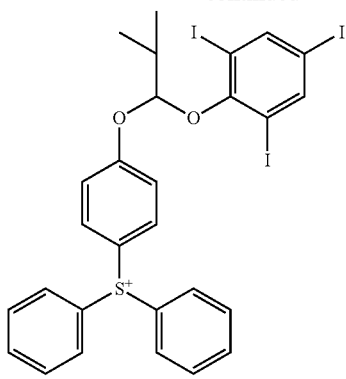
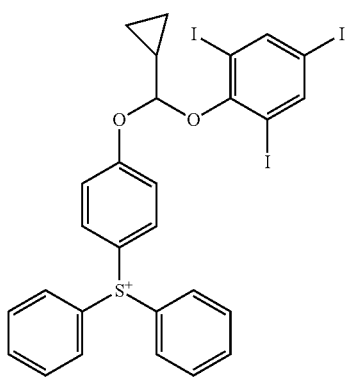
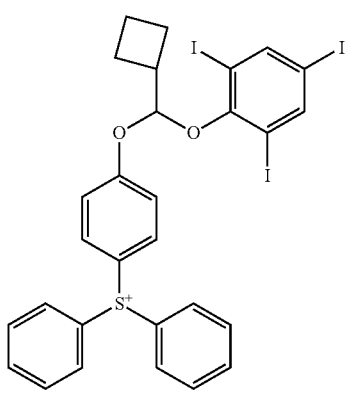
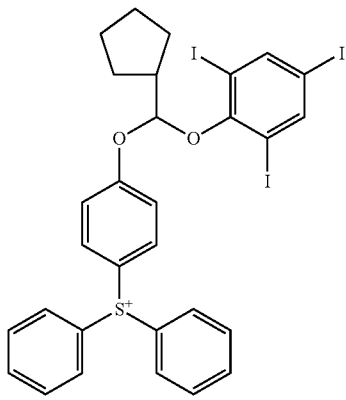
62
-continued
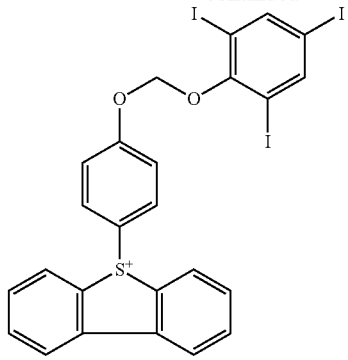
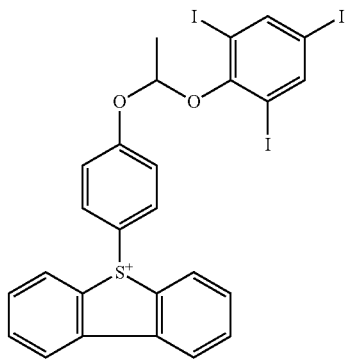
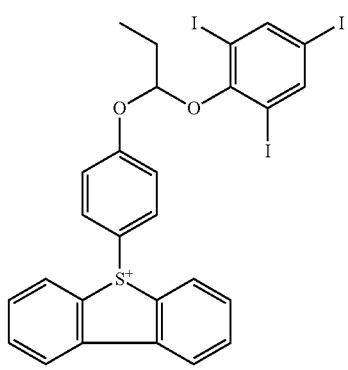
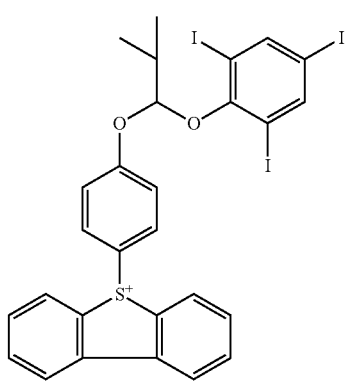

-continued
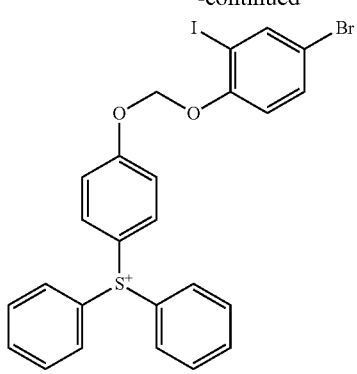
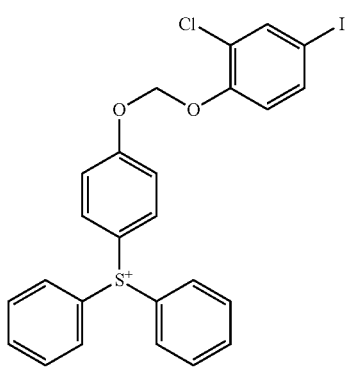
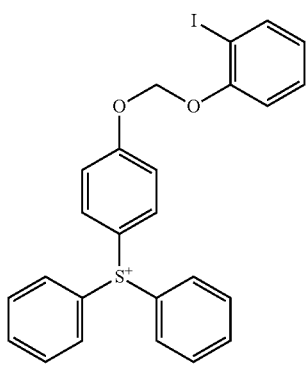
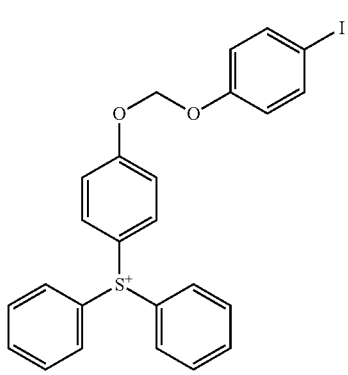
-continued
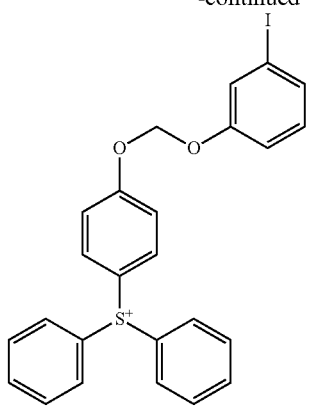
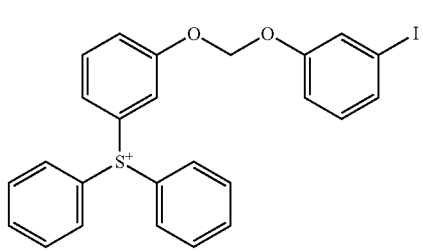
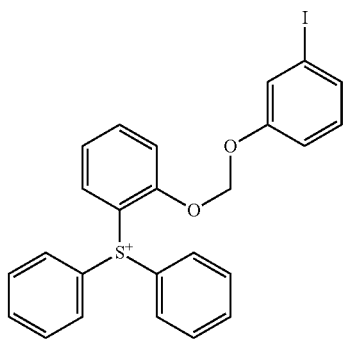
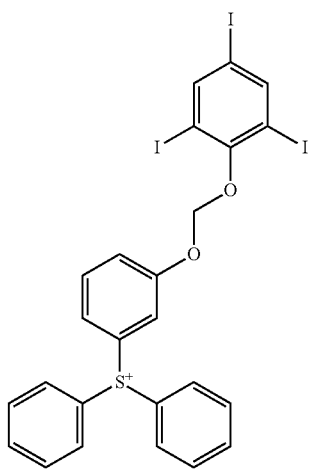

-continued
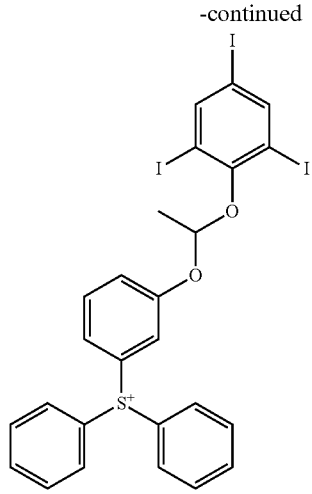
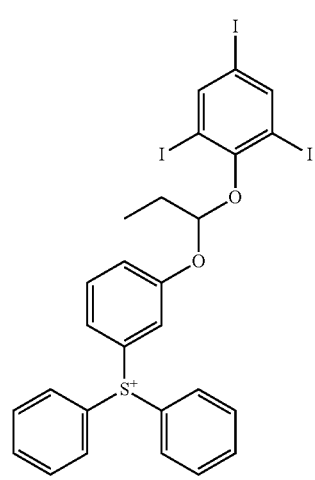
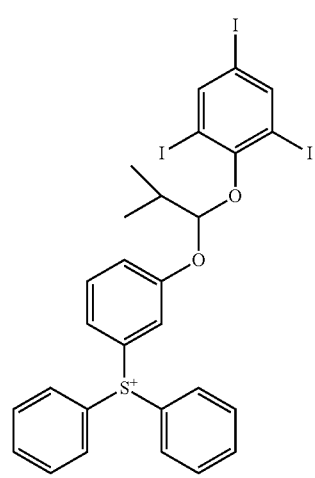
-continued
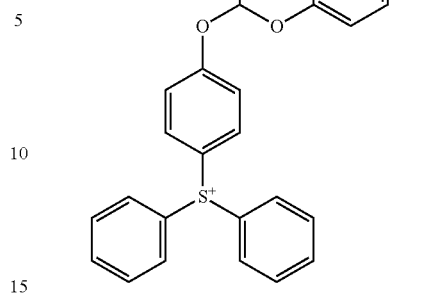
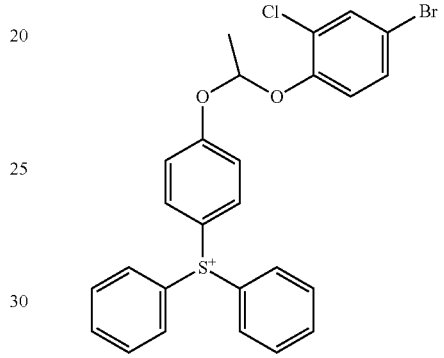
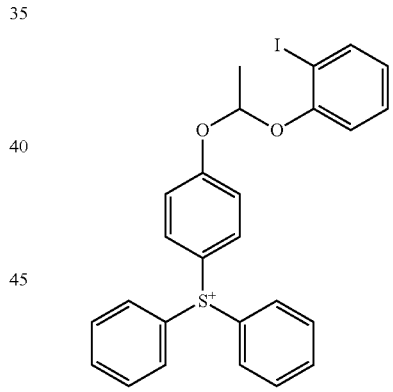
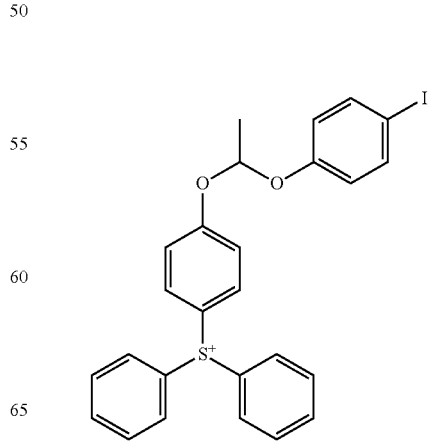

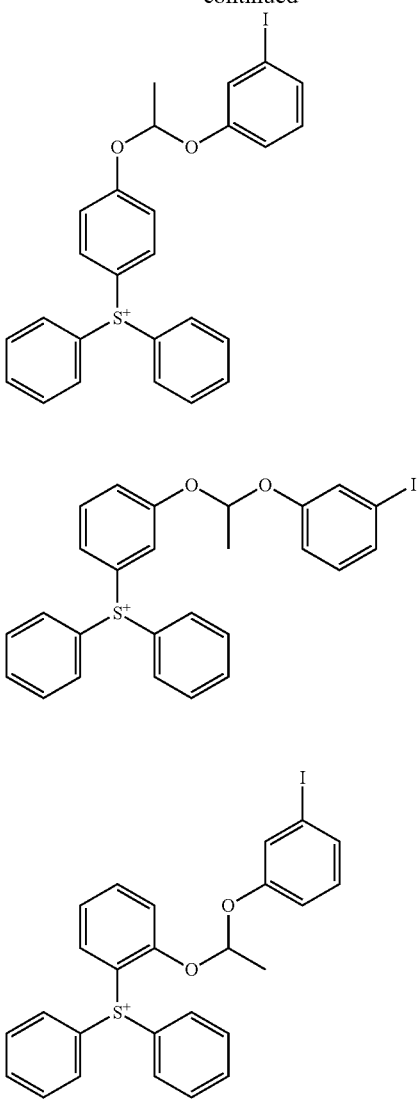

The sulfonium salt having formula (1) may be synthesized, for example, by subjecting a benzene ring-bearing sulfonium salt to esterification, etherification or amidation on its benzene ring using an iodized benzoic acid, phenol or aniline.

A resist composition comprising the sulfonium salt having formula (1) according to the invention may be processed to form a pattern even when it does not contain a base polymer. The sulfonium salt may be blended with a base polymer. In this embodiment, it is preferred from the aspects of sensitivity and acid diffusion suppressing effect that the amount of the sulfonium salt having formula (1) be 0.01 to 1,000 parts by weight, more preferably 0.05 to 500 parts by weight per 100 parts by weight of the base polymer.

Base Polymer

Where the resist composition is of positive tone, the resist composition comprises a base polymer comprising recurring units containing an acid labile group, preferably recurring units having the formula (a1) or recurring units having the formula (a2). These units are simply referred to as recurring units (a1) and (a2), hereinafter.

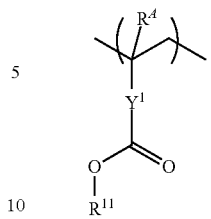

(a1)

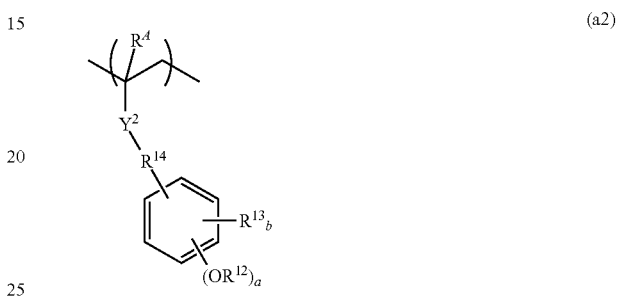

(a2)

In formulae (a1) and (a2), $R^A$ is each independently hydrogen or methyl. $Y^1$ is a single bond, phenylene group, naphthylene group, or a $C_1$-$C_{12}$ linking group containing an ester bond or lactone ring. $Y^2$ is a single bond or ester bond. $R^{11}$ and $R^{12}$ each are an acid labile group. $R^{13}$ is fluorine, trifluoromethyl, cyano, a $C_1$-$C_6$ alkyl group, $C_1$-$C_6$ alkoxy group, $C_2$-$C_7$ acyl group, $C_2$-$C_7$ acyloxy group, or $C_2$-$C_7$ alkoxycarbonyl group. $R^{14}$ is a single bond or a $C_1$-$C_6$ straight or branched alkanediyl group in which some carbon may be replaced by an ether bond or ester bond, a is 1 or 2, b is an integer of 0 to 4, the sum of a+b is 1 to 5.

Examples of the monomer from which recurring units (a1) are derived are shown below, but not limited thereto. Herein $R^A$ and $R^{11}$ are as defined above.

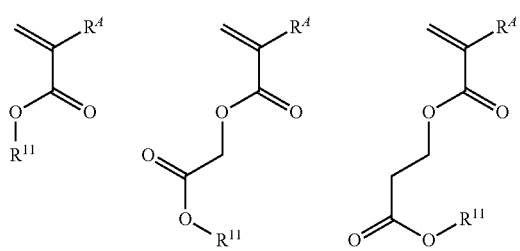

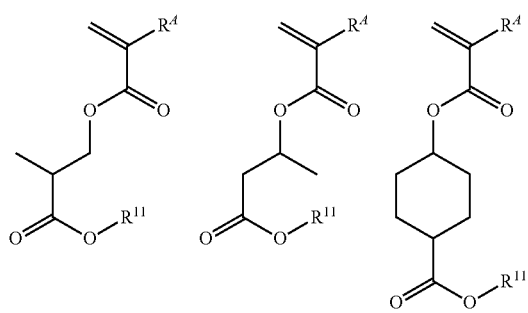

-continued

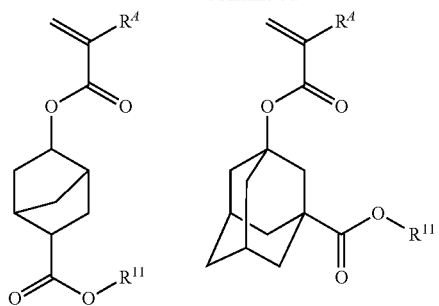
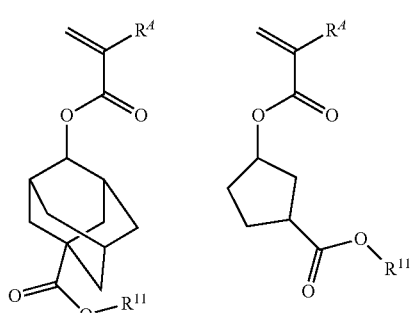
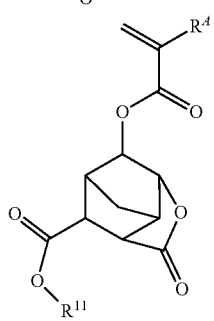
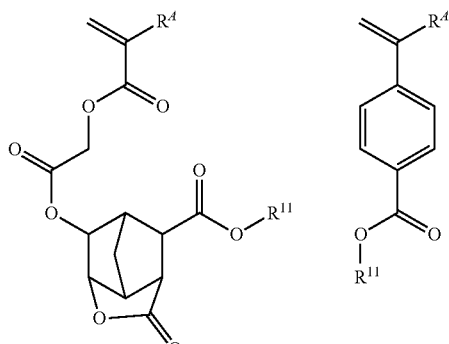
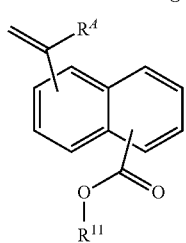

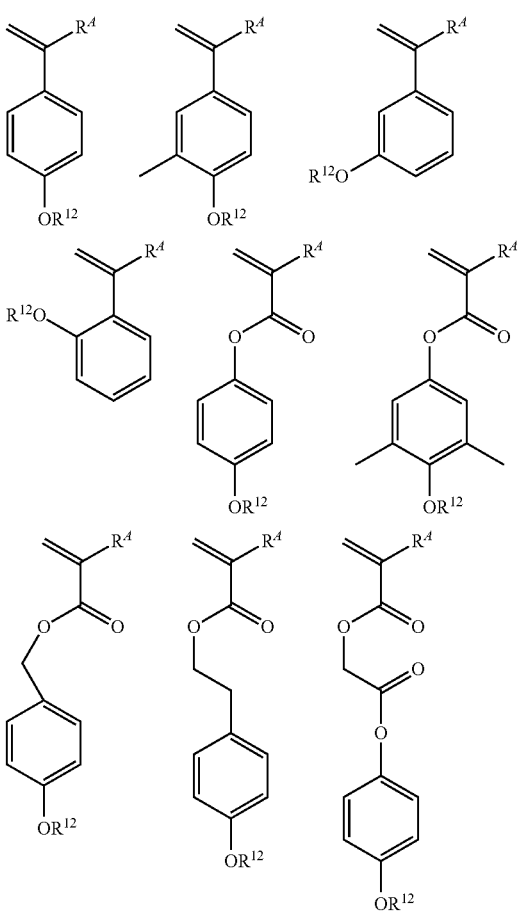

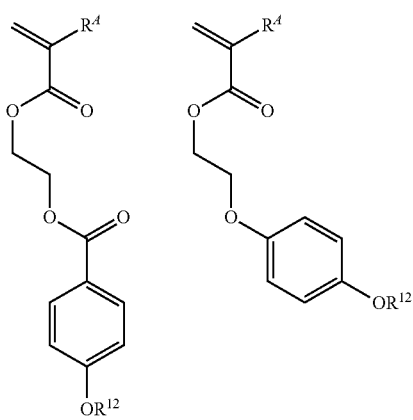

The acid labile groups represented by $R^{11}$ and $R^{12}$ in formulae (a1) and (a2) may be selected from a variety of such groups, for example, those groups described in JP-A 2013-080033 (U.S. Pat. No. 8,574,817) and JP-A 2013-083821 (U.S. Pat. No. 8,846,303).

Typical of the acid labile group are groups of the following formulae (AL-1) to (AL-3).

(AL-1)

Examples of the monomer from which recurring units (a2) are derived are shown below, but not limited thereto. Herein $R^A$ and $R^{12}$ are as defined above.

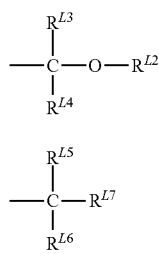

(AL-2)

(AL-3)

In formulae (AL-1) and (AL-2), $R^{L1}$ and $R^{L2}$ are each independently a $C_1$-$C_{40}$ monovalent hydrocarbon group which may contain a heteroatom such as oxygen, sulfur, nitrogen or fluorine. The monovalent hydrocarbon groups may be straight, branched or cyclic, with alkyl groups of 1 to 40 carbon atoms, especially 1 to 20 carbon atoms being preferred. In formula (AL-1), c is an integer of 0 to 10, especially 1 to 5.

In formula (AL-2), $R^{L3}$ and $R^{L4}$ are each independently hydrogen or a $C_1$-$C_{20}$ monovalent hydrocarbon group which may contain a heteroatom such as oxygen, sulfur, nitrogen or fluorine. The monovalent hydrocarbon groups may be straight, branched or cyclic, with $C_1$-$C_{20}$ alkyl groups being preferred. Any two of $R^{L2}$, $R^{L3}$ and $R^{L4}$ may bond together to form a ring with the carbon atom or carbon and oxygen atoms to which they are attached. The ring contains 3 to 20 carbon atoms, preferably 4 to 16 carbon atoms, and is typically alicyclic.

In formula (AL-3), $R^{L5}$, $R^{L6}$ and $R^{L7}$ are each independently a $C_1$-$C_{20}$ monovalent hydrocarbon group which may contain a heteroatom such as oxygen, sulfur, nitrogen or fluorine. The monovalent hydrocarbon groups may be straight, branched or cyclic, with $C_1$-$C_{20}$ alkyl groups being preferred. Any two of $R^{L5}$, $R^{L6}$ and $R^{L7}$ may bond together to form a ring with the carbon atom to which they are attached. The ring contains 3 to 20 carbon atoms, preferably 4 to 16 carbon atoms and is typically alicyclic.

The base polymer may further comprise recurring units (b) having a phenolic hydroxyl group as an adhesive group. Examples of suitable monomers from which recurring units (b) are derived are given below, but not limited thereto. Herein $R^A$ is as defined above.

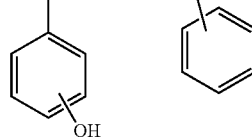

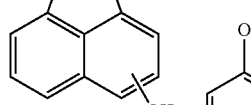

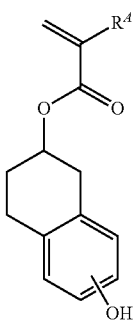

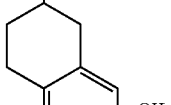

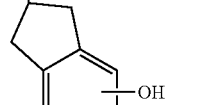

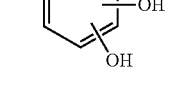

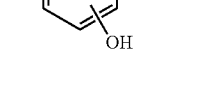

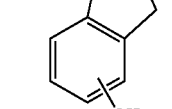

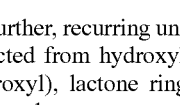

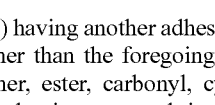

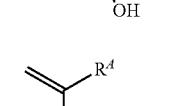

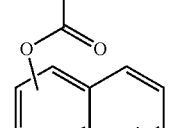

Further, recurring units (c) having another adhesive group selected from hydroxyl (other than the foregoing phenolic hydroxyl), lactone ring, ether, ester, carbonyl, cyano and carboxyl groups may also be incorporated in the base polymer. Examples of suitable monomers from which recurring units (c) are derived are given below, but not limited thereto. Herein $R^A$ is as defined above.

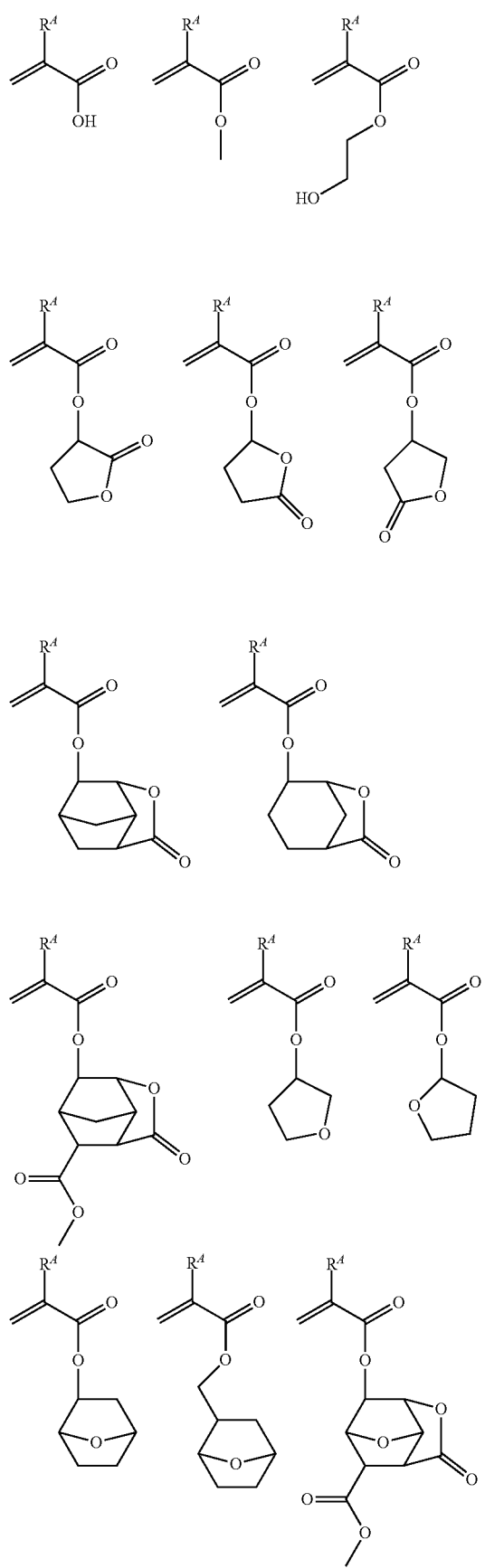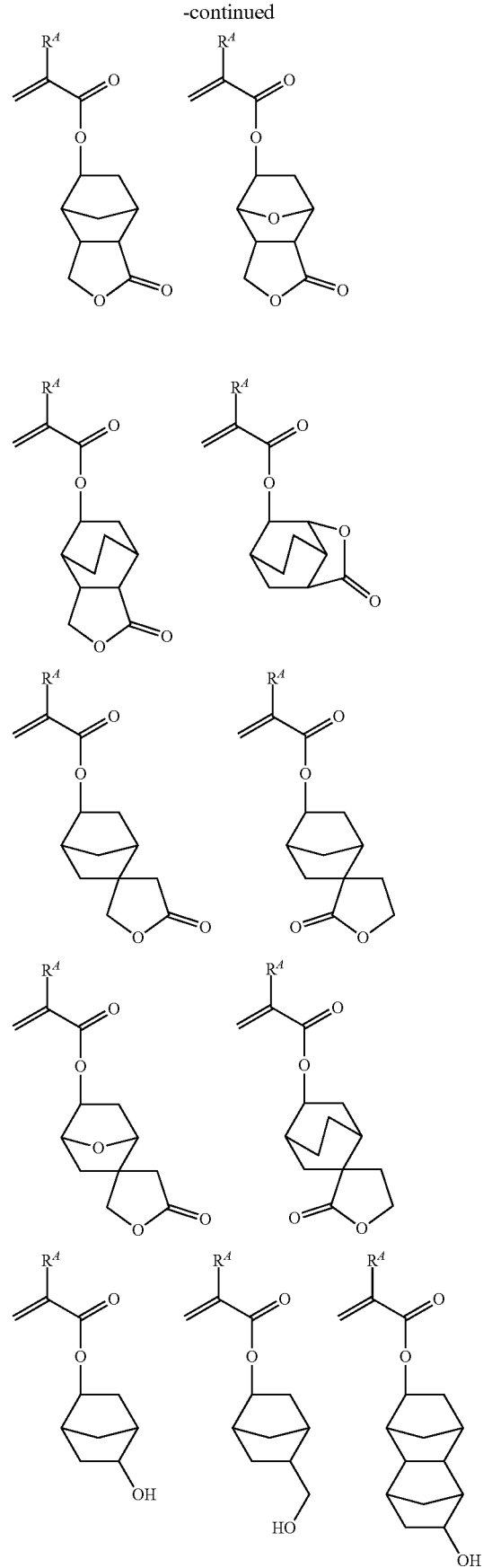
-continued

-continued

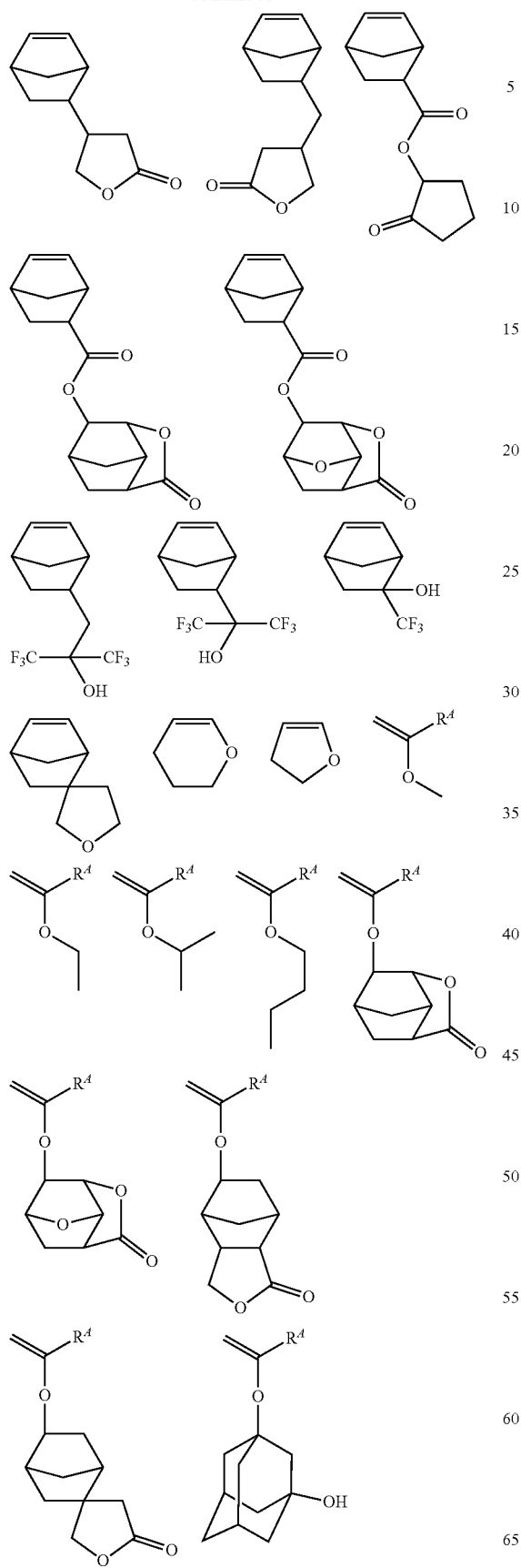
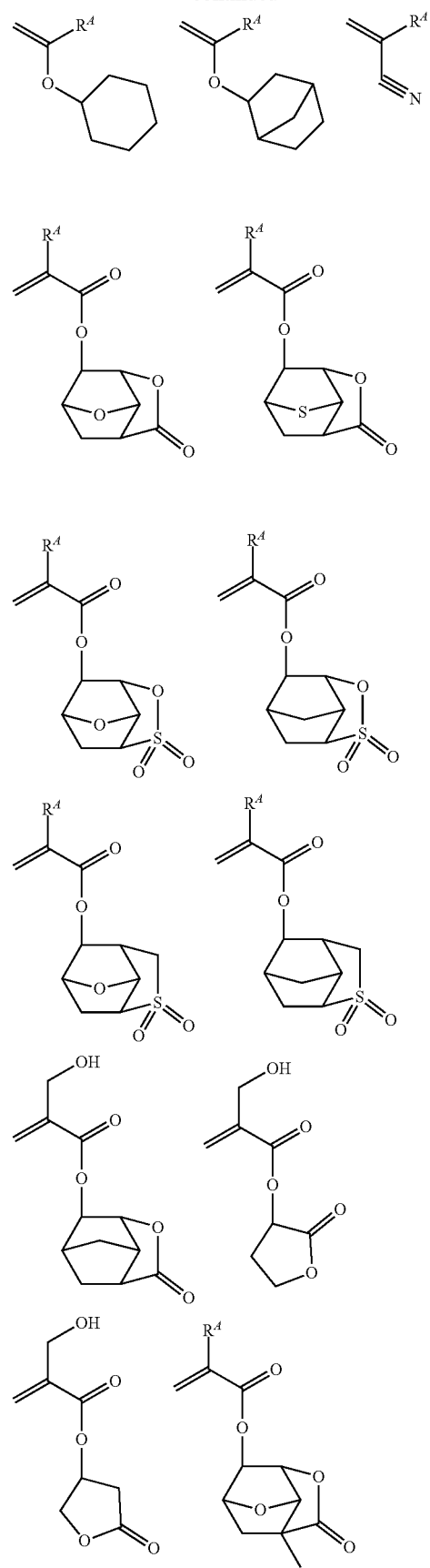

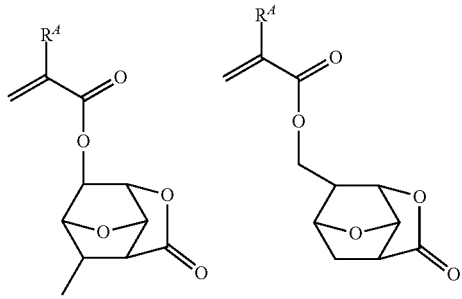
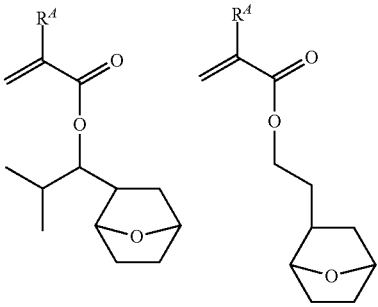
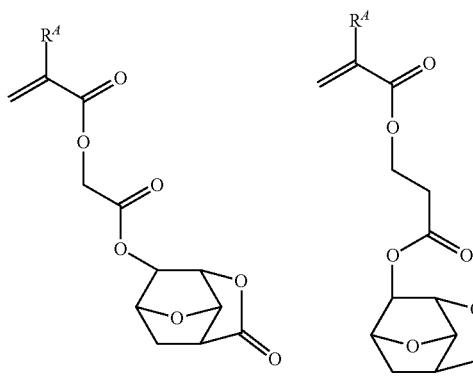
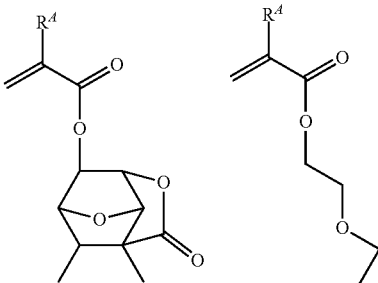
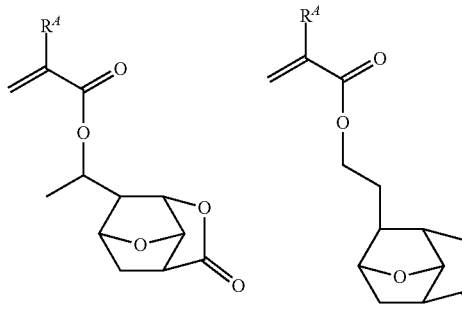
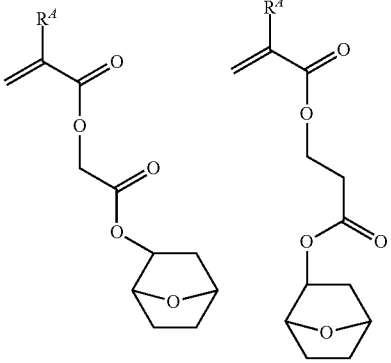
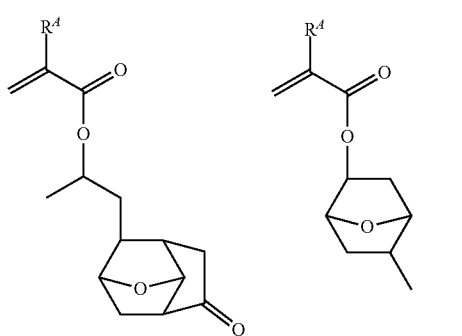
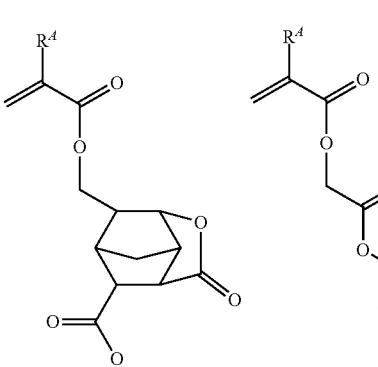

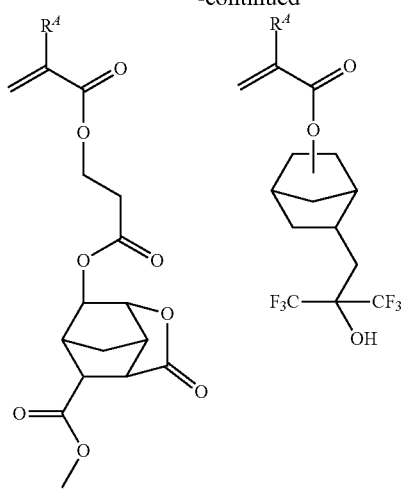
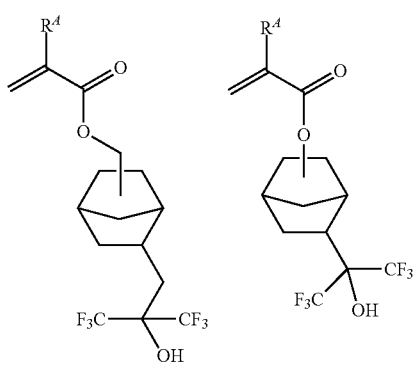
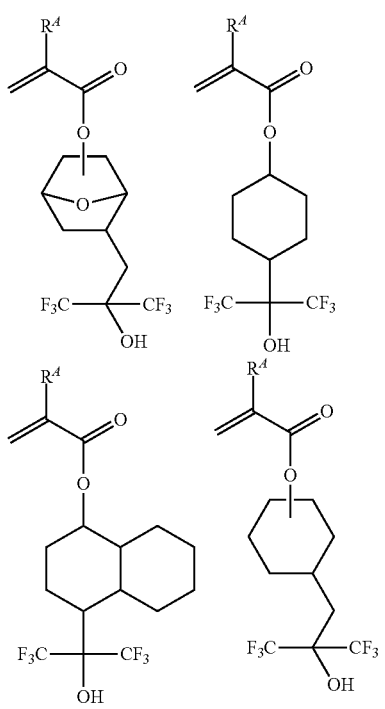
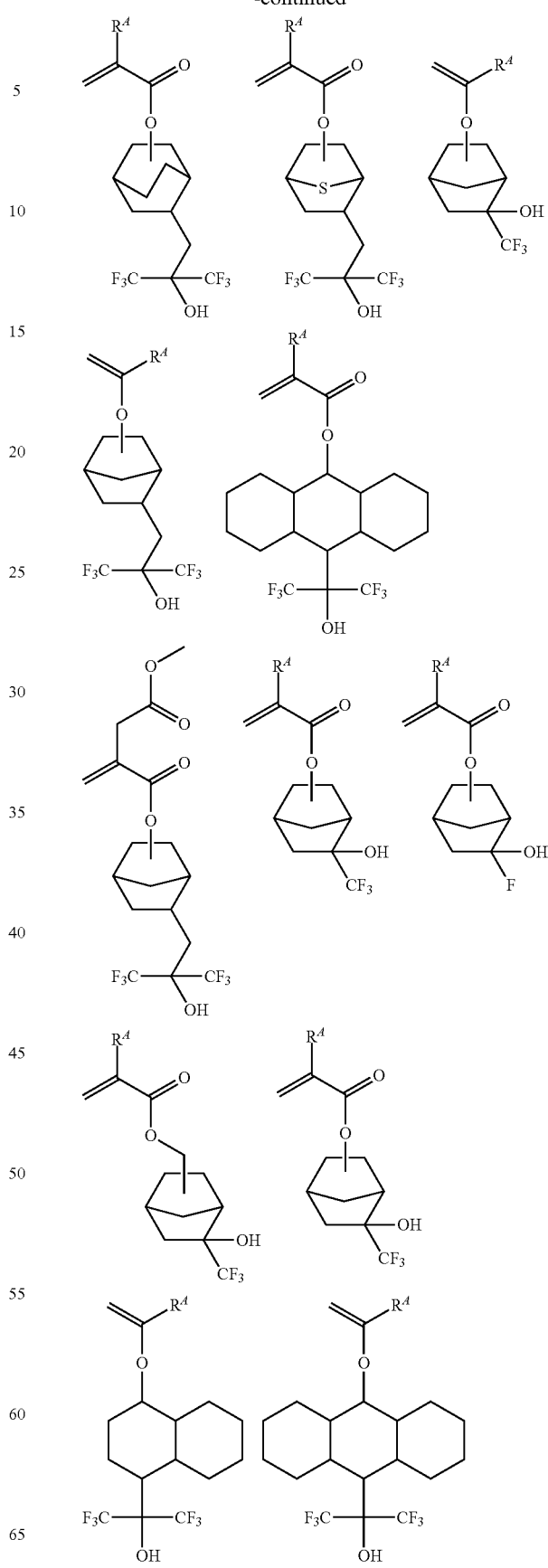

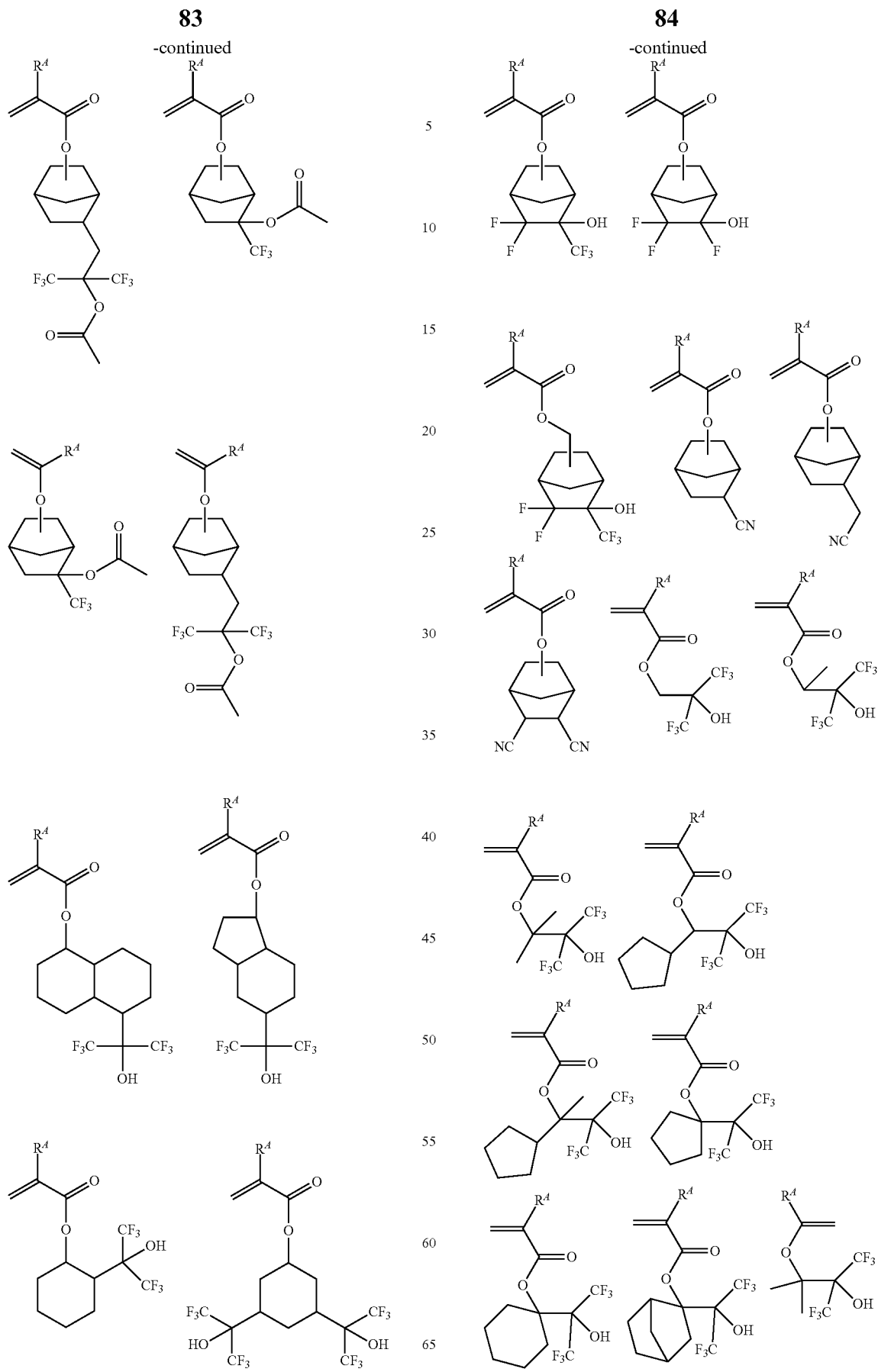

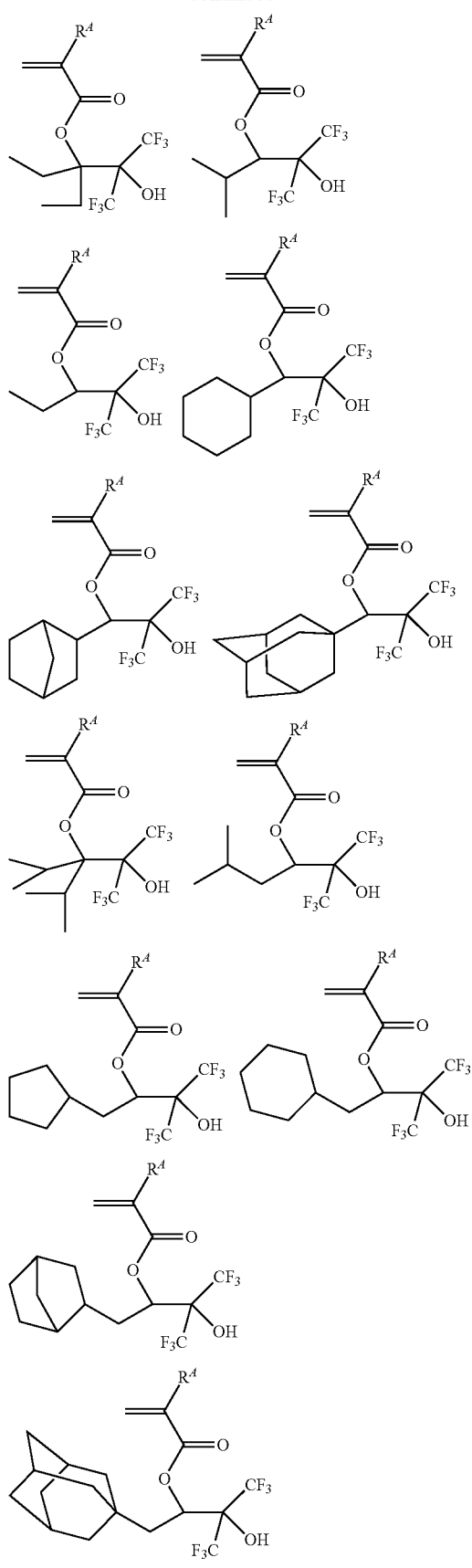
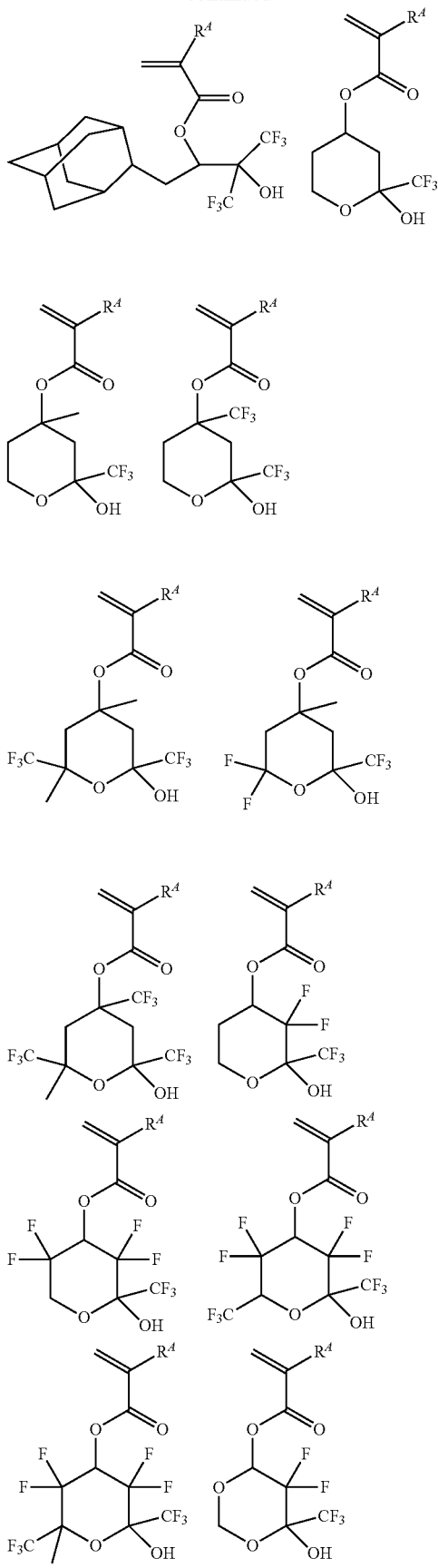

87
-continued
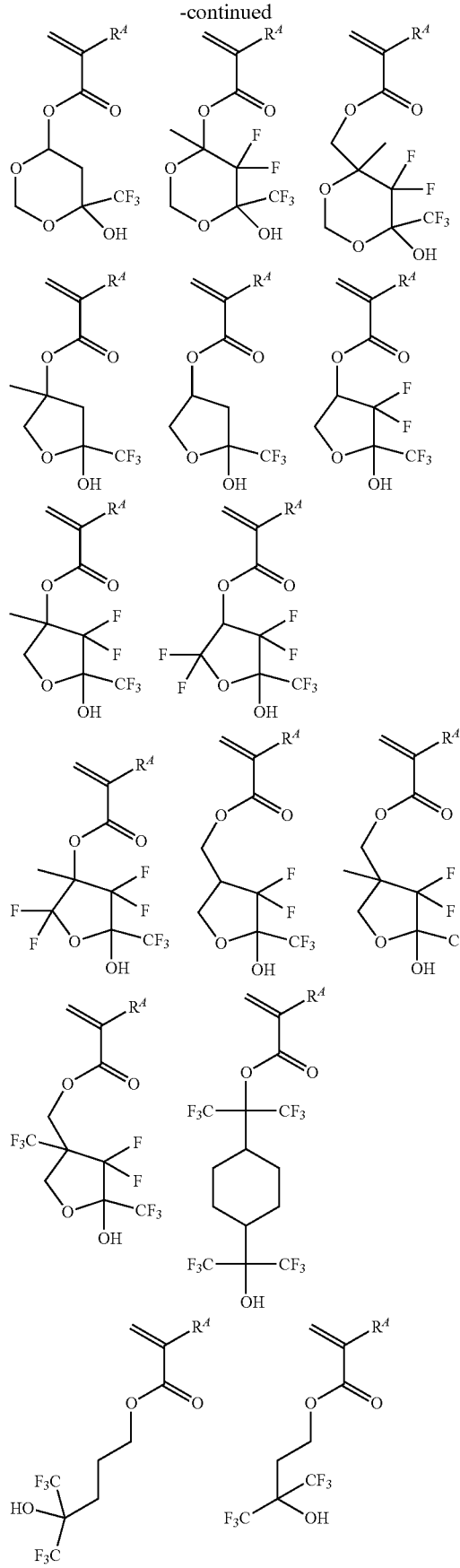
88
-continued
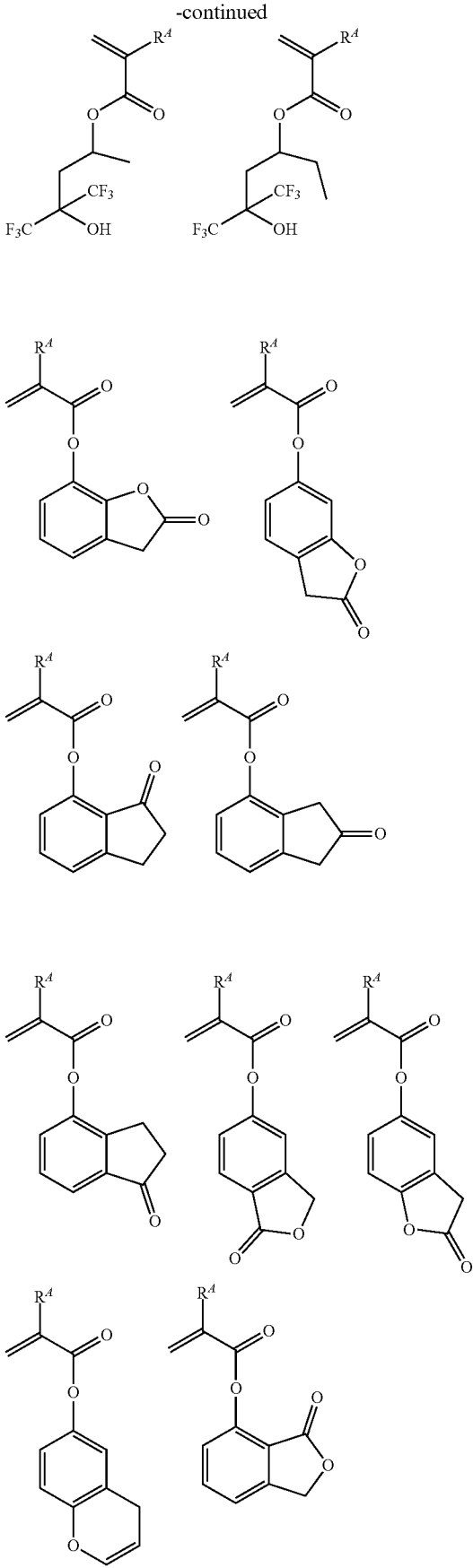

89
-continued
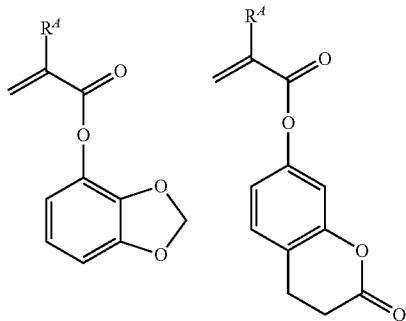
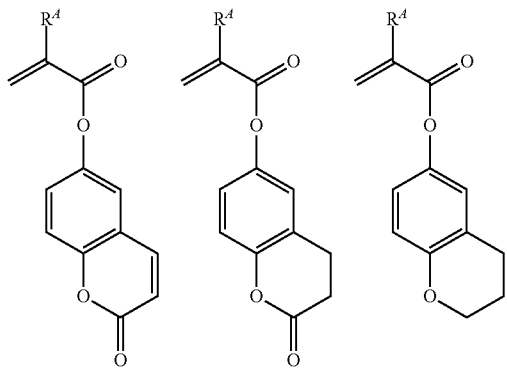
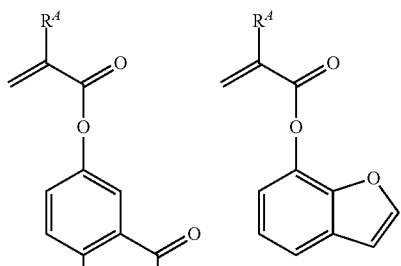
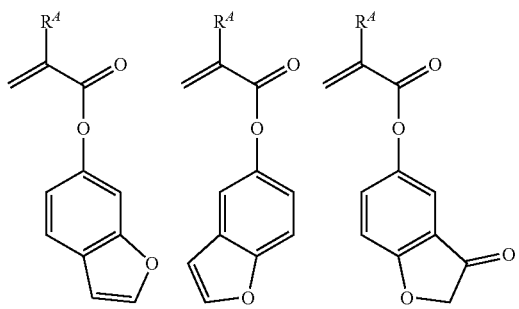
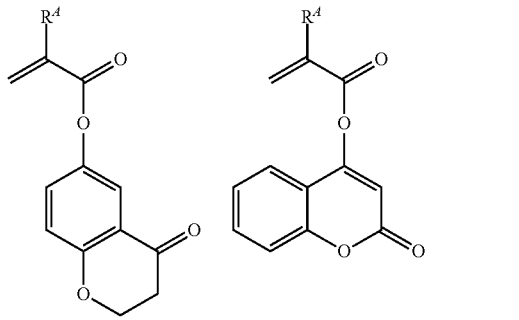
90
-continued
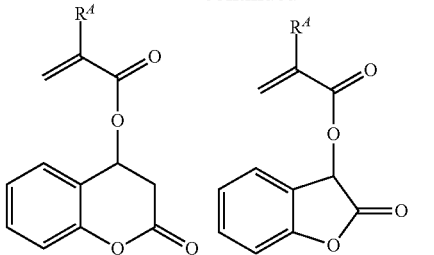
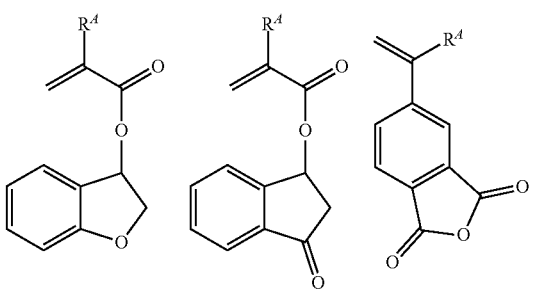
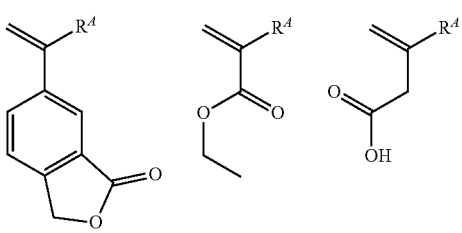
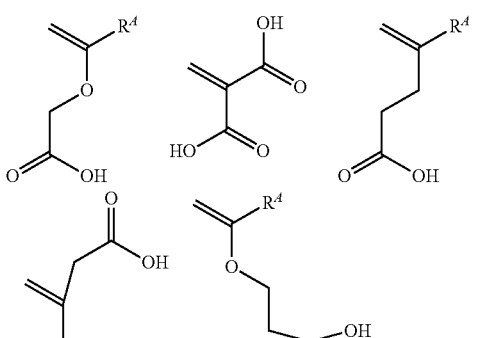
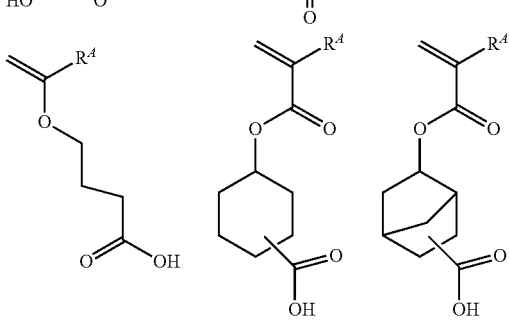

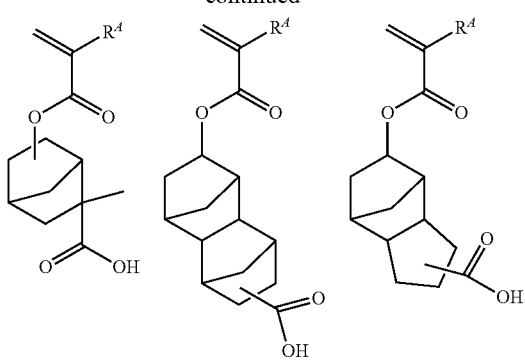
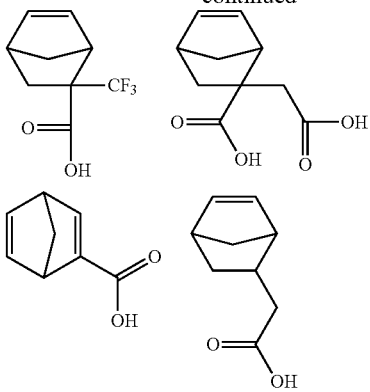
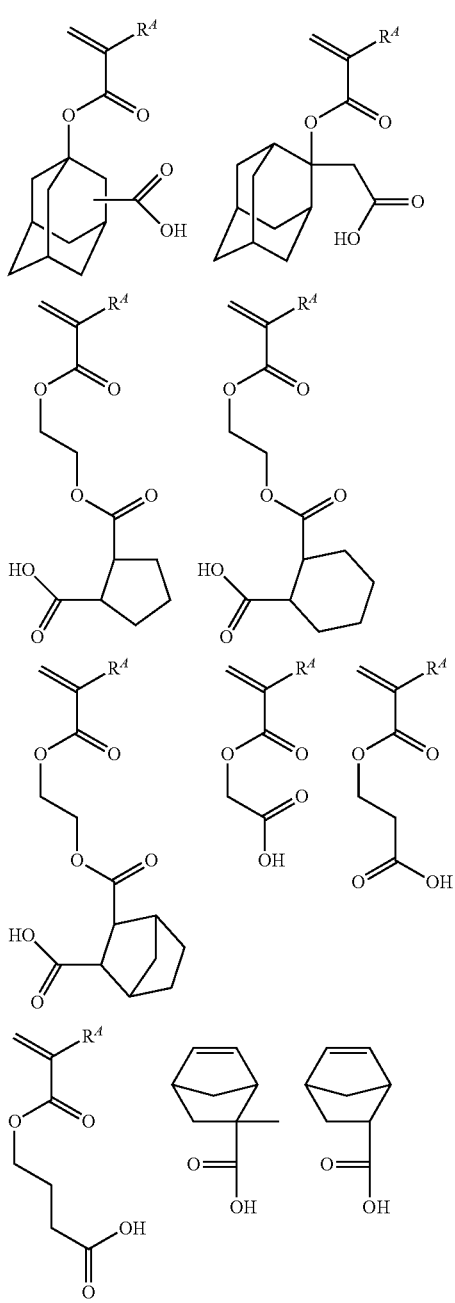

In another preferred embodiment, the base polymer may further comprise recurring units (d) derived from indene, benzofuran, benzothiophene, acenaphthylene, chromone, coumarin, and norbornadiene, or derivatives thereof. Suitable monomers are exemplified below.

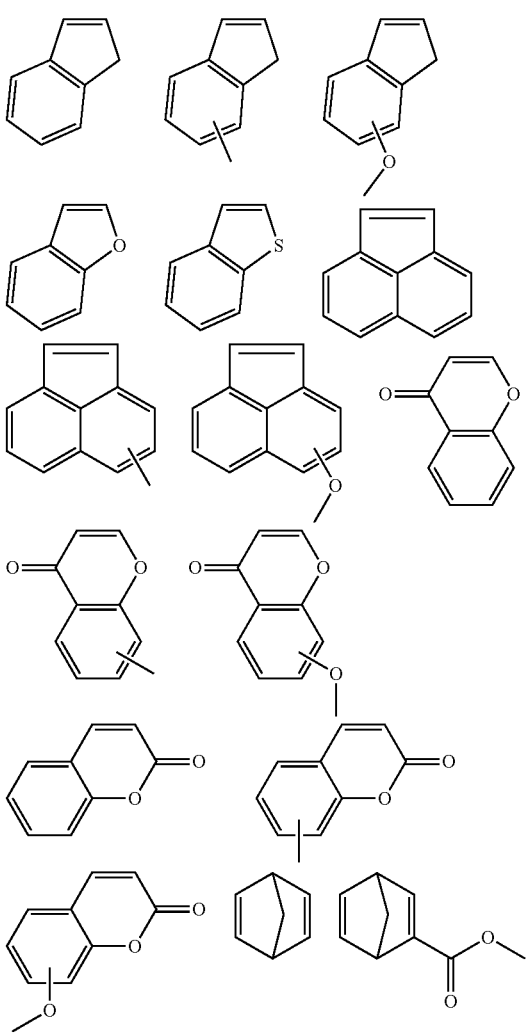

Besides the recurring units described above, further recurring units (e) may be incorporated in the base polymer, examples of which include styrene, vinylnaphthalene, vinylanthracene, vinylpyrene, methyleneindene, vinylpyridine, and vinylcarbazole.

In a further embodiment, recurring units (f) derived from an onium salt having a polymerizable unsaturated bond may be incorporated in the base polymer. The preferred recurring units (f) are recurring units having the following formulae (f1), (f2) and (f3). These units are simply referred to as recurring units (f1), (f2) and (f3), which may be used alone or in combination of two or more types.

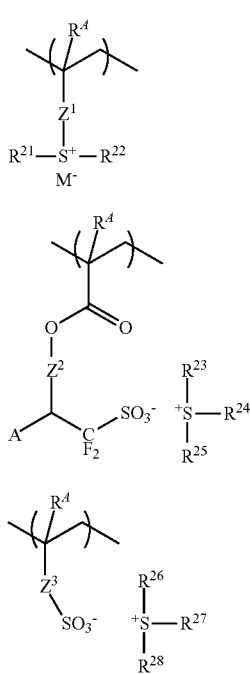

In formulae (f1) to (f3), $R^A$ is each independently hydrogen or methyl. $Z^1$ is a single bond, phenylene group, —O—$Z^{11}$—, —C(=O)—O—$Z^{11}$—, or —C(=O)—NH—$Z^{11}$—, wherein $Z^{11}$ is a $C_1$-$C_6$ alkanediyl, $C_2$-$C_6$ alkenediyl or phenylene group, which may contain a carbonyl moiety, ester bond, ether bond or hydroxyl moiety. $Z^2$ is a single bond, —$Z^{21}$—C(=O)—O—, —$Z^{21}$—O— or —$Z^{21}$—O—C(=O)—, wherein $Z^{21}$ is a $C_1$-$C_{12}$ alkanediyl group which may contain a carbonyl moiety, ester bond or ether bond. $Z^3$ is a single bond, methylene, ethylene, phenylene or fluorinated phenylene group, —O—$Z^{31}$—, —C(=O)—O—$Z^{31}$—, or —C(=O)—NH—$Z^{31}$—, wherein $Z^{31}$ is a $C_1$-$C_6$ alkanediyl, $C_2$-$C_6$ alkenediyl, phenylene, fluorinated phenylene, or trifluoromethyl-substituted phenylene group, which may contain a carbonyl moiety, ester bond, ether bond or hydroxyl moiety. Notably, the alkanediyl and alkenediyl groups may be straight, branched or cyclic.

In formulae (f1) to (f3), $R^{21}$ to $R^{28}$ are each independently a $C_1$-$C_{20}$ monovalent hydrocarbon group which may contain a heteroatom. The monovalent hydrocarbon group may be straight, branched or cyclic and examples thereof include $C_1$-$C_{12}$ alkyl, $C_6$-$C_{12}$ aryl, and $C_7$-$C_{20}$ aralkyl groups. In these groups, some or all hydrogen may be substituted by $C_1$-$C_{10}$ alkyl, halogen, trifluoromethyl, cyano, nitro, hydroxyl, mercapto, $C_1$-$C_{10}$ alkoxy, $C_2$-$C_{10}$ alkoxycarbonyl, or $C_2$-$C_{10}$ acyloxy moiety, or some carbon may be replaced by a carbonyl moiety, ether bond or ester bond. Any two of $R^{23}$, $R^{24}$ and $R^{25}$ or any two of $R^{26}$, $R^{27}$ and $R^{28}$ may bond together to form a ring with the sulfur atom to which they are attached. The thus formed ring is as exemplified above for the case where two $R^5$ bond together to form a ring with the sulfur atom in formula (1). "A" is hydrogen or trifluoromethyl.

In formula (f1), $M^-$ is a non-nucleophilic counter ion. Examples of the non-nucleophilic counter ion include halide ions such as chloride and bromide ions; fluoroalkylsulfonate ions such as triflate, 1,1,1-trifluoromethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imide ions such as bis(trifluoromethylsulfonyl)imide, bis(perfluoroethylsulfonyl)imide and bis(perfluorobutylsulfonyl)imide; methide ions such as tris(trifluoromethylsulfonyl)methide and tris(perfluoroethylsulfonyl)methide.

Also included are sulfonate ions having fluorine substituted at α-position as represented by the formula (K-1) and sulfonate ions having fluorine substituted at α- and β-positions as represented by the formula (K-2).

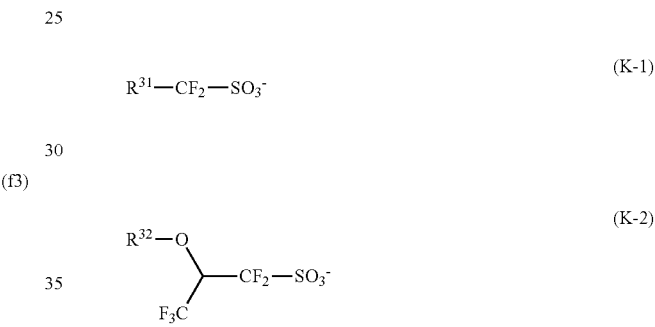

In formula (K-1), $R^{31}$ is hydrogen, or a $C_1$-$C_{20}$ alkyl group, $C_2$-$C_{20}$ alkenyl group, or $C_6$-$C_{20}$ aryl group, which may contain an ether bond, ester bond, carbonyl moiety, lactone ring, or fluorine atom. The alkyl and alkenyl groups may be straight, branched or cyclic.

In formula (K-2), $R^{32}$ is hydrogen, or a $C_1$-$C_{30}$ alkyl group, $C_2$-$C_{30}$ acyl group, $C_2$-$C_{20}$ alkenyl group, $C_6$-$C_{20}$ aryl group or $C_6$-$C_{20}$ aryloxy group, which may contain an ether bond, ester bond, carbonyl moiety or lactone ring. The alkyl, acyl and alkenyl groups may be straight, branched or cyclic.

Examples of the monomer from which recurring unit (f1) is derived are shown below, but not limited thereto. $R^A$ and $M^-$ are as defined above.

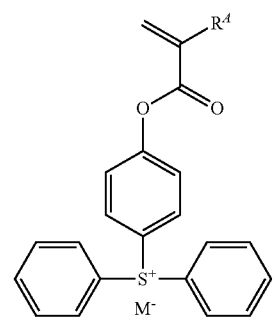

-continued
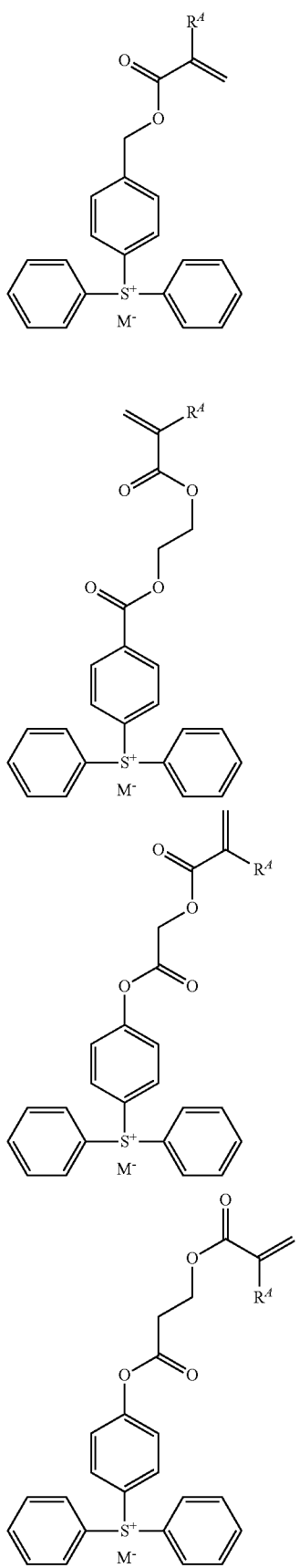
-continued
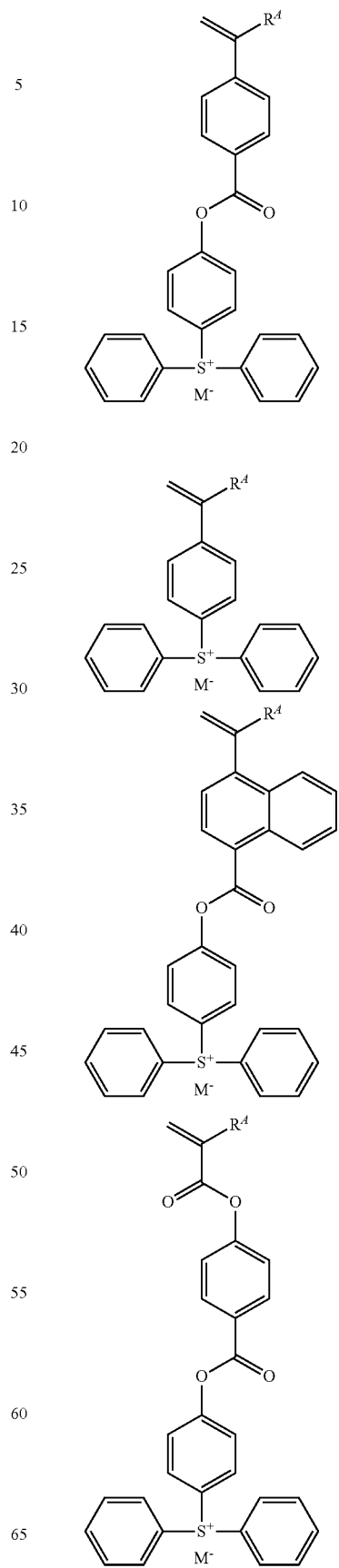

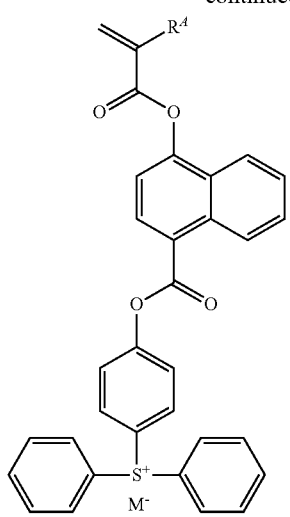
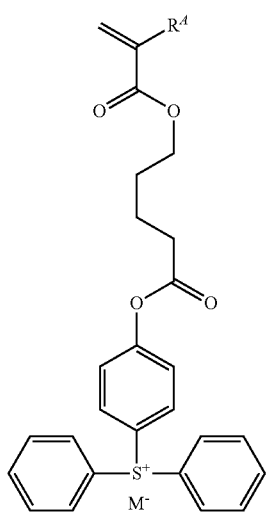
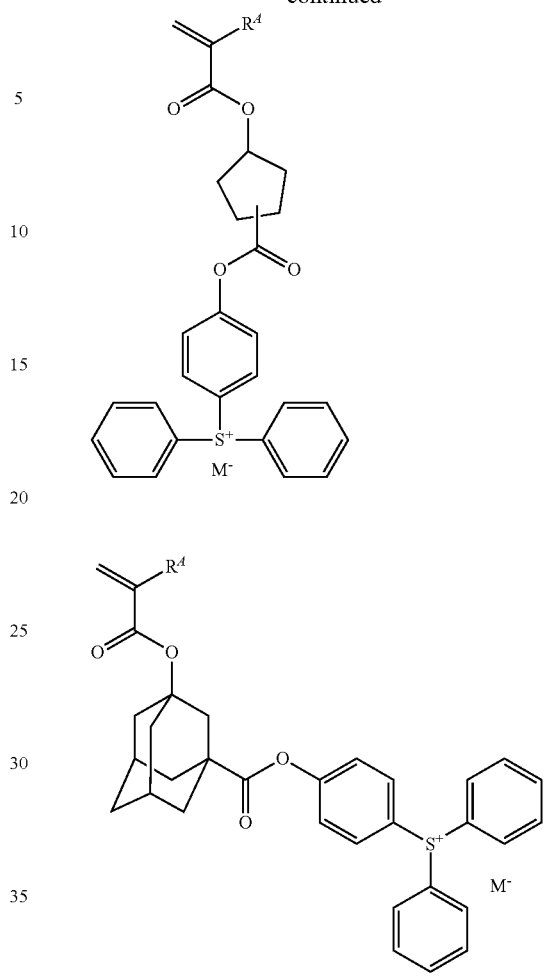
Examples of the monomer from which recurring unit (f2) is derived are shown below, but not limited thereto. $R^A$ is as defined above.
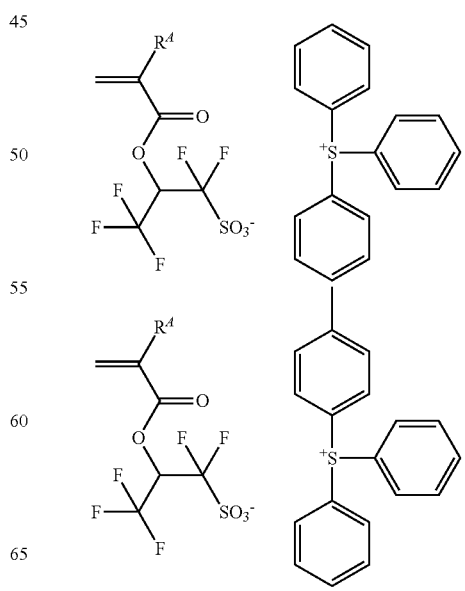

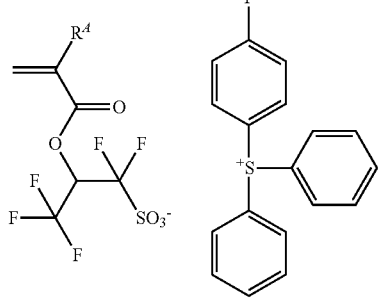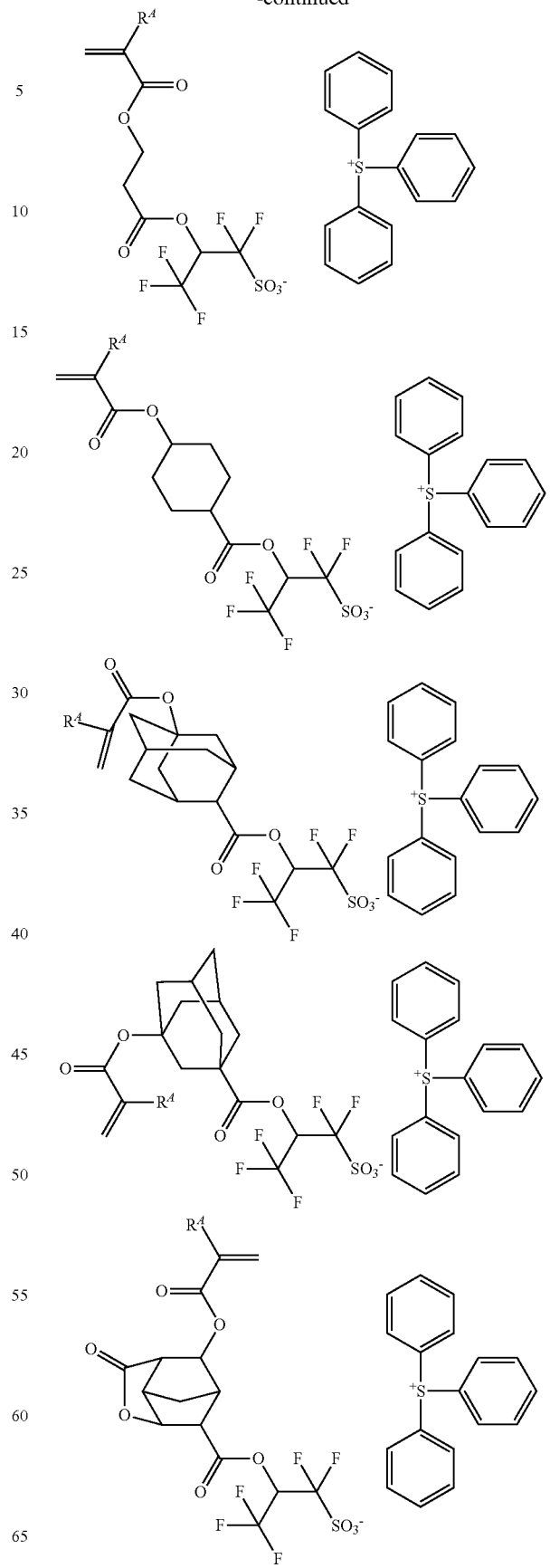

-continued
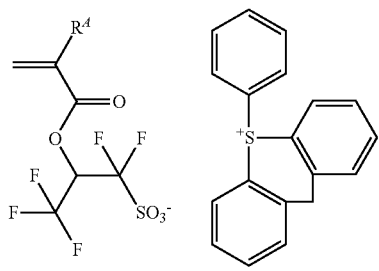
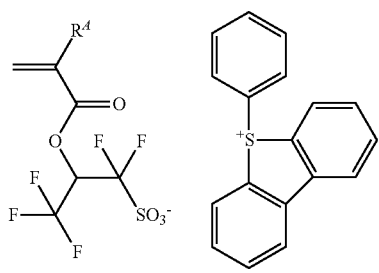
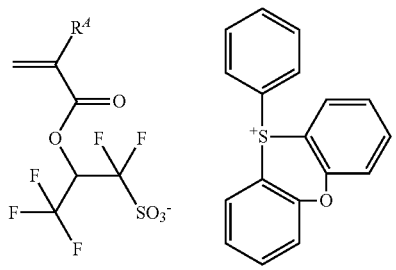
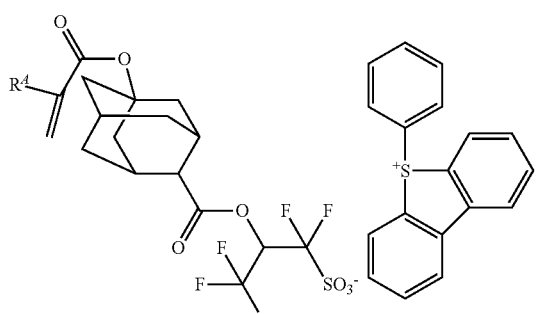
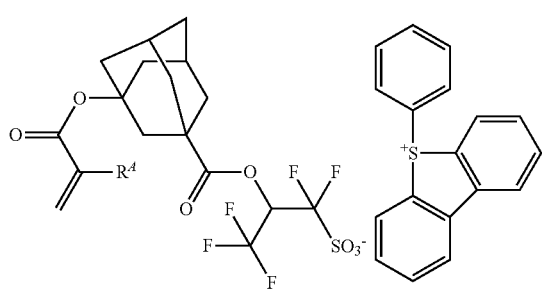
-continued
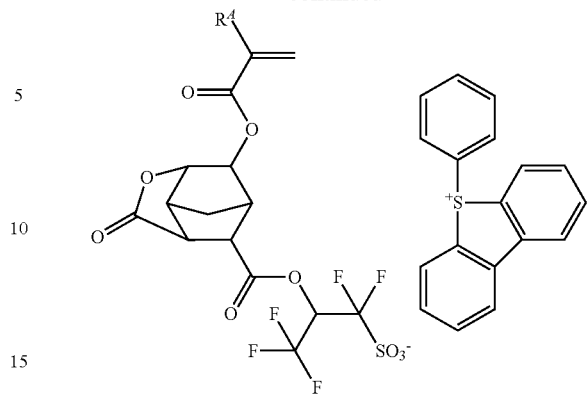
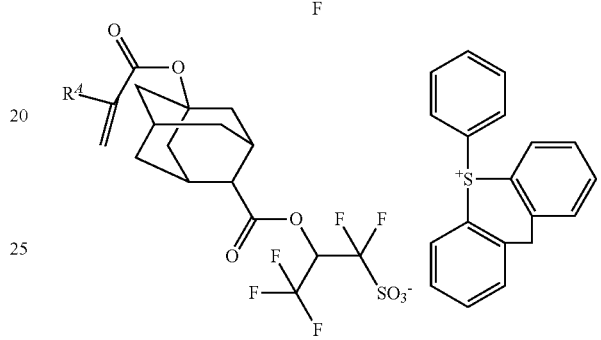
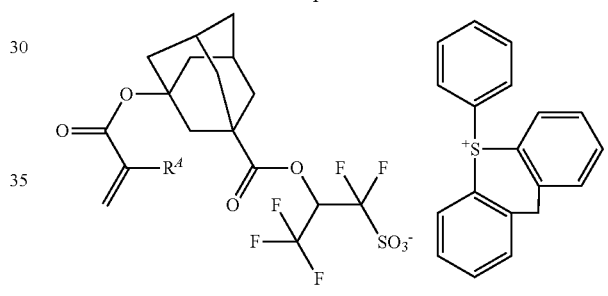
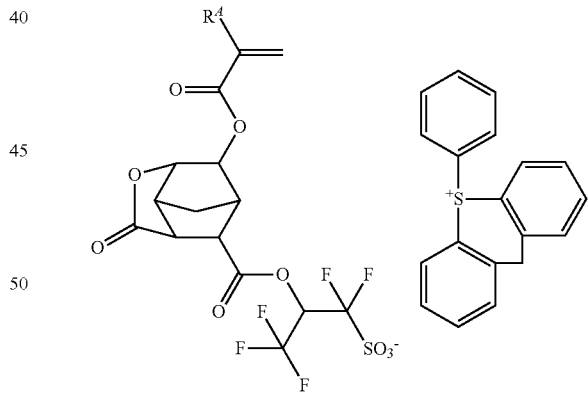
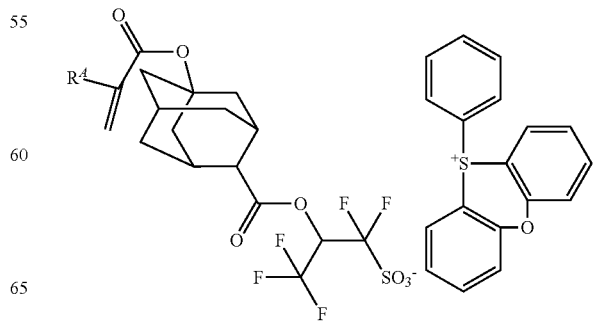

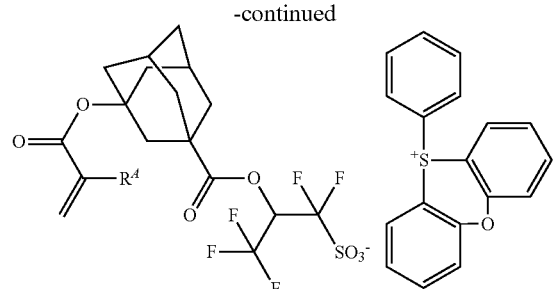
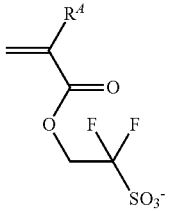
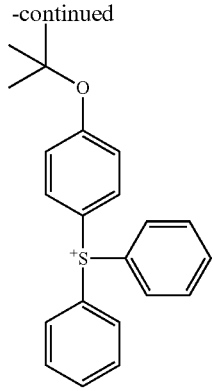
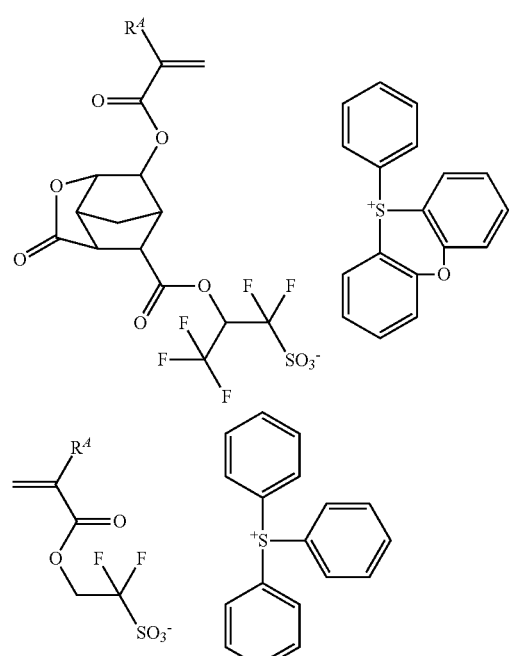
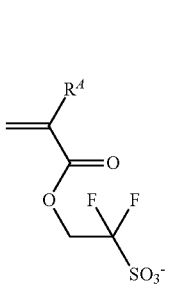
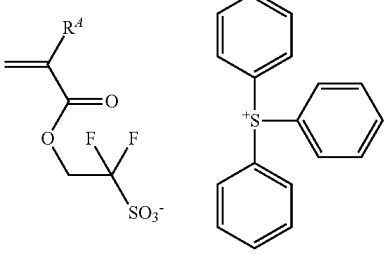
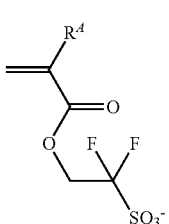
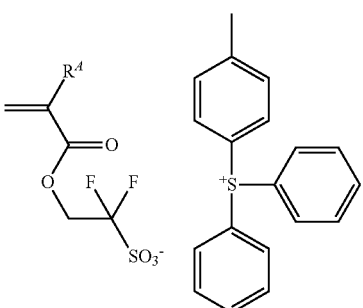
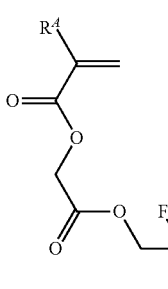
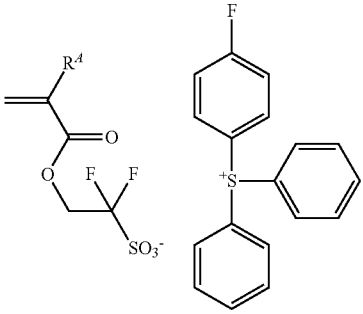
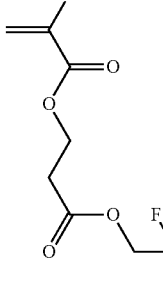

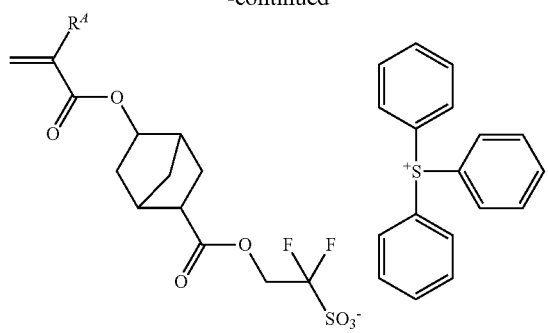
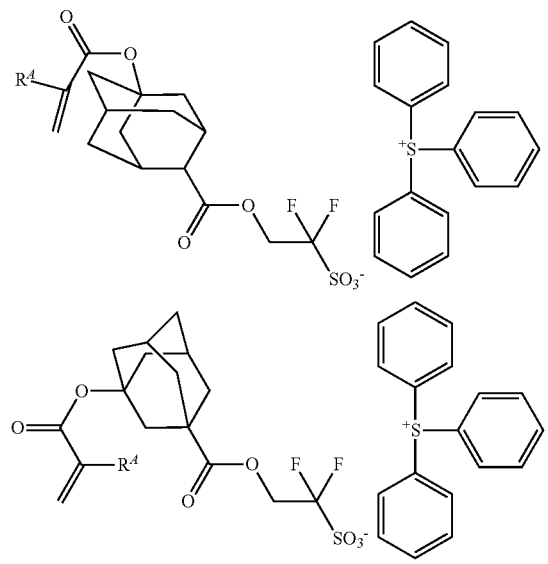
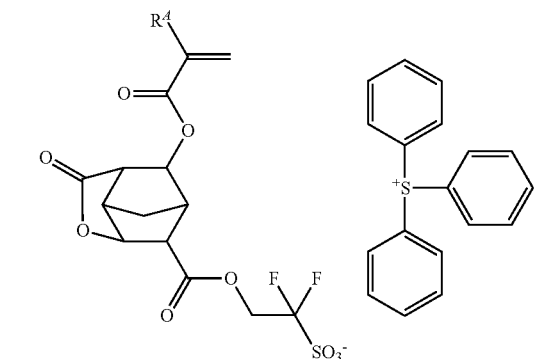
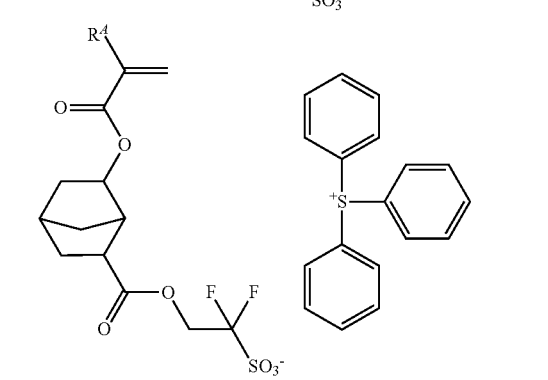
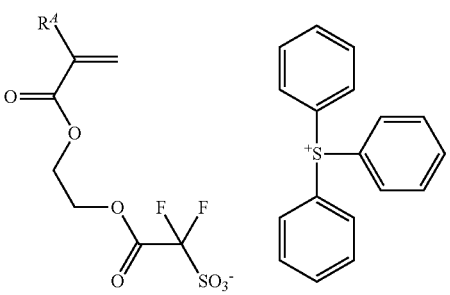
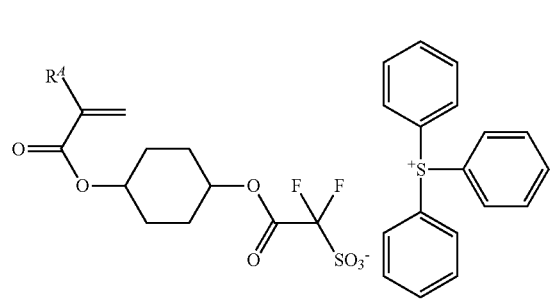
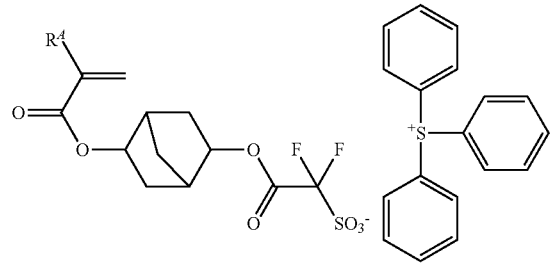
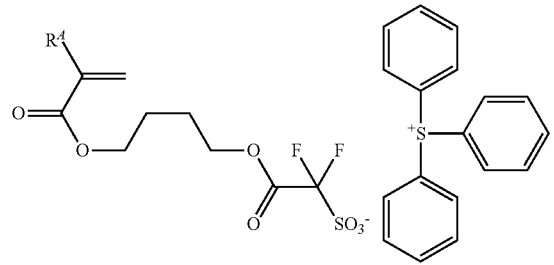
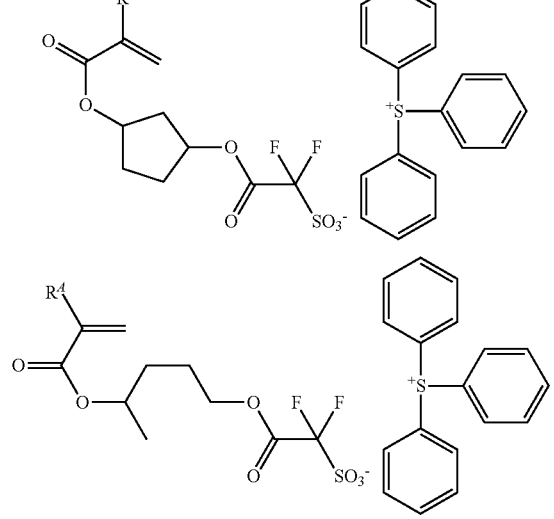
Examples of the monomer from which recurring unit (f3) is derived are shown below, but not limited thereto. $R^A$ is as defined above.

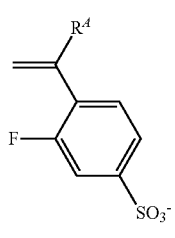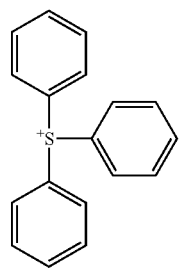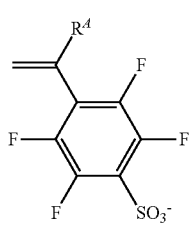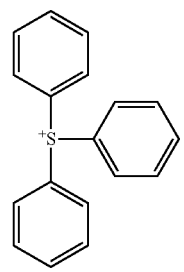
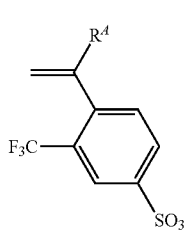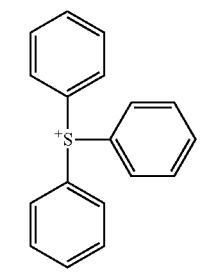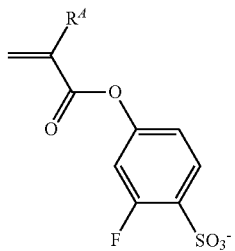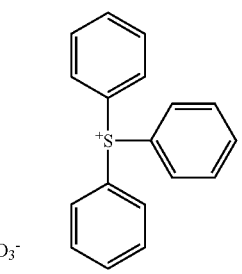
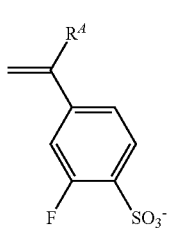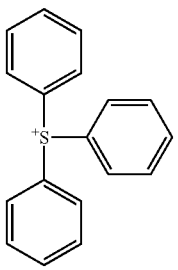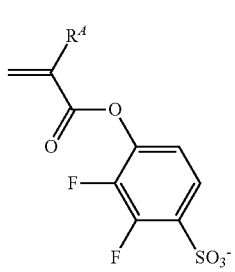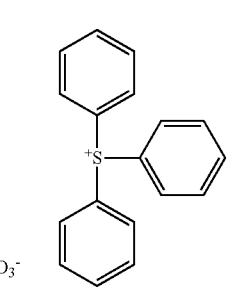
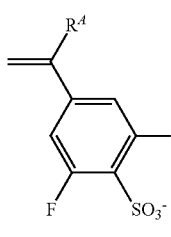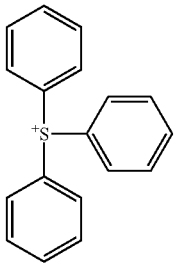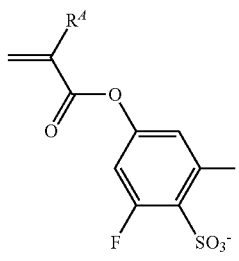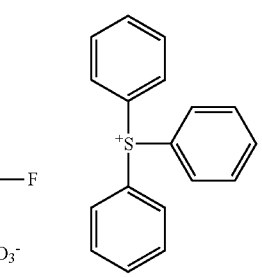
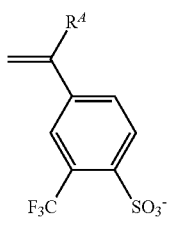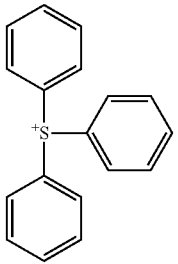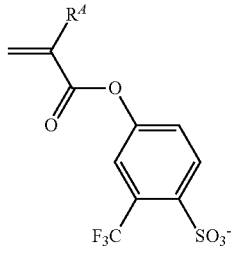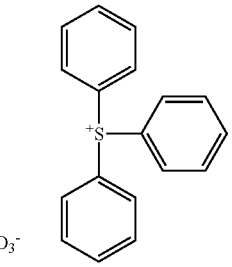
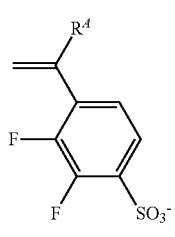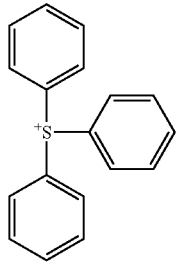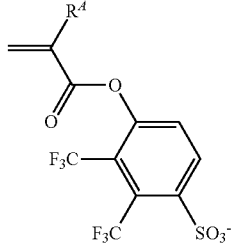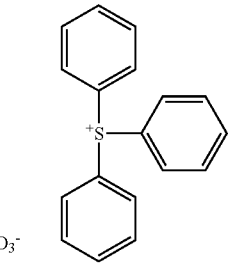

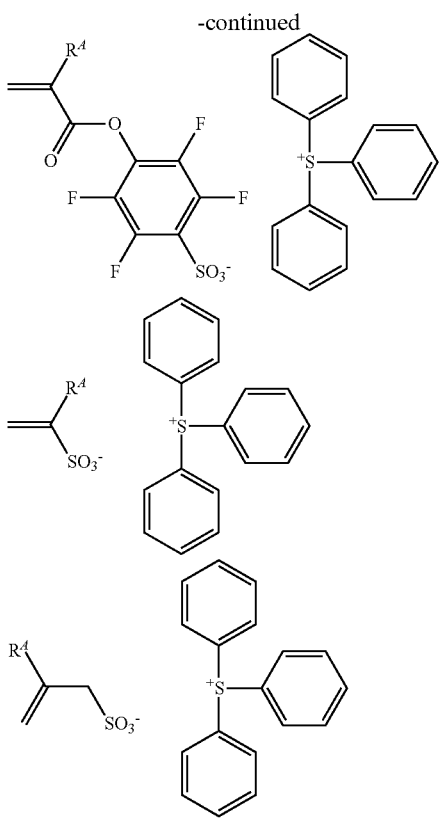

The attachment of an acid generator to the polymer main chain is effective in restraining acid diffusion, thereby preventing a reduction of resolution due to blur by acid diffusion. Also LWR is improved since the acid generator is uniformly distributed.

The base polymer for formulating the positive resist composition comprises recurring units (a1) or (a2) having an acid labile group as essential component and additional recurring units (b), (c), (d), (e), and (f) as optional components. A fraction of units (a1), (a2), (b), (c), (d), (e), and (f) is: preferably 0≤a1<1.0, 0≤a2<1.0, 0≤a1+a2<1.0, 0≤b≤0.9, 0≤c≤0.9, 0≤d≤0.8, 0≤e≤0.8, and 0≤f≤0.5; more preferably 0≤a1≤0.9, 0≤a2≤0.9, 0.1≤a1+a2≤0.9, 0≤b≤0.8, 0≤c≤0.8, 0≤d≤0.7, 0≤e≤0.7, and 0≤f≤0.4; and even more preferably 0≤a1≤0.8, 0≤a2≤0.8, 0.1≤a1+a2≤0.8, 0≤b≤0.75, 0≤c≤0.75, 0≤d≤0.6, 0≤e≤0.6, and 0≤f≤0.3. Notably, f=f1+f2+f3, meaning that unit (f) is at least one of units (f1) to (f3), and a1+a2+b+c+d+e+f=1.0.

For the base polymer for formulating the negative resist composition, an acid labile group is not necessarily essential. The base polymer comprises recurring units (b), and optionally recurring units (c), (d), (e), and/or (f). A fraction of these units is: preferably 0<b≤1.0, 0≤c≤0.9, 0≤d≤0.8, 0≤e≤0.8, and 0≤f≤0.5; more preferably 0.2≤b≤1.0, 0≤c≤0.8, 0≤d≤0.7, 0≤e≤0.7, and 0≤f≤0.4; and even more preferably 0.3≤b≤1.0, 0≤c≤0.75, 0≤d≤0.6, 0≤e≤0.6, and 0≤f≤0.3. Notably, f=f1+f2+f3, meaning that unit (f) is at least one of units (f1) to (f3), and b+c+d+e+f=1.0.

The base polymer may be synthesized by any desired methods, for example, by dissolving one or more monomers selected from the monomers corresponding to the foregoing recurring units in an organic solvent, adding a radical polymerization initiator thereto, and heating for polymerization. Examples of the organic solvent which can be used for polymerization include toluene, benzene, tetrahydrofuran, diethyl ether, and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the reaction temperature is 50 to 80° C., and the reaction time is 2 to 100 hours, more preferably 5 to 20 hours.

In the case of a monomer having a hydroxyl group, the hydroxyl group may be replaced by an acetal group susceptible to deprotection with acid, typically ethoxyethoxy, prior to polymerization, and the polymerization be followed by deprotection with weak acid and water. Alternatively, the hydroxyl group may be replaced by an acetyl, formyl, pivaloyl or similar group prior to polymerization, and the polymerization be followed by alkaline hydrolysis.

When hydroxystyrene or hydroxyvinylnaphthalene is copolymerized, an alternative method is possible. Specifically, acetoxystyrene or acetoxyvinylnaphthalene is used instead of hydroxystyrene or hydroxyvinylnaphthalene, and after polymerization, the acetoxy group is deprotected by alkaline hydrolysis, for thereby converting the polymer product to hydroxystyrene or hydroxyvinylnaphthalene. For alkaline hydrolysis, a base such as aqueous ammonia or triethylamine may be used. Preferably the reaction temperature is −20° C. to 100° C., more preferably 0° C. to 60° C., and the reaction time is 0.2 to 100 hours, more preferably 0.5 to 20 hours.

The base polymer should preferably have a weight average molecular weight (Mw) in the range of 1,000 to 500,000, and more preferably 2,000 to 30,000, as measured by GPC versus polystyrene standards using tetrahydrofuran (THF) solvent. With too low a Mw, the resist composition may become less heat resistant. A polymer with too high a Mw may lose alkaline solubility and give rise to a footing phenomenon after pattern formation.

If a base polymer has a wide molecular weight distribution or dispersity (Mw/Mn), which indicates the presence of lower and higher molecular weight polymer fractions, there is a possibility that foreign matter is left on the pattern or the pattern profile is degraded. The influences of molecular weight and dispersity become stronger as the pattern rule becomes finer. Therefore, the base polymer should preferably have a narrow dispersity (Mw/Mn) of 1.0 to 2.0, especially 1.0 to 1.5, in order to provide a resist composition suitable for micropatterning to a small feature size.

The base polymer may be a blend of two or more polymers which differ in compositional ratio, Mw or Mw/Mn.

Other Components

In the resist composition containing the sulfonium salt having formula (1) and the base polymer defined above, other components such as an organic solvent, photoacid generator other than the sulfonium salt having formula (1), quencher, surfactant, dissolution inhibitor, and crosslinker may be blended in any desired combination to formulate a chemically amplified positive or negative resist composition. This positive or negative resist composition has a very high sensitivity in that the dissolution rate in developer of the base polymer in exposed areas is accelerated by catalytic reaction. In addition, the resist film has a high dissolution contrast, resolution, exposure latitude, and process adaptability, and provides a good pattern profile after exposure, and minimal proximity bias because of restrained acid diffusion. By virtue of these advantages, the composition is fully useful in commercial application and suited as a pattern-forming material for the fabrication of VLSIs. Particularly when a chemically amplified resist composition capable of utilizing acid catalyzed reaction is formulated, the composition has a higher sensitivity and is further improved in the properties described above.

Examples of the organic solvent used herein are described in JP-A 2008-111103, paragraphs [0144]-[0145] (U.S. Pat. No. 7,537,880). Exemplary solvents include ketones such as cyclohexanone, cyclopentanone and methyl-2-n-pentyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether, esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, t-butyl acetate, t-butyl propionate, and propylene glycol mono-t-butyl ether acetate; and lactones such as γ-butyrolactone, which may be used alone or in admixture.

The organic solvent is preferably added in an amount of 100 to 10,000 parts, and more preferably 200 to 8,000 parts by weight per 100 parts by weight of the base polymer.

To the resist composition, an acid generator other than the sulfonium salt having formula (1) may be added insofar as the benefits of the invention are not impaired. The other acid generator is typically a compound (PAG) capable of generating an acid upon exposure to actinic ray or radiation. Although the PAG used herein may be any compound capable of generating an acid upon exposure to high-energy radiation, those compounds capable of generating sulfonic acid, imide acid (imidic acid) or methide acid are preferred. Suitable PAGs include sulfonium salts, iodonium salts, sulfonyldiazomethane, N-sulfonyloxyimide, and oxime-O-sulfonate acid generators. Exemplary PAGs are described in JP-A 2008-111103, paragraphs [0122]-[0142] (U.S. Pat. No. 7,537,880). The other acid generator is preferably used in an amount of 0 to 200 parts, more preferably 0.1 to 100 parts by weight per 100 parts by weight of the base polymer.

In the resist composition, a quencher may be blended. The quencher is typically selected from conventional basic compounds. Conventional basic compounds include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, and carbamate derivatives. Also included are primary, secondary, and tertiary amine compounds, specifically amine compounds having a hydroxyl, ether, ester, lactone ring, cyano, or sulfonic acid ester group as described in JP-A 2008-111103, paragraphs [0146]-[0164], and compounds having a carbamate group as described in JP 3790649. Addition of a basic compound may be effective for further suppressing the diffusion rate of acid in the resist film or connecting the pattern profile.

Onium salts such as sulfonium salts, iodonium salts and ammonium salts of sulfonic acids which are not fluorinated at α-position as described in U.S. Pat. No. 8,795,942 (JP-A 2008-158339) and similar onium salts of carboxylic acid may also be used as the quencher. While an α-fluorinated sulfonic acid, imide acid, and methide acid are necessary to deprotect the acid labile group of carboxylic acid ester, an α-non-fluorinated sulfonic acid or carboxylic acid is released by salt exchange with an α-non-fluorinated onium salt. An α-non-fluorinated sulfonic acid and a carboxylic acid function as a quencher because they do not induce deprotection reaction.

Examples of the quencher include a compound (onium salt of α-non-fluorinated sulfonic acid) having the formula (2) and a compound (onium salt of carboxylic acid) having the formula (3).

In formula (2), $R^{101}$ is hydrogen or a $C_1$-$C_{40}$ monovalent hydrocarbon group which may contain a heteroatom, exclusive of the hydrocarbon group in which the hydrogen bonded to the carbon atom at α-position of the sulfone group is substituted by fluorine or fluoroalkyl group. Examples of the monovalent hydrocarbon group include alkyl, alkenyl, aryl, aralkyl and aryloxoalkyl groups. Suitable alkyl groups include methyl, ethyl, propyl, isopropyl, n-butyl, sec-butyl, tert-butyl, tert-pentyl, n-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, adamantyl, and adamantylmethyl. Suitable alkenyl groups include vinyl, allyl, propenyl, butenyl, hexenyl, and cyclohexenyl. Suitable aryl groups include phenyl, naphthyl, thienyl, 4-hydroxyphenyl, alkoxyphenyl groups such as 4-methoxyphenyl, 3-methoxyphenyl, 2-methoxyphenyl, 4-ethoxyphenyl, 4-tert-butoxyphenyl, and 3-tert-butoxyphenyl; alkylphenyl groups such as 2-methylphenyl, 3-methylphenyl, 4-methylphenyl, 4-ethylphenyl, 4-tert-butylphenyl, 4-n-butylphenyl, 2,4-dimethylphenyl, and 2,4,6-triisopropylphenyl; alkylnaphthyl groups such as methylnaphthyl and ethylnaphthyl; alkoxynaphthyl groups such as methoxynaphthyl, ethoxynaphthyl, n-propoxynaphthyl and n-butoxynaphthyl; dialkylnaphthyl groups such as dimethylnaphthyl and diethylnaphthyl; and dialkoxynaphthyl groups such as dimethoxynaphthyl and diethoxynaphthyl. Suitable aralkyl groups include benzyl, 1-phenylethyl and 2-phenylethyl. Suitable aryloxoalkyl groups include 2-aryl-2-oxoethyl groups such as 2-phenyl-2-oxoethyl, 2-(1-naphthyl)-2-oxoethyl, and 2-(2-naphthyl)-2-oxoethyl. In these groups, some hydrogen may be substituted by a moiety containing a heteroatom such as oxygen, sulfur, nitrogen or halogen, and some carbon may be replaced by a moiety containing a heteroatom such as oxygen, sulfur or nitrogen, so that the group may contain a hydroxyl moiety, cyano moiety, carbonyl moiety, ether bond, ester bond, sulfonic acid ester bond, carbonate bond, lactone ring, sultone ring, carboxylic anhydride, or haloalkyl moiety.

In formula (3), $R^{102}$ is a $C_1$-$C_{40}$ monovalent hydrocarbon group which may contain a heteroatom. Examples of the monovalent hydrocarbon group $R^{102}$ are as exemplified above for the monovalent hydrocarbon group $R^{101}$. Also included are fluorinated alkyl groups such as trifluoromethyl, trifluoroethyl, 2,2,2-trifluoro-1-methyl-1-hydroxyethyl, 2,2,2-trifluoro-1-(trifluoromethyl)-1-hydroxyethyl, aryl groups such as phenyl, tolyl, xylyl, 4-tert-butylphenyl, and naphthyl, and fluorinated aryl groups such as pentafluorophenyl and 4-trifluoromethylphenyl.

A sulfonium salt of iodized benzene ring-containing carboxylic acid having the formula (4) is also useful as the quencher.

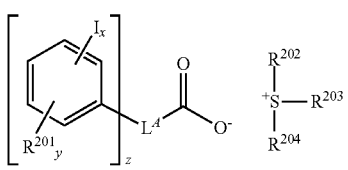

(4)

In formula (4), $R^{201}$ is hydroxyl, or a $C_1$-$C_6$ alkyl, $C_1$-$C_6$ alkoxy, $C_2$-$C_6$ acyloxy or $C_1$-$C_4$ alkylsulfonyloxy group, in which some or all hydrogen may be substituted by halogen, or fluorine, chlorine, bromine, amino, nitro, cyano, —$NR^{201A}$—C(O)—$R^{201B}$, or —$NR^{201A}$—C(=O)—O—$R^{201B}$, wherein $R^{201A}$ is hydrogen or a $C_1$-$C_6$ alkyl group and $R^{201B}$ is a $C_1$-$C_6$ alkyl or $C_2$-$C_8$ alkenyl group.

In formula (4), $L^A$ is a single bond, or a $C_1$-$C_{20}$ (z+1)-valent linking group which may contain an ether bond, carbonyl, ester bond, amide bond, sultone ring, lactam ring, carbonate, halogen, hydroxyl or carboxyl moiety.

In formula (4), $R^{202}$, $R^{203}$ and $R^{204}$ are each independently fluorine, chlorine, bromine, iodine, or a $C_1$-$C_{12}$ alkyl, $C_2$-$C_{12}$ alkenyl, $C_6$-$C_{20}$ aryl, $C_7C_{12}$ aralkyl or $C_7$-$C_{12}$ aryloxyalkyl group, in which some or all hydrogen may be substituted by hydroxyl, carboxyl, halogen, oxo, cyano, amide, nitro, sultone ring-containing moiety, sulfone, or sulfonium salt-containing moiety or in which an ether bond, ester bond, carbonyl, carbonate or sulfonic acid ester may intervene in a carbon-carbon bond. Any two of $R^{202}$, $R^{203}$ and $R^{204}$ may bond together to form a ring with the sulfur atom to which they are attached. The thus formed ring is as exemplified above for the case where two $R^5$ bond together to form a ring with the sulfur atom in formula (1).

In formula (4), x is an integer of 1 to 5, y is an integer of 0 to 3, and z is an integer of 1 to 3.

Examples of the compound having formula (4) include those described in JP-A 2017-219836. Since iodine is highly absorptive to EUV of wavelength 13.5 mm, it generates secondary electrons during exposure, with the energy of secondary electrons being transferred to the acid generator. This promotes the decomposition of the quencher, contributing to a higher sensitivity.

Also useful are quenchers of polymer type as described in U.S. Pat. No. 7,598,016 (JP-A 2008-239918). The polymeric quencher segregates at the resist surface after coating and thus enhances the rectangularity of resist pattern. When a protective film is applied as is often the case in the immersion lithography, the polymeric quencher is also effective for preventing a film thickness loss of resist pattern or rounding of pattern top.

The quencher is preferably added in an amount of 0 to 5 parts, more preferably 0 to 4 parts by weight per 100 parts by weight of the base polymer.

Exemplary surfactants are described in JP-A 2008-111103, paragraphs [0165]-[0166]. Inclusion of a surfactant may improve or control the coating characteristics of the resist composition. The surfactant is preferably added in an amount of 0.0001 to 10 parts by weight per 100 parts by weight of the base polymer.

In the case of positive resist compositions, inclusion of a dissolution inhibitor may lead to an increased difference in dissolution rate between exposed and unexposed areas and a further improvement in resolution. In the case of negative resist compositions, a negative pattern may be formed by adding a crosslinker to reduce the dissolution rate of exposed area.

The dissolution inhibitor which can be used herein is a compound having at least two phenolic hydroxyl groups on the molecule, in which an average of from 0 to 100 mol % of all the hydrogen atoms on the phenolic hydroxyl groups are replaced by acid labile groups or a compound having at least one carboxyl group on the molecule, in which an average of 50 to 100 mol % of all the hydrogen atoms on the carboxyl groups are replaced by acid labile groups, both the compounds having a molecular weight of 100 to 1,000, and preferably 150 to 800. Typical are bisphenol A, trisphenol, phenolphthalein, cresol novolac, naphthalenecarboxylic acid, adamantanecarboxylic acid, and cholic acid derivatives in which the hydrogen atom on the hydroxyl or carboxyl group is replaced by an acid labile group, as described in U.S. Pat. No. 7,771,914 (JP-A 2008-122932, paragraphs [0155]-[0178]).

In the positive resist composition, the dissolution inhibitor is preferably added in an amount of 0 to 50 parts, more preferably 5 to 40 parts by weight per 100 parts by weight of the base polymer.

Suitable crosslinkers which can be used herein include epoxy compounds, melamine compounds, guanamine compounds, glycoluril compounds and urea compounds having substituted thereon at least one group selected from among methylol, alkoxymethyl and acyloxymethyl groups, isocyanate compounds, azide compounds, and compounds having a double bond such as an alkenyl ether group. These compounds may be used as an additive or introduced into a polymer side chain as a pendant. Hydroxy-containing to compounds may also be used as the crosslinker.

Suitable epoxy compounds include tris(2,3-epoxypropyl) isocyanurate, trimethylolmethane triglycidyl ether, trimethylolpropane triglycidyl ether, and triethylolethane triglycidyl ether. Examples of the melamine compound include hexamethylol melamine, hexamethoxymethyl melamine, hexamethylol melamine compounds having 1 to 6 methylol groups methoxymethylated and mixtures thereof, hexamethoxyethyl melamine, hexaacyloxymethyl melamine, hexamethylol melamine compounds having 1 to 6 methylol groups acyloxymethylated and mixtures thereof. Examples of the guanamine compound include tetramethylol guanamine, tetramethoxymethyl guanamine, tetramethylol guanamine compounds having 1 to 4 methylol groups methoxymethylated and mixtures thereof, tetramethoxyethyl guanamine, tetraacyloxyguananine, tetramethylol guanamine compounds having 1 to 4 methylol groups acyloxymethylated and mixtures thereof. Examples of the glycoluril compound include tetramethylol glycoluril, tetramethoxyglycoluril, tetramethoxymethyl glycoluril, tetramethylol glycoluril compounds having 1 to 4 methylol groups methoxymethylated and mixtures thereof, tetramethylol glycoluril compounds having 1 to 4 methylol groups acyloxymethylated and mixtures thereof. Examples of the urea compound include tetramethylol urea, tetramethoxymethyl urea, tetramethylol urea compounds having 1 to 4 methylol groups methoxymethylated and mixtures thereof, and tetramethoxyethyl urea.

Suitable isocyanate compounds include tolylene diisocyanate, diphenylmethane diisocyanate, hexamethylene diisocyanate and cyclohexane diisocyanate. Suitable azide compounds include 1,1'-biphenyl-4,4'-bisazide, 4,4'-methylidenebisazide, and 4,4'-oxybisazide. Examples of the alkenyl ether group-containing compound include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylol propane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylol propane trivinyl ether.

In the negative resist composition, the crosslinker is preferably added in an amount of 0.1 to 50 parts, more preferably 1 to 40 parts by weight per 100 parts by weight of the base polymer.

To the resist composition, a polymeric additive (or water repellency improver) may also be added for improving the water repellency on surface of a resist film as spin coated. The water repellency improver may be used in the topcoatless immersion lithography. Suitable water repellency improvers include polymers having a fluoroalkyl group and polymers having a specific structure with a 1,1,1,3,3,3-hexafluoro-2-propanol residue and are described in JP-A 2007-297590 and JP-A 2008-111103, for example. The water repellency improver to be added to the resist composition should be soluble in the organic solvent as the developer. The water repellency improver of specific structure with a 1,1,1,3,3,3-hexafluoro-2-propanol residue is well soluble in the developer. A polymer having an amino group or amine salt copolymerized as recurring units may serve as the water repellent additive and is effective for preventing evaporation of acid during PEB, thus preventing any hole pattern opening failure after development. An appropriate amount of the water repellency improver is 0 to 20 parts, preferably 0.5 to 10 parts by weight per 100 parts by weight of the base polymer.

Also, an acetylene alcohol may be blended in the resist composition. Suitable acetylene alcohols are described in JP-A 2008-122932, paragraphs [0179]-[0182]. An appropriate amount of the acetylene alcohol blended is 0 to 5 parts by weight per 100 parts by weight of the base polymer.

Each of the foregoing additives may be used alone or in admixture of two or more.

Process

The resist composition is used in the fabrication of various integrated circuits. Pattern formation using the resist composition may be performed by well-known lithography processes. The process generally involves coating, prebaking, exposure, and development. If necessary, any additional steps may be added.

For example, the positive resist composition is first applied onto a substrate on which an integrated circuit is to be formed (e.g., Si, $SiO_2$, SiN, SiON, TiN, WSi, BPSG, SOG, or organic antireflective coating) or a substrate on which a mask circuit is to be formed (e.g., Cr, CrO, CrON, $MoSi_2$, or $SiO_2$) by a suitable coating technique such as spin coating, roll coating, flow coating, dipping, spraying or doctor coating. The coating is prebaked on a hotplate at a temperature of 60 to 150° C. for 10 seconds to 30 minutes, preferably at 80 to 120° C. for 30 seconds to 20 minutes. The resulting resist film is generally 0.01 to 2.0 μm thick.

Then the resist film is exposed patternwise to high-energy radiation. Examples of the high-energy radiation include UV, deep-UV, EB, EUV of wavelength 3 to 15 nm, x-ray, soft x-ray, excimer laser light, γ-ray or synchrotron radiation. On use of UV, deep UV, EUV, x-ray, soft x-ray, excimer laser, γ-ray or synchrotron radiation, the resist film is exposed through a mask having a desired pattern, preferably in a dose of about 1 to 200 $mJ/cm^2$, more preferably about 10 to 100 $mJ/cm^2$. On use of EB, a pattern may be written directly or through a mask having the desired pattern, preferably in a dose of about 0.1 to 100 $\mu C/cm^2$, more preferably about 0.5 to 50 $\mu C/cm^2$. The resist composition is suited for micropatterning using high-energy radiation such as KrF excimer laser, ArF excimer laser, EB, EUV, x-ray, soft x-ray, γ-ray or synchrotron radiation, especially EB or EUV.

After the exposure, the resist film may be baked (PEB) on a hotplate at 60 to 150° C. for 10 seconds to 30 minutes, preferably at 80 to 120° C. for 30 seconds to 20 minutes.

After the exposure or PEB, the resist film is developed with a developer in the form of an aqueous base solution for 3 seconds to 3 minutes, preferably 5 seconds to 2 minutes by conventional techniques such as dip, puddle and spray techniques. A typical developer is a 0.1 to 10 wt %, preferably 2 to 5 wt % aqueous solution of tetramethylammonium hydroxide (TMAH), tetraethylammonium hydroxide (TEAH), tetrapropylammonium hydroxide (TPAH), or tetrabutylammonium hydroxide (TBAH). The resist film in the exposed area is dissolved in the developer whereas the resist film in the unexposed area is not dissolved. In this way, the desired positive pattern is formed on the substrate. Inversely in the case of negative resist, the exposed area of resist film is insolubilized and the unexposed area is dissolved in the developer.

In an alternative embodiment, a negative pattern may be formed via organic solvent development using a positive resist composition comprising a base polymer having an acid labile group. The developer used herein is preferably selected from among 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate, and mixtures thereof.

At the end of development, the resist film is rinsed. As the rinsing liquid, a solvent which is miscible with the developer and does not dissolve the resist film is preferred. Suitable solvents include alcohols of 3 to 10 carbon atoms, ether compounds of 8 to 12 carbon atoms, alkanes, alkenes, and alkynes of 6 to 12 carbon atoms, and aromatic solvents. Specifically, suitable alcohols of 3 to 10 carbon atoms include n-propyl alcohol, isopropyl alcohol 1-butyl alcohol, 2-butyl alcohol, isobutyl alcohol, t-butyl alcohol, 1-pentanol, 2-pentanol, 3-pentanol, t-pentyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether compounds of 8 to 12 carbon atoms include di-n-butyl ether, diisobutyl ether, di-s-butyl ether, di-n-pentyl ether, diisopentyl ether, di-s-pentyl ether, di-t-pentyl ether, and di-n-hexyl ether. Suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexene, methylcyclohexene, dimethylcyclohexene, cycloheptene, and cyclooctene. Suitable alkynes of 6 to 12 carbon atoms include hexyne, heptyne, and octyne. Suitable aromatic solvents include toluene, xylene, ethylbenzene, isopropylbenzene, t-butylbenzene and mesitylene. The solvents may be used alone or in admixture.

Rinsing is effective for minimizing the risks of resist pattern collapse and defect formation. However, rinsing is not essential. If rinsing is omitted, the amount of solvent used may be reduced.

A hole or trench pattern after development may be shrunk by the thermal flow, RELACS® or DSA process. A hole pattern is shrunk by coating a shrink agent thereto, and baking such that the shrink agent may undergo crosslinking at the resist surface as a result of the acid catalyst diffusing from the resist layer during bake, and the shrink agent may attach to the sidewall of the hole pattern. The bake is preferably at a temperature of 70 to 180° C., more preferably 80 to 170° C., for a time of 10 to 300 seconds. The extra shrink agent is stripped and the hole pattern is shrunk.

EXAMPLES

Examples of the invention are given below by way of illustration and not by way of limitation. The abbreviation "pbw" is parts by weight.

Acid generators PAG1 to PAG20 used in resist compositions have the structure shown below. PAG1 was synthesized by etherifying reaction of a p-fluorophenyldiphenylsulfoninm salt with 1-hydroxyethoxy-2,4,6-triiodobenzene. PAG2, 3, 6, 7, 8, 9, 11 and 15 to 20 were synthesized by similar etherifying reaction whereas PAG4, 5, 10 and 12 to 14 were synthesized by esterifying reaction.

PAG 1

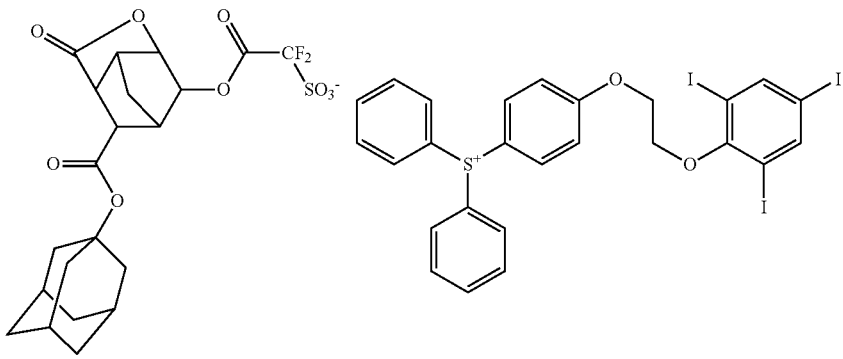

PAG 2

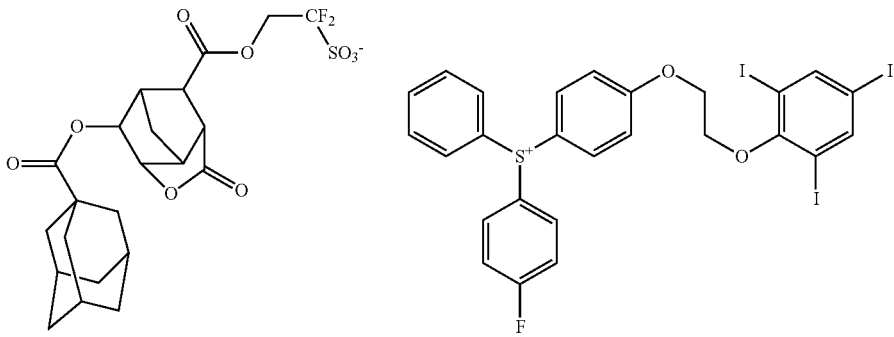

PAG 3

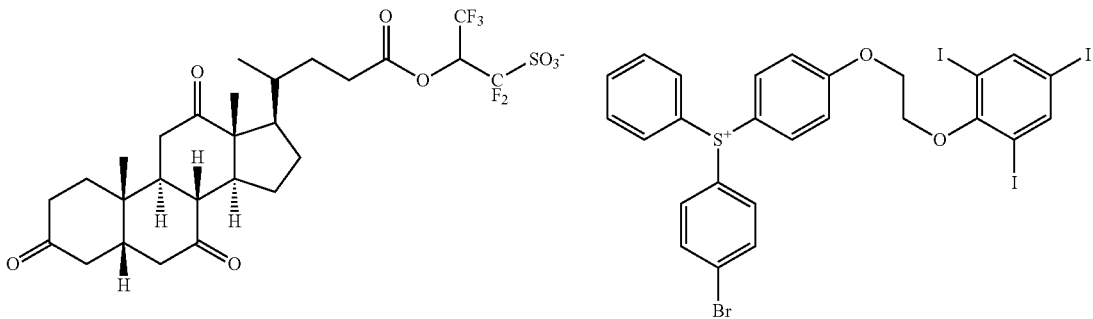

-continued
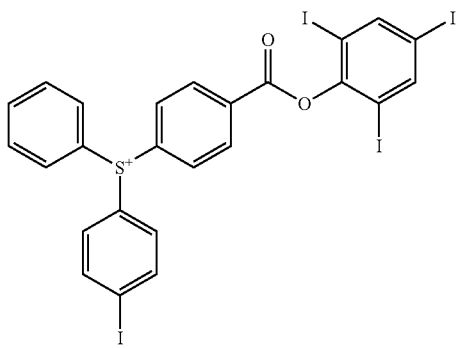
PAG 4
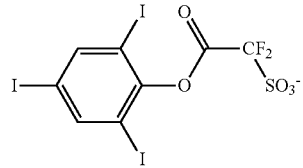
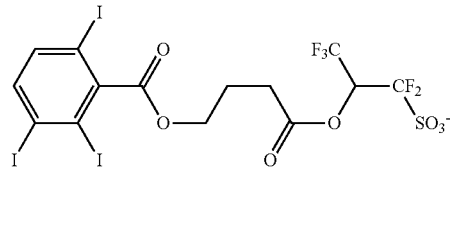
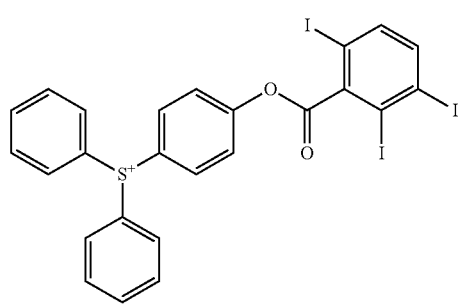
PAG 5
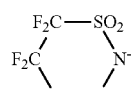
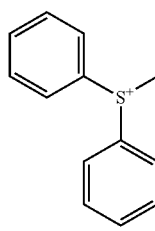
PAG 6
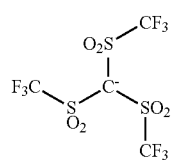
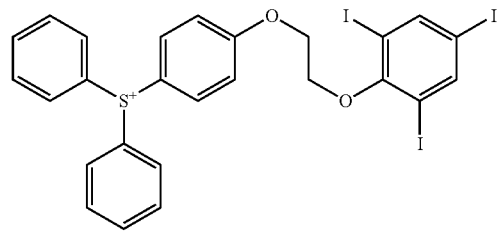
PAG 7
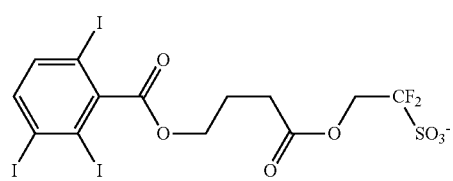
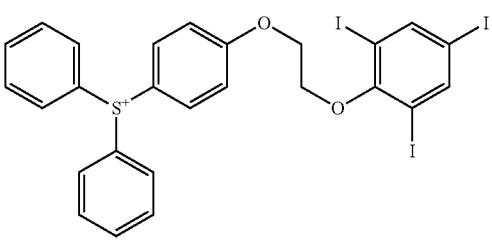
PAG 8
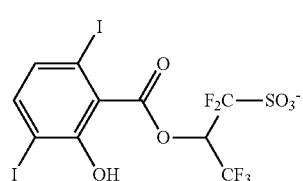
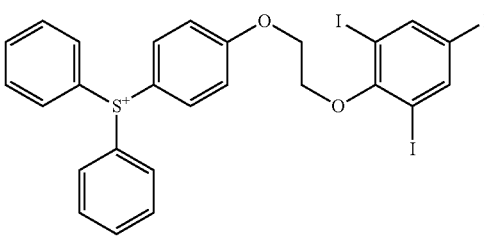
PAG 9

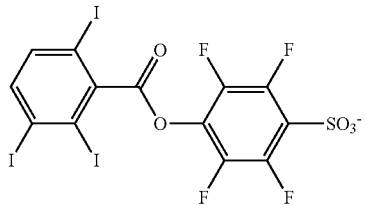
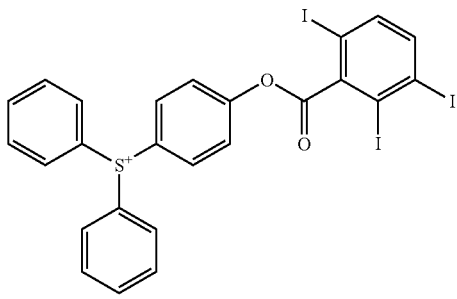
PAG 10
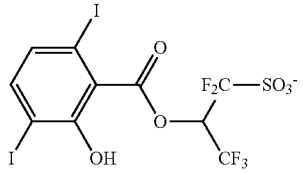
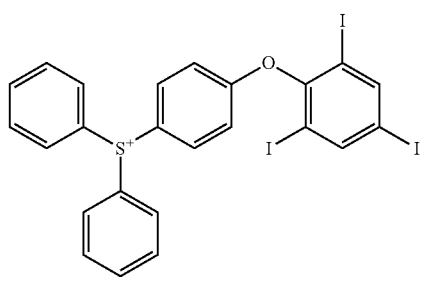
PAG 11
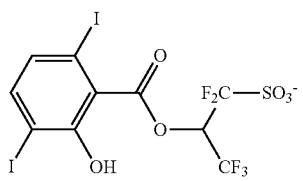
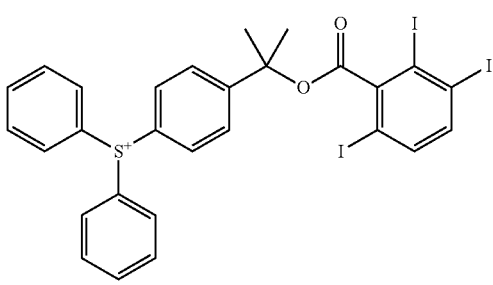
PAG 12
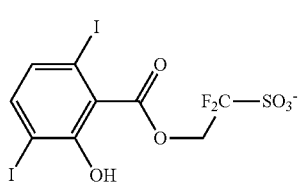
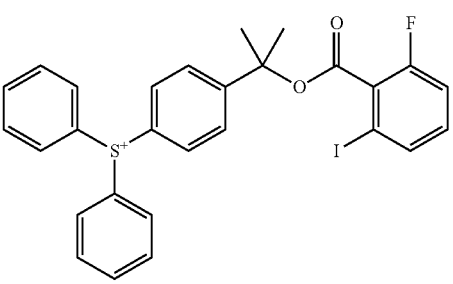
PAG 13
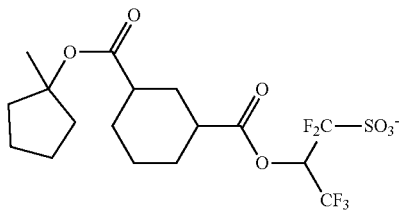
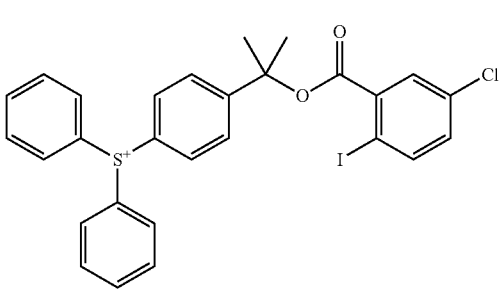
PAG 14

-continued
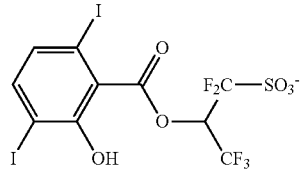
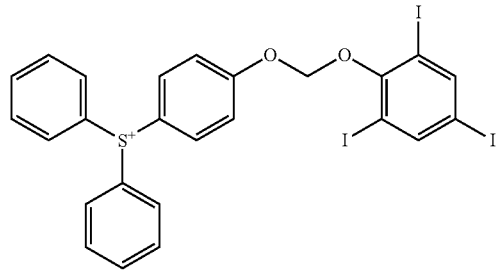
PAG 15
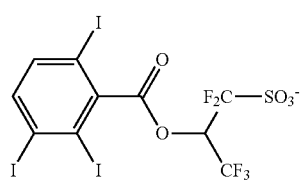
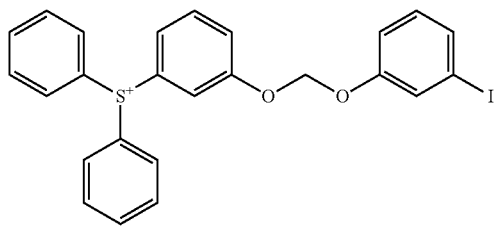
PAG 16
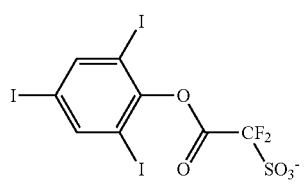
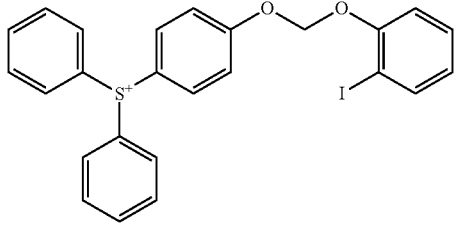
PAG 17
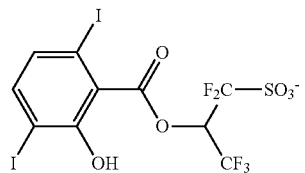
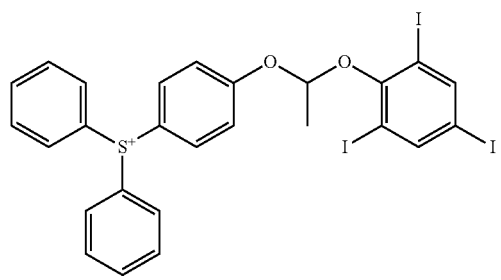
PAG 18
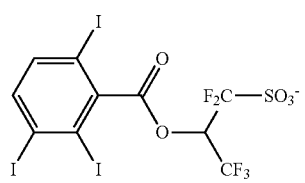
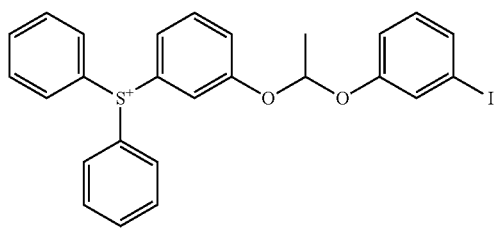
PAG 19
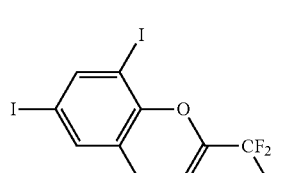
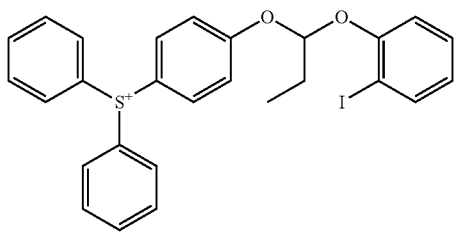
PAG 20

Synthesis Example

Synthesis of Base Polymers (Polymers 1 to 4)

Base polymers were prepared by combining suitable monomers, effecting copolymerization reaction thereof in tetrahydrofuran (THF) solvent, pouring the reaction solution into methanol for crystallization, repeatedly washing with hexane, isolation, and drying. The resulting polymers, designated Polymers 1 to 4, were analyzed for composition by $^1$H-NMR spectroscopy, and for Mw and Mw/Mn by GPC versus polystyrene standards using THF solvent.

Polymer 1

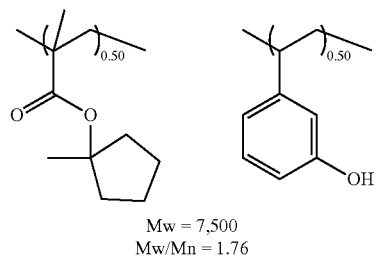

Mw = 7,500
Mw/Mn = 1.76

Polymer 2

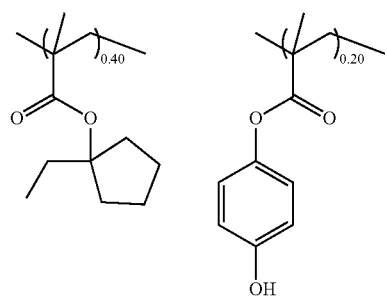

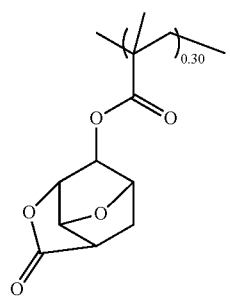

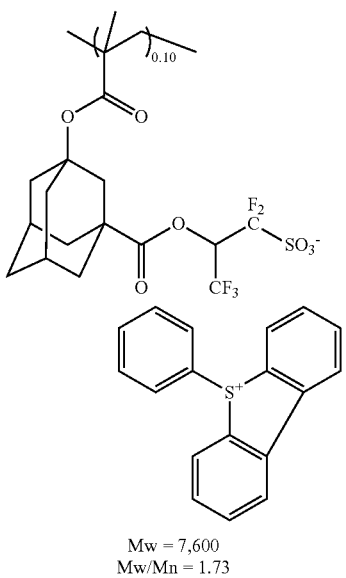

Mw = 7,600
Mw/Mn = 1.73

Polymer 3

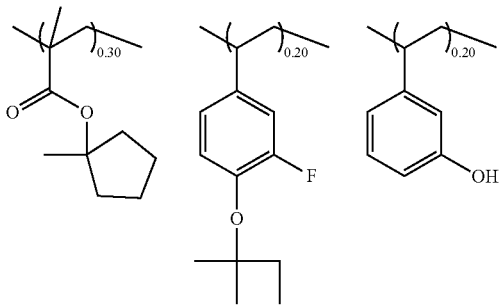

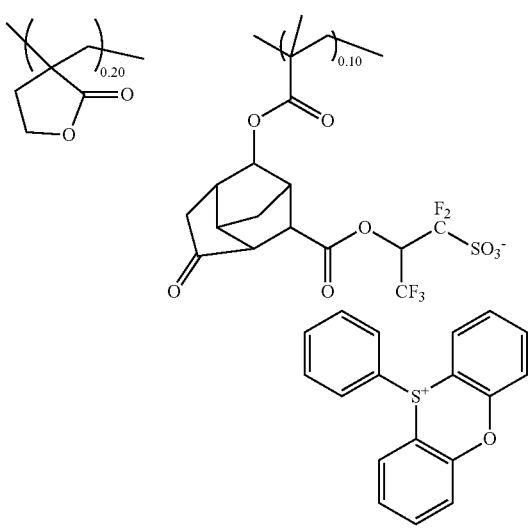

Mw = 9,600
Mw/Mn = 1.72

Polymer 4

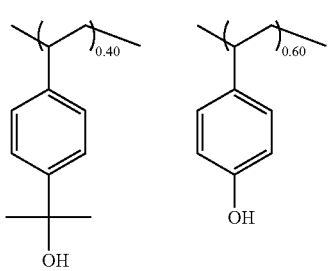

Mw = 6,100
Mw/Mn = 1.54

Examples 1 to 23 and Comparative Examples 1 to 4

(1) Preparation of Resist Composition

Resist compositions were prepared by dissolving components in a solvent in accordance with the recipe shown in Tables 1 and 2, and filtering through a filter having a pore size of 0.2 μm. The solvent contained 100 ppm of surfactant PF636 (Onmova Solutions Inc.). The components in Tables 1 and 2 are as identified below.

Organic Solvents:
  PGMEA (propylene glycol monomethyl ether acetate)
  GBL (γ-butyrolactone)
  CyH (cyclohexanone)
  PGME (propylene glycol monomethyl ether)
  DAA (diacetone alcohol)

Comparative Acid Generators: C-PAG 1 to C-PAG 3 of the Following Structural Formulae

C-PAG 1

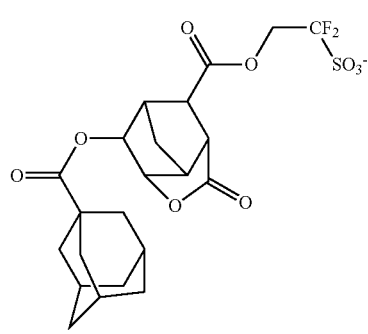

C-PAG 2

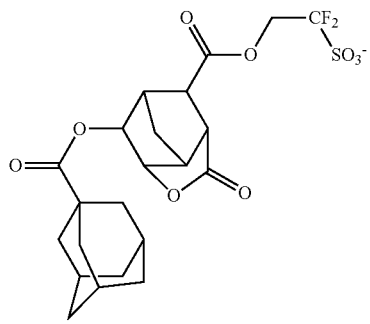

C-PAG 3

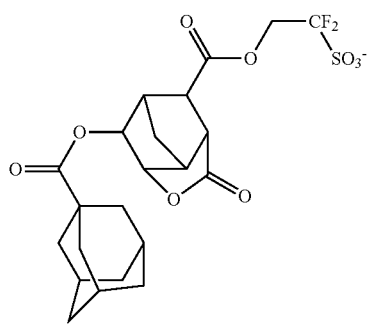

Quenchers 1 to 3 of the Following Structural Formulae

Quencher 1

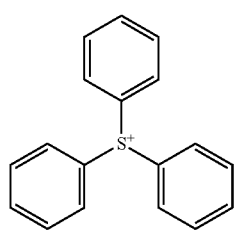

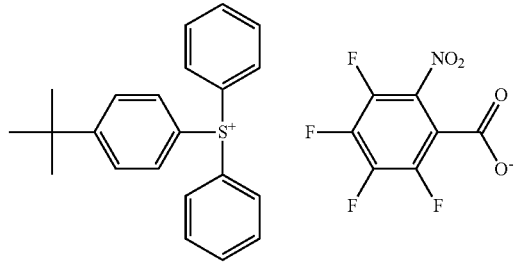

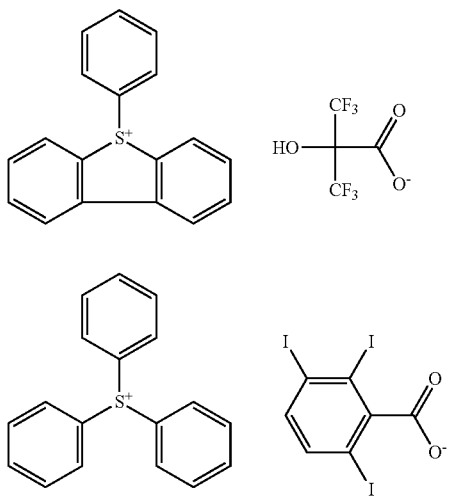

(2) EUV Lithography Test

Each of the resist compositions in Tables 1 and 2 was spin coated on a silicon substrate having a 20-nm coating of silicon-containing spin-on hard mask SHB-A940 (Shin-Etsu Chemical Co., Ltd., Si content 43 wt %) and prebaked on a hotplate at 105° C. for 60 seconds to form a resist film of 50 nm thick. Using an EUV scanner NXE3300 (ASML, NA 0.33, σ0.9/0.6, quadrupole illumination), the resist film was exposed to EUV through a mask bearing a hole pattern at a pitch 46 nm (on-wafer size) and +20% bias. The resist film was baked (PEB) on a hotplate at the temperature shown in Tables 1 and 2 for 60 seconds and developed in a 2.38 wt % TMAH aqueous solution for 30 seconds to form a pattern. In Examples 1 to 13, 15 to 23 and Comparative Examples 1 to 3, a positive resist pattern, i.e., hole pattern having a size of 23 nm was formed. In Example 14 and Comparative Example 4, a negative resist pattern, i.e., dot pattern having a size of 26 nm was formed.

The resist pattern was observed under CD-SEM (CG-5000, Hitachi High-Technologies Corp.). The exposure dose that provides a hole or dot pattern having a size of 23 nm or 26 nm is reported as sensitivity. The size of 50 holes or dots was measured, from which a size variation (3σ) was computed and reported as CDU.

The resist composition is shown in Tables 1 and 2 together with the sensitivity and CDU of EUV lithography.

TABLE 1

| | | Polymer (pbw) | Acid generator (pbw) | Quencher (pbw) | Organic solvent (pbw) | PEB temp. (° C.) | Sensitivity (mJ/cm²) | CDU (nm) |
|---|---|---|---|---|---|---|---|---|
| Example | 1 | Polymer 1 (100) | PAG 1 (25.3) | Quencher 1 (5.00) | PGMEA (400) CyH (2,000) PGME (100) | 95 | 28 | 3.8 |
| | 2 | Polymer 1 (100) | PAG 2 (26.0) | Quencher 1 (5.00) | PGMEA (400) CyH (2,000) PGME (100) | 95 | 29 | 3.0 |
| | 3 | Polymer 1 (100) | PAG 3 (29.3) | Quencher 1 (5.00) | PGMEA (2,000) DAA (500) | 95 | 28 | 3.8 |
| | 4 | Polymer 1 (100) | PAG 4 (30.3) | Quencher 1 (5.00) | PGMEA (2,000) DAA (500) | 95 | 24 | 3.7 |
| | 5 | Polymer 1 (100) | PAG 5 (31.2) | Quencher 1 (5.00) | PGMEA (2,000) DAA (500) | 95 | 23 | 3.7 |
| | 6 | Polymer 1 (100) | PAG 6 (10.6) PAG 4 (15.2) | Quencher 1 (5.00) | PGMEA (2,000) DAA (500) | 95 | 26 | 3.5 |
| | 7 | Polymer 1 (100) | PAG 7 (11.9) PAG 4 (15.2) | Quencher 1 (5.00) | PGMEA (2,000) DAA (500) | 95 | 25 | 3.3 |
| | 8 | Polymer 1 (100) | PAG 8 (30.2) | Quencher 1 (5.00) | PGMEA (2,000) DAA (500) | 95 | 26 | 3.7 |
| | 9 | Polymer 1 (100) | PAG 9 (26.4) | Quencher 1 (5.00) | PGMEA (2,000) DAA (500) | 95 | 25 | 3.6 |
| | 10 | Polymer 1 (100) | PAG 10 (30.0) | Quencher 1 (5.00) | PGMEA (2,000) DAA (500) | 95 | 25 | 3.3 |
| | 11 | Polymer 1 (100) | PAG 11 (26.7) | Quencher 1 (5.00) | PGMEA (2,000) DAA (500) | 95 | 26 | 3.1 |
| | 12 | Polymer 2 (100) | PAG 4 (15.2) | Quencher 2 (4.72) | PGMEA (2,000) DAA (500) | 85 | 21 | 2.8 |
| | 13 | Polymer 3 (100) | PAG 4 (15.2) | Quencher 3 (6.60) | PGMEA (2,000) GBL (500) | 85 | 20 | 2.9 |
| | 14 | Polymer 4 (100) | PAG 1 (15.2) | Quencher 1 (5.00) | PGMEA (2,000) DAA (500) | 130 | 35 | 3.8 |
| | 15 | Polymer 3 (100) | PAG 12 (13.5) | Quencher 1 (5.00) | PGMEA (2,000) DAA (500) | 85 | 20 | 2.6 |
| | 16 | Polymer 3 (100) | PAG 13 (13.5) | Quencher 1 (5.00) | PGMEA (2,000) DAA (500) | 85 | 22 | 2.8 |
| | 17 | Polymer 3 (100) | PAG 14 (14.2) | Quencher 1 (5.00) | PGMEA (2,000) DAA (500) | 85 | 23 | 2.9 |
| | 18 | Polymer 3 (100) | PAG 15 (14.2) | Quencher 1 (5.00) | PGMEA (2,000) DAA (500) | 85 | 21 | 2.6 |
| | 19 | Polymer 3 (100) | PAG 16 (14.2) | Quencher 1 (5.00) | PGMEA (2,000) DAA (500) | 85 | 25 | 2.9 |
| | 20 | Polymer 3 (100) | PAG 17 (14.2) | Quencher 1 (5.00) | PGMEA (2,000) DAA (500) | 85 | 24 | 2.8 |
| | 21 | Polymer 3 (100) | PAG 18 (14.2) | Quencher 1 (5.00) | PGMEA (2,000) DAA (500) | 85 | 23 | 2.6 |

TABLE 1-continued

| | Polymer (pbw) | Acid generator (pbw) | Quencher (pbw) | Organic solvent (pbw) | PEB temp. (° C.) | Sensitivity (mJ/cm$^2$) | CDU (mm) |
|---|---|---|---|---|---|---|---|
| 22 | Polymer 3 (100) | PAG 19 (14.2) | Quencher 1 (5.00) | PGMEA (2,000) DAA (500) | 85 | 22 | 2.9 |
| 23 | Polymer 3 (100) | PAG 20 (14.2) | Quencher 1 (5.00) | PGMEA (2,000) DAA (500) | 85 | 25 | 2.6 |

TABLE 2

| | | Polymer (pbw) | Acid generator (pbw) | Quencher (pbw) | Organic solvent (pbw) | PEB temp. (° C.) | Sensitivity (mJ/cm$^2$) | CDU (mm) |
|---|---|---|---|---|---|---|---|---|
| Comparative Example | 1 | Polymer 1 (100) | C-PAG 1 (15.3) | Quencher 1 (5.00) | PGMEA (400) CyH (2,000) PGME (100) | 95 | 36 | 4.5 |
| | 2 | Polymer 1 (100) | C-PAG 2 (15.7) | Quencher 1 (5.00) | PGMEA (400) CyH (2,000) PGME (100) | 95 | 35 | 4.0 |
| | 3 | Polymer 1 (100) | C-PAG 3 (17.8) | Quencher 1 (5.00) | PGMEA (400) CyH (2,000) PGME (100) | 95 | 33 | 4.1 |
| | 4 | Polymer 4 (100) | C-PAG 1 (15.3) | Quencher 1 (5.00) | PGMEA (2,000) DAA (500) | 130 | 45 | 4.3 |

It is demonstrated in Tables 1 and 2 that resist compositions comprising a sulfonium salt having an iodized benzene ring offer a high sensitivity and improved CDU.

Japanese Patent Application No. 2018-173519 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A resist composition comprising an acid generator containing a sulfonium salt having the formula (1):

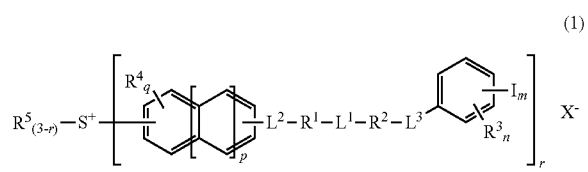

wherein $R^1$ and $R^2$ are each independently a single bond or a $C_1$-$C_{20}$ divalent aliphatic hydrocarbon group which may contain an ether bond, ester bond or hydroxyl, $L^1$ is an ester bond, ether bond or amide bond, $L^2$ and $L^3$ are each independently a single bond, ester bond, ether bond or amide bond, $R^3$ is hydroxyl, carboxyl, nitro, cyano, fluorine, chlorine, bromine, amino, or a $C_1$-$C_{20}$ alkyl, $C_1$-$C_{20}$ alkoxy, $C_2$-$C_{20}$ acyloxy, $C_2$-$C_{20}$ alkoxycarbonyl or $C_1$-$C_4$ alkylsulfonyloxy group, which may contain fluorine, chlorine, bromine, hydroxyl or amino, or —NR$^{3A}$—C(=O)—R$^{3B}$ or —NR$^{3A}$—C(=O)—O—R$^{3B}$, wherein R$^{3A}$ is hydrogen or a $C_1$-$C_6$ alkyl group which may contain halogen, hydroxyl, $C_1$-$C_{10}$ alkoxy, $C_2$-$C_{10}$ acyl or $C_2$-$C_{10}$ acyloxy, R$^{3B}$ is a $C_1$-$C_{16}$ alkyl, $C_2$-$C_{16}$ alkenyl or $C_6$-$C_{12}$ aryl group, which may contain halogen, hydroxyl, $C_1$-$C_{10}$ alkoxy, $C_2$-$C_{10}$ acyl or $C_2$-$C_{10}$ acyloxy, $R^4$ is hydroxyl, carboxyl, nitro, cyano, fluorine, chlorine, bromine, iodine, amino, or a $C_1$-$C_2$alkyl, $C_1$-$C_{20}$ alkoxy, $C_2$-$C_{20}$ acyloxy, $C_2$-$C_{20}$ alkoxycarbonyl or $C_1$-$C_4$ alkylsulfonyloxy group, which may contain fluorine, chlorine, bromine, iodine, hydroxyl, amino or ether bond, $R^5$ is a $C_1$-$C_{20}$ monovalent hydrocarbon group which may contain a heteroatom, in case of r=1, two $R^5$ may be the same or different and may bond together to form a ring with the sulfur atom to which they are attached, $X^-$ is a non-nucleophilic counter ion, m is an integer of 1 to 5, n is an integer of 0 to 3, the sum of m+n is 1 to 5, p is 0 or 1, q is an integer of 0 to 4, and r is an integer of 1 to 3.

2. The resist composition of claim 1 wherein m is an integer of 2 to 5.

3. The resist composition of claim 1 wherein the non-nucleophilic counter ion is a fluorinated sulfonate, fluorinated imide or fluorinated methide ion.

4. The resist composition of claim 1, further comprising an organic solvent.

5. The resist composition of claim 1, further comprising a base polymer.

6. The resist composition of claim 5 wherein the base polymer comprises recurring units having the formula (a1) or recurring units having the formula (a2):

(a2)

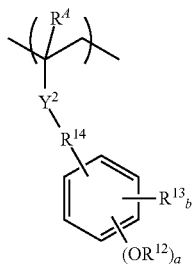

wherein $R^A$ is each independently hydrogen or methyl $Y^1$ is a single bond, phenylene group, naphthylene group, or $C_1$-$C_{12}$ linking group containing an ester bond or lactone ring, $Y^2$ is a single bond or ester bond, $R^{11}$ and $R^{12}$ each are an acid labile group, $R^{13}$ is fluorine, trifluoromethyl, cyano, $C_1$-$C_6$ alkyl, $C_1$-$C_6$ alkoxy, $C_2$-$C_7$ acyl, $C_2$-$C_7$ acyloxy, or $C_2$-$C_7$ alkoxycarbonyl group, $R^{14}$ is a single bond or a $C_1$-$C_6$ straight or branched alkanediyl group in which some carbon may be replaced by an ether bond or ester bond, a is 1 or 2, b is an integer of 0 to 4, the sum of a+b is 1 to 5.

7. The resist composition of claim 6 which is a chemically amplified positive resist composition.

8. The resist composition of claim 5 wherein the base polymer is free of an acid labile group.

9. The resist composition of claim 8 which is a chemically amplified negative resist composition.

10. The resist composition of claim 5 wherein the base polymer further comprises recurring units of at least one type selected from the formulae (f1) to (f3):

(f1)

(f2)

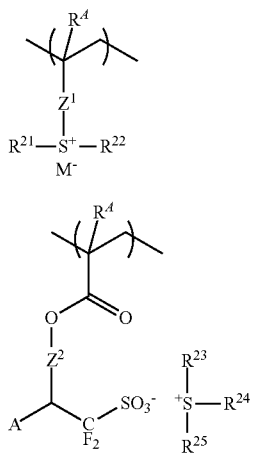

(f3)

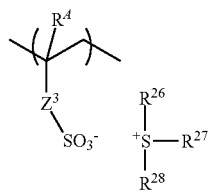

wherein $R^A$ is each independently hydrogen or methyl, $Z^1$ is a single bond, phenylene group, —O—$Z^{11}$—, —C(=O)—O—$Z^{11}$— or —C(=O)—NH—$Z^{11}$—, $Z^{11}$ is a $C_1$-$C_6$ alkanediyl group, $C_2$-$C_6$ alkenediyl group, or phenylene group, which may contain carbonyl, ester bond, ether bond or hydroxyl, $Z^2$ is a single bond, —$Z^{21}$—C(=O)—O—, —$Z^{21}$—O— or —$Z^{21}$—O—C(=O)—, $Z^{21}$ is a $C_1$-$C_{12}$ alkanediyl group which may contain carbonyl, ester bond or ether bond, $Z^3$ is a single bond, methylene, ethylene, phenylene, fluorinated phenylene, —O—$Z^{31}$—, —C(=O)—O—$Z^{31}$— or —C(=O)—NH—$Z^{31}$—, $Z^{31}$ is a $C_1$-$C_6$ alkanediyl group, $C_2$-$C_6$ alkenediyl group, phenylene group, fluorinated phenylene group, or trifluoromethyl-substituted phenylene group, which may contain carbonyl, ester bond, ether bond or hydroxyl, $R^{21}$ to $R^{28}$ are each independently a $C_1$-$C_{20}$ monovalent hydrocarbon group which may contain a heteroatom, any two of $R^{23}$, $R^{24}$ and $R^{25}$ or any two of $R^{26}$, $R^{27}$ and $R^{28}$ may bond together to form a ring with the sulfur atom to which they are attached, A is hydrogen or trifluoromethyl, and $M^-$ is a non-nucleophilic counter ion.

11. The resist composition of claim 1, further comprising a surfactant.

12. A process for forming a pattern comprising the steps of applying the resist composition of claim 1 onto a substrate, baking to form a resist film, exposing the resist film to high-energy radiation, and developing the exposed resist film in a developer.

13. The process of claim 12 wherein the high-energy radiation is ArF excimer laser radiation of wavelength 193 nm or KrF excimer laser radiation of wavelength 248 nm.

14. The process of claim 12 wherein the high-energy radiation is EB or EUV of wavelength 3 to 15 nm.

* * * * *